(12) United States Patent
Zemlok

(10) Patent No.: US 10,760,932 B2
(45) Date of Patent: Sep. 1, 2020

(54) METHODS TO SHORTEN CALIBRATION TIMES FOR POWERED DEVICES

(71) Applicant: Covidien LP, Mansfield, MA (US)

(72) Inventor: Michael A. Zemlok, Prospect, CT (US)

(73) Assignee: Covidien LP, Mansfield, MA (US)

( * ) Notice: Subject to any disclaimer, the term of this patent is extended or adjusted under 35 U.S.C. 154(b) by 110 days.

(21) Appl. No.: 16/055,220

(22) Filed: Aug. 6, 2018

(65) Prior Publication Data

US 2018/0340806 A1 Nov. 29, 2018

Related U.S. Application Data

(63) Continuation of application No. 14/683,407, filed on Apr. 10, 2015, now Pat. No. 10,041,822, which is a
(Continued)

(51) Int. Cl.
*G01D 18/00* (2006.01)
*A61B 17/072* (2006.01)
(Continued)

(52) U.S. Cl.
CPC ..... *G01D 18/008* (2013.01); *A61B 17/07207* (2013.01); *A61B 2017/00017* (2013.01); *A61B 2017/00022* (2013.01); *A61B 2017/00084* (2013.01); *A61B 2017/00119* (2013.01); *A61B 2017/00154* (2013.01); *A61B 2017/00181* (2013.01); *A61B 2017/00199* (2013.01); *A61B 2017/00367* (2013.01); *A61B 2017/00393* (2013.01); *A61B 2017/00398* (2013.01); *A61B 2017/00464* (2013.01); *A61B 2017/00473* (2013.01); *A61B 2017/00477* (2013.01);
(Continued)

(58) Field of Classification Search
CPC .................................................. A61B 17/072
USPC .............................................................. 173/1
See application file for complete search history.

(56) References Cited

U.S. PATENT DOCUMENTS 2,777,340 A 1/1957 Hettwer et al.
2,957,353 A 10/1960 Babacz
(Continued)

FOREIGN PATENT DOCUMENTS

AU 2008229795 A1 4/2009
CA 2451558 A1 1/2003
(Continued)

OTHER PUBLICATIONS

Extended European Search Report dated Jan. 28, 2019 issued in corresponding EP Appln. No. 18198047.5.
(Continued)

*Primary Examiner* — Nathaniel C Chukwurah
(74) *Attorney, Agent, or Firm* — Carter, DeLuca & Farrell LLP

(57) ABSTRACT

A calibration method for a hand-held surgical instrument is disclosed. The hand-held instrument includes a drive motor, a firing rod controlled by the drive motor and having at least one indicator, and a sensor configured to detect the at least one indicator. A microcontroller includes a pulse modulation algorithm stored therein to control the drive motor. The microcontroller executes a calibration algorithm to adjust at least one program coefficient in the pulse modulation algorithm.

16 Claims, 45 Drawing Sheets

Related U.S. Application Data continuation-in-part of application No. 12/895,897, filed on Oct. 1, 2010, now Pat. No. 9,113,880, which is a continuation-in-part of application No. 12/189,834, filed on Aug. 12, 2008, now abandoned.

(60) Provisional application No. 61/248,971, filed on Oct. 6, 2009, provisional application No. 61/248,504, filed on Oct. 5, 2009, provisional application No. 60/997,854, filed on Oct. 5, 2007.

(51) Int. Cl.
    A61B 17/00    (2006.01)
    A61B 17/29    (2006.01)
    A61B 17/32    (2006.01)
    A61B 90/00    (2016.01)

(52) U.S. Cl.
    CPC ........... A61B 2017/00482 (2013.01); A61B 2017/00725 (2013.01); A61B 2017/00734 (2013.01); A61B 2017/2927 (2013.01); A61B 2017/2931 (2013.01); A61B 2017/320052 (2013.01); A61B 2090/0811 (2016.02)

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,562,239 A | 10/1996 | Boiarski et al. |
| 5,632,432 A | 5/1997 | Schulze et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,732,871 A | 3/1998 | Clark et al. |
| 5,762,603 A | 6/1998 | Thompson |
| 5,769,791 A | 6/1998 | Benaron et al. |
| 5,779,130 A | 7/1998 | Alesi et al. |
| 5,782,396 A | 7/1998 | Mastri et al. |
| 5,782,397 A | 7/1998 | Koukline |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,192,840 B1 | 2/2001 | Durr et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |

(56) References Cited

U.S. PATENT DOCUMENTS

| | | |
|---|---|---|
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,473,263 B2 | 1/2009 | Johnston et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,556,185 B2 | 7/2009 | Viola |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,176 B2 | 9/2009 | Timm et al. |
| 7,607,557 B2 | 10/2009 | Shelton, IV et al. |
| 7,624,902 B2 | 12/2009 | Marczyk et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,648,055 B2 | 1/2010 | Marczyk |
| 7,651,835 B2 | 1/2010 | Hassanein et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,721,936 B2 | 5/2010 | Shalton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,753,248 B2 | 7/2010 | Viola |
| 7,757,925 B2 | 7/2010 | Viola et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,789,283 B2 | 9/2010 | Shah |
| 7,793,812 B2 | 9/2010 | Moore et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,802,712 B2 | 9/2010 | Milliman et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,861,906 B2 | 1/2011 | Doll et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,052,024 B2 | 11/2011 | Viola et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,888,762 B2 | 11/2014 | Whitman |
| 8,899,462 B2 | 12/2014 | Kostrzewski et al. |
| 8,960,519 B2 | 2/2015 | Whitman et al. |
| 8,968,276 B2 | 3/2015 | Zemlok et al. |
| 10,041,822 B2 * | 8/2018 | Zemlok ............ A61B 17/07207 |
| 2001/0031975 A1 | 10/2001 | Whitman |
| 2002/0165541 A1 | 11/2002 | Whitman |
| 2003/0038938 A1 | 2/2003 | Jung et al. |
| 2003/0050628 A1 | 3/2003 | Whitman |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2005/0080345 A1 | 4/2005 | Finburgh et al. |
| 2005/0131442 A1 | 6/2005 | Yachia et al. |
| 2006/0142656 A1 | 6/2006 | Malackowski et al. |
| 2006/0142744 A1 | 6/2006 | Boutoussov |
| 2006/0259073 A1 | 11/2006 | Miyamoto et al. |
| 2006/0278680 A1 * | 12/2006 | Viola ............... A61B 17/07207 227/176.1 |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0090611 A1 | 4/2007 | Soroka et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0179476 A1 | 8/2007 | Shelton et al. |
| 2007/0188603 A1 | 8/2007 | Riederer et al. |
| 2007/0270784 A1 | 11/2007 | Smith et al. |
| 2008/0021334 A1 | 1/2008 | Finburgh et al. |

(56) References Cited

U.S. PATENT DOCUMENTS

| | | |
|---|---|---|
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0114389 A1 | 5/2008 | Johnston et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2009/0057369 A1 | 3/2009 | Smith et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0163929 A1 | 6/2009 | Yeung et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0023022 A1 | 1/2010 | Zeiner et al. |
| 2010/0049152 A1 | 2/2010 | Lalomia et al. |
| 2010/0069942 A1 | 3/2010 | Shelton, IV |
| 2010/0225073 A1 | 9/2010 | Porter et al. |
| 2010/0286791 A1 | 11/2010 | Goldsmith |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0204119 A1 | 8/2011 | McCuen |
| 2011/0218522 A1 | 9/2011 | Whitman |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2013/0018361 A1 | 1/2013 | Bryant |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0102289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |

FOREIGN PATENT DOCUMENTS

| | | |
|---|---|---|
| CN | 102247182 A | 11/2011 |
| CN | 104224255 A | 12/2014 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1769754 A1 | 4/2007 |
| EP | 1772105 A1 | 4/2007 |
| EP | 1813199 A1 | 8/2007 |
| EP | 1813203 A2 | 8/2007 |
| EP | 1813211 A2 | 8/2007 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 1980214 A2 | 10/2008 |
| EP | 1982657 A2 | 10/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2092898 A2 | 8/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2462878 A1 | 6/2012 |
| EP | 2462880 A2 | 6/2012 |
| EP | 2491872 A1 | 8/2012 |
| EP | 2586382 A2 | 5/2013 |
| EP | 2606834 A2 | 6/2013 |
| EP | 2676615 A2 | 12/2013 |
| EP | 2777521 A2 | 9/2014 |
| EP | 2789299 A1 | 10/2014 |
| ES | 2333509 A1 | 2/2010 |
| JP | 08038488 | 2/1996 |
| JP | 2005125075 A | 5/2005 |
| WO | 9915086 A1 | 4/1999 |
| WO | 0072760 A1 | 12/2000 |
| WO | 0072765 A1 | 12/2000 |
| WO | 03000138 A2 | 1/2003 |
| WO | 03026511 A1 | 4/2003 |
| WO | 03030743 A2 | 4/2003 |
| WO | 03065916 A1 | 8/2003 |
| WO | 03077769 A1 | 9/2003 |
| WO | 03090630 A2 | 11/2003 |
| WO | 2004107989 A1 | 12/2004 |
| WO | 2006042210 A2 | 4/2006 |
| WO | 2007016290 A2 | 2/2007 |
| WO | 2007026354 A1 | 3/2007 |
| WO | 2007137304 A2 | 11/2007 |
| WO | 2008131362 A2 | 10/2008 |
| WO | 2008133956 A1 | 11/2008 |
| WO | 2009032838 A1 | 3/2009 |
| WO | 2009039506 A1 | 3/2009 |
| WO | 2007014355 A3 | 4/2009 |
| WO | 2009079781 A1 | 7/2009 |
| WO | 2009132359 A2 | 10/2009 |
| WO | 2009143092 A1 | 11/2009 |
| WO | 2009149234 A1 | 12/2009 |

(56) References Cited

FOREIGN PATENT DOCUMENTS

| WO | 2011108840 A2 | 9/2011 |
| WO | 2012040984 A1 | 4/2012 |

OTHER PUBLICATIONS

European Search Report dated Mar. 10, 2011 for the corresponding application EP10251741, dated Mar. 1, 2011.
European Search Report EP16164421 dated Jun. 16, 2016.
Chinese Office Action dated Oct. 8, 2019 issued in corresponding CN Appln. No. 201610221797.7.
Australian Examination Report dated Oct. 28, 2019 issued in corresponding AU Appln. No. 2016202115.
Japanese Office Action dated Dec. 27, 2019 issued in corresponding JP Appln. No. 2016-075709.
Chinese Office Action dated May 27, 2020 issued in corresponding CN Appln. No. 201610221797.7.

\* cited by examiner

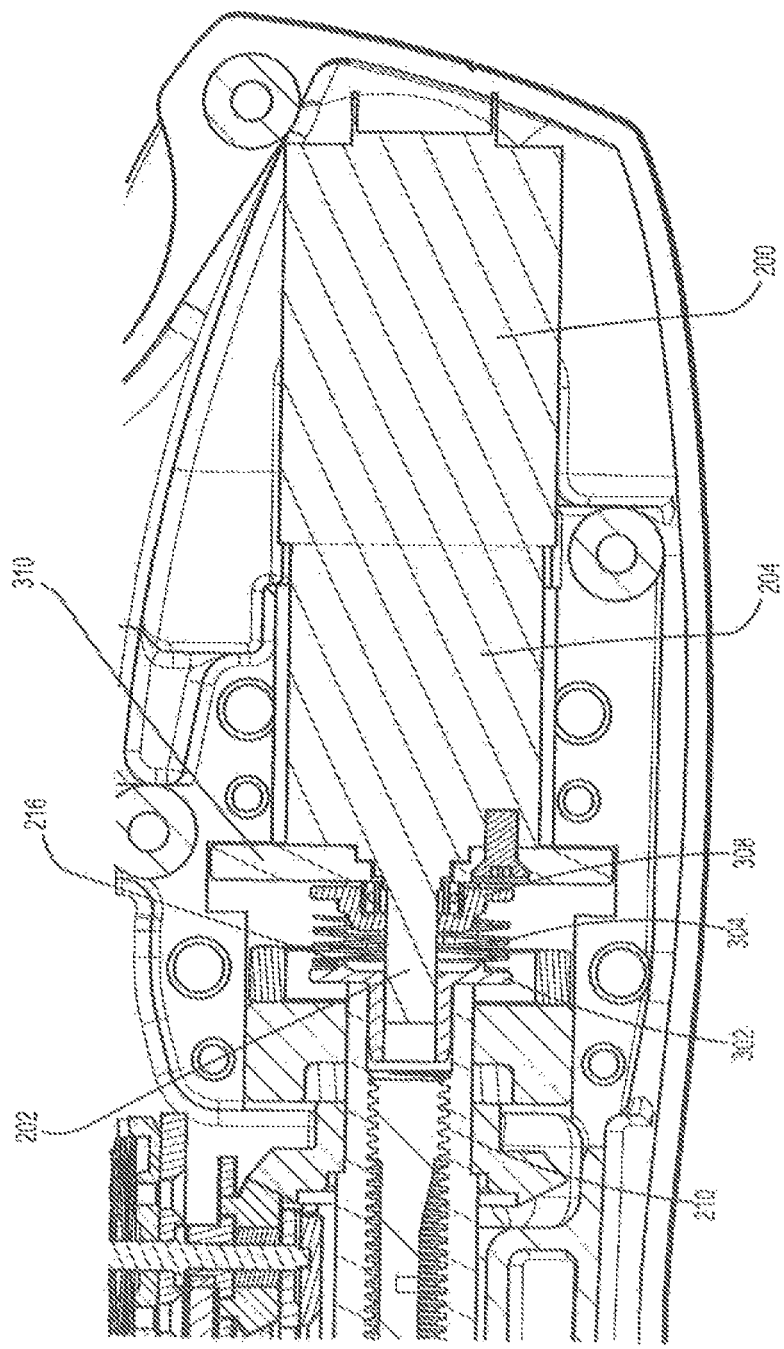

METHODS TO SHORTEN CALIBRATION TIMES FOR POWERED DEVICES

CROSS-REFERENCE TO RELATED APPLICATIONS

This application is a continuation of U.S. patent application Ser. No. 14/683,407, filed Apr. 10, 2015, which is a continuation-in-part of U.S. patent application Ser. No. 12/895,897, filed on Oct. 1, 2010, (now U.S. Pat. No. 9,113,880), which claims priority to U.S. Provisional Patent Application Ser. No. 61/248,971, filed on Oct. 6, 2009, and to U.S. Provisional Patent Application Ser. No. 61/248,504, filed on Oct. 5, 2009. U.S. patent application Ser. No. 12/895,897, filed on Oct. 1, 2010, is a continuation-in-part, (now abandoned), of U.S. patent application Ser. No. 12/189,834, filed on Aug. 8, 2008, which claims priority to U.S. Provisional Patent Application Ser. No. 60/997,854, filed on Oct. 5, 2007. The entire contents of the above-mentioned applications are hereby incorporated by reference herein.

BACKGROUND

1. Technical Field

The present disclosure relates to a surgical stapler for implanting mechanical surgical fasteners into the tissue of a patient, and, in particular, to a surgical stapler which is powered by a motor for firing surgical fasteners into tissue and a controller for determining one or more conditions related to the firing of the surgical fasteners and controlling the stapler in response to one or more sensed feedback signals.

2. Background of Related Art

Motor-powered surgical staplers include motors which translate components that are used to clamp tissue and activate a staple firing mechanism. Pre-stapling calibration identifies the current position of the translating components. This calibration can be time consuming, requiring full strokes of the translating components to their full proximal and distal stop positions. Additionally, precise calibration may be difficult where tolerances between mating components and/or gear meshes have some gap or slip associated to enable assembly of the motor-powered surgical stapler. Thus, there is a need for new and improved powered surgical staplers that precisely determine the position of the translating components to calibrate the powered surgical staplers.

SUMMARY

In an aspect of the present disclosure, a hand-held surgical instrument is provided. The hand-held surgical instrument includes a drive motor, a firing rod controlled by the drive motor and having at least one indicator, and a sensor configured to detect the indicator. The hand-held surgical instrument also includes a microcontroller having a pulse modulation algorithm stored therein to control the drive motor. The microcontroller executes a calibration algorithm to adjust a program coefficient in the pulse modulation algorithm.

The indicator may be a bump, groove, indentation, magnet, notch, or at least one thread on the firing rod. The sensor may be a linear displacement sensor.

In some aspects, the instrument also includes a position calculator configured to determine a time between when the firing rod begins translation and when the sensor detects the indicator. The microcontroller receives the determined time from the position calculator and compares the determined time to a stored predetermined time. The microcontroller adjusts a program coefficient based on the comparison between the determined time and the stored predetermined time.

In other aspects, the sensor also determines the linear speed of the firing rod and selects the stored predetermined time based on the linear speed.

In another aspect of the present disclosure, a method for calibrating a hand-held surgical instrument having a drive motor, a firing rod, a sensor, a microcontroller, and a memory having a pulse modulation algorithm stored therein is provided. The method includes initiating translation of the firing rod, detecting at least one indicator on the firing rod, and determining a time between when translation of the firing rod is initiated and when the indicator is detected. The method also includes comparing the determined time with a stored predetermined time and adjusting at least one program coefficient in the pulse modulation algorithm based on the comparison between the determined time and the stored predetermined time.

In some aspects, if the determined time is less than the predetermined time, a program coefficient is adjusted so that the firing rod is translated a relatively shorter distance.

In other aspects, if the time is greater than the predetermined time, the program coefficient is adjusted so that the firing rod is translated a relatively longer distance.

In aspects, the linear speed of the firing rod is determined, and the stored predetermined time is selected based on the determined linear speed.

BRIEF DESCRIPTION OF THE DRAWINGS

Various embodiments of the subject instrument are described herein with reference to the drawings wherein:

FIG. 10A is a partial enlarged cross-sectional view of the internal components of the variant of the powered surgical instrument of FIG. 4A;

DETAILED DESCRIPTION

Figure 1:
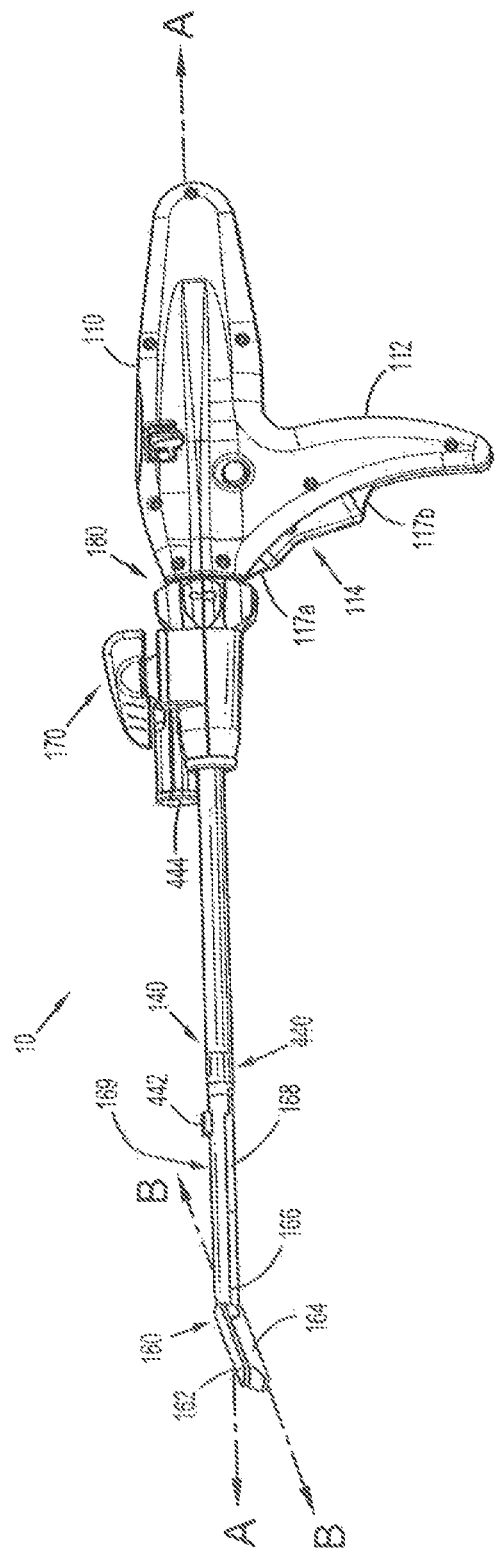
FIG. 1 is a perspective view of a powered surgical instrument according to an exemplary embodiment of the present disclosure.

Embodiments of the presently disclosed powered surgical instrument are now described in detail with reference to the drawings, in which like reference numerals designate identical or corresponding elements in each of the several views. As used herein the term "distal" refers to that portion of the powered surgical instrument, or component thereof, farther from the user while the term "proximal" refers to that portion of the powered surgical instrument or component thereof, closer to the user.

Additionally, in the drawings and in the description that follows, terms such as "front", "rear", "upper", "lower", "top", "bottom" and the like are used simply for convenience of description and are not intended to limit the disclosure thereto.

A powered surgical instrument, e.g., a surgical stapler, in accordance with the present disclosure is referred to in the figures as reference numeral 10. Referring initially to FIG. 1, powered surgical instrument 10 includes a housing 110, an endoscopic portion 140 defining a first longitudinal axis A-A extending therethrough, and an end effector 160, defining a second longitudinal axis B-B extending therethrough. Endoscopic portion 140 extends distally from housing 110 and the end effector 160 is disposed adjacent a distal portion of endoscopic portion 140. In an embodiment, the components of the housing 110 are sealed against infiltration of particulate and/or fluid contamination and help prevent damage of the component by the sterilization process.

According to an embodiment of the present disclosure, end effector 160 includes a first jaw member having one or more surgical fasteners (e.g., cartridge assembly 164) and a second opposing jaw member including an anvil portion for deploying and forming the surgical fasteners (e.g., an anvil assembly 162). In certain embodiments, the staples are housed in cartridge assembly 164 to apply linear rows of staples to body tissue either in simultaneous or sequential manner. Either one or both of the anvil assembly 162 and the cartridge assembly 164 are movable in relation to one another between an open position in which the anvil assembly 162 is spaced from cartridge assembly 164 and an approximated or clamped position in which the anvil assembly 162 is in juxtaposed alignment with cartridge assembly 164.

It is further envisioned that end effector 160 is attached to a mounting portion 166, which is pivotably attached to a body portion 168. Body portion 168 may be integral with endoscopic portion 140 of powered surgical instrument 10, or may be removably attached to the instrument 10 to provide a replaceable, disposable loading unit (DLU) or single use loading unit (SULU) (e.g., loading unit 169). In certain embodiments, the reusable portion may be configured for sterilization and re-use in a subsequent surgical procedure.

The loading unit 169 may be connectable to endoscopic portion 140 through a bayonet connection. It is envisioned that the loading unit 169 has an articulation link connected to mounting portion 166 of the loading unit 169 and the articulation link is connected to a linkage rod so that the end effector 160 is articulated as the linkage rod is translated in the distal-proximal direction along first longitudinal axis A-A. Other means of connecting end effector 160 to endoscopic portion 140 to allow articulation may be used, such as a flexible tube or a tube comprising a plurality of pivotable members.

The loading unit 169 may incorporate or be configured to incorporate various end effectors, such as vessel sealing devices, linear stapling devices, circular stapling devices, cutters, etc. Such end effectors may be coupled to endoscopic portion 140 of powered surgical instrument 10. The loading unit 169 may include a linear stapling end effector that does not articulate. An intermediate flexible shaft may be included between handle portion 112 and loading unit. It is envisioned that the incorporation of a flexible shaft may facilitate access to and/or within certain areas of a patient's body.

Figure 2:
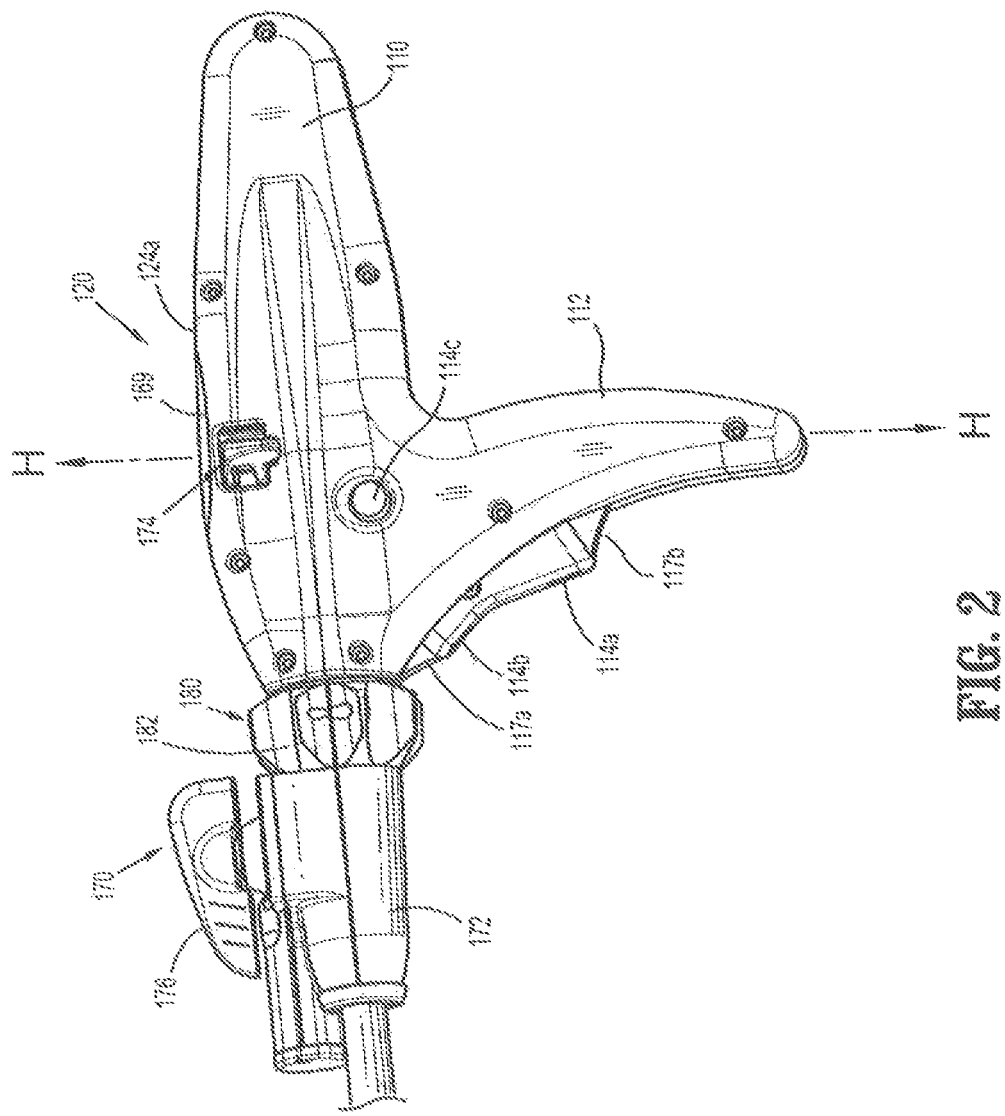
FIG. 2 is a partial enlarged perspective view of the powered surgical instrument of FIG. 1.

With reference to FIG. 2, an enlarged view of the housing 110 is illustrated according to an embodiment of the present disclosure. In the illustrated embodiment, housing 110 includes a handle portion 112 having a main drive switch 114 disposed thereon. The switch 114 may include first and second switches 114a and 114b formed together as a toggle switch. The handle portion 112, which defines a handle axis H-H, is configured to be grasped by fingers of a user. The handle portion 112 has an ergonomic shape providing ample palm grip leverage which helps prevent the handle portion 112 from being squeezed out of the user's hand during operation. Each switch 114a and 114b is shown as being disposed at a suitable location on handle portion 112 to facilitate its depression by a user's finger or fingers. In another embodiment, the instrument 10 includes two separates switches 114a and 114b separated by a rib feature.

Figure 4:
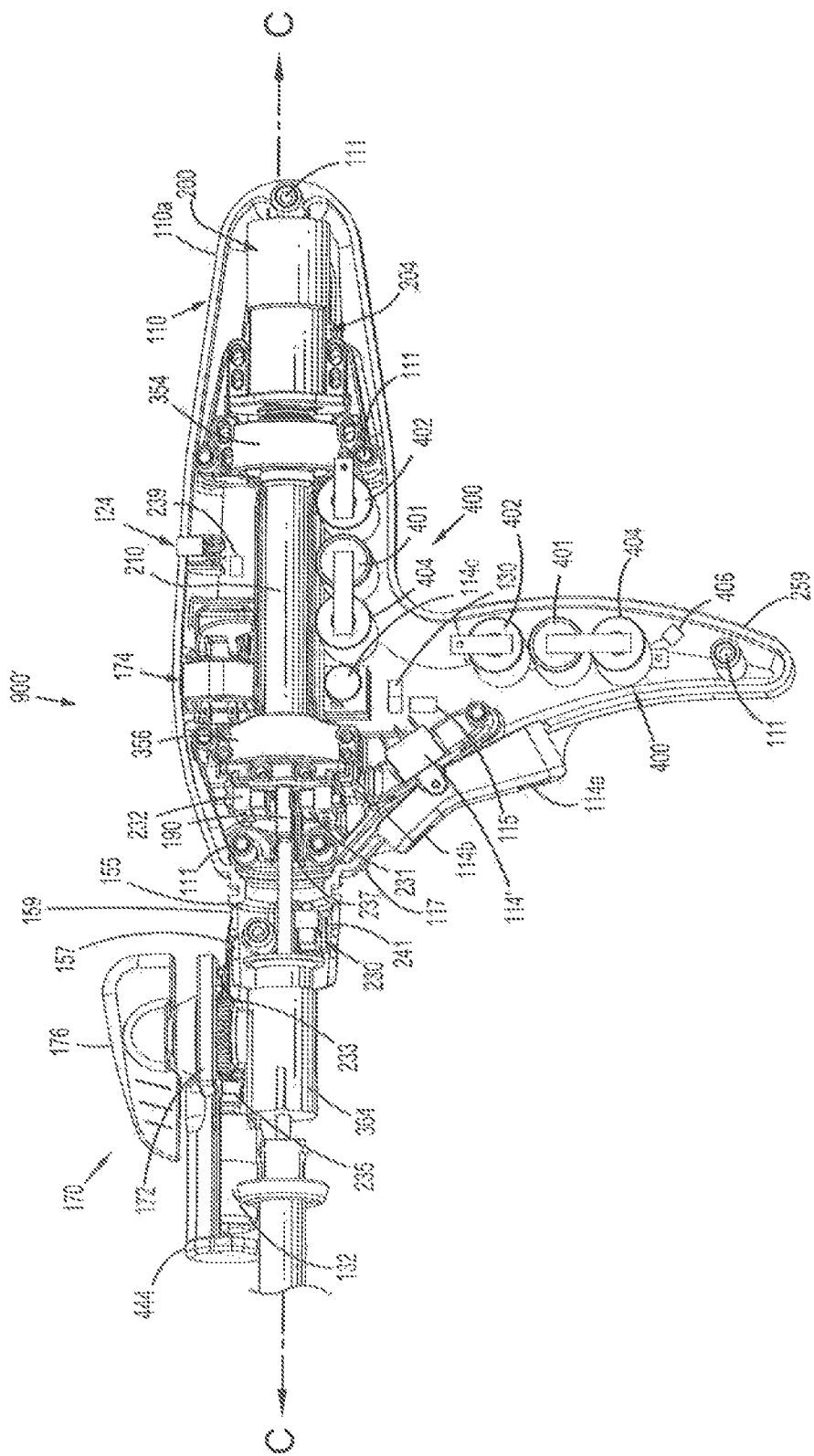
FIG. 4 is a partial sectional view of internal components of the powered surgical instrument of FIG. 1.

Additionally, and with reference to FIGS. 1 and 2, switches 114a, 114b may be used for starting and/or stopping movement of drive motor 200 (FIG. 4). In one embodiment, the switch 114a is configured to activate the drive motor 200 in a first direction to advance firing rod 220 (FIG. 6) in a distal direction thereby clamping the anvil and the cartridge assemblies 162 and 164. Conversely, the switch 114b may be configured to retract the firing rod 220 to open the anvil and cartridge assemblies 162 and 164 by activating the drive motor 200 in a reverse direction. Once the stapling and cutting mode has been initiated, during the retraction mode, a mechanical lock out (not shown) is actuated, preventing further progression of stapling and cutting by the loading unit 169. The lockout is redundantly backed up with software to prevent the cutting of tissue after the staples have been previously deployed. The toggle has a first position for activating switch 114a, a second position for activating switch 114b, and a neutral position between the first and second positions. The details of operation of the drive components of the instrument 10 are discussed in more detail below.

The housing 110, in particular the handle portion 112, includes switch shields 117a and 117b. The switch shields 117a and 117b may have a rib-like shape surrounding the bottom portion of the switch 114a and the top portion of the switch 114b, respectively. The switch shield 117a and 117b prevent accidental activation of the switch 114. Further, the switches 114a and 114b have high tactile feedback requiring increased pressure for activation.

In one embodiment, the switches 114a and 114b are configured as multi-speed (e.g., two or more), incremental or variable speed switches which control the speed of the drive motor 200 and the firing rod 220 in a non-linear manner. For example, switches 114a, b can be pressure-sensitive. This type of control interface allows for gradual increase in the rate of speed of the drive components from a slower and more precise mode to a faster operation. To prevent accidental activation of retraction, the switch 114b may be disconnected electronically until a fail safe switch is pressed. In addition a third switch 114c may also be used for this purpose. Additionally or alternatively, the fail safe can be overcome by pressing and holding the switch 114b for a predetermined period of time from about 100 ms to about 2 seconds. The firing rod 220 then automatically retracts to its initial position unless the switches 114a and 114b are activated (e.g., pressed and released) during the retraction mode to stop the retraction. Subsequent pressing of the switch 114b after the release thereof resumes the retraction. Alternatively, the retraction of the firing rod 220 can continue to full retraction even if the switch 114b is released, in other embodiments. Other embodiments include an auto retract mode of the firing rod 220 that fully retracts the firing rod 220 even if switch 114b is released. The mode may be interrupted at any time if one of the switches 114a or 114b is actuated.

The switches 114a and 114b are coupled to a non-linear speed control circuit 115 which can be implemented as a voltage regulation circuit, a variable resistance circuit, or a microelectronic pulse width modulation circuit. The switches 114a and 144b may interface with the control circuit 115 by displacing or actuating variable control devices, such as rheostatic devices, multiple position switch circuit, linear and/or rotary variable displacement transducers, linear and/or rotary potentiometers, optical encoders, ferromagnetic sensors, and Hall Effect sensors. This allows the switches 114a and 114b to operate the drive motor 200 in multiple speed modes, such as gradually increasing the speed of the drive motor 200 either incrementally or gradually depending on the type of the control circuit 115 being used, based on the depression of the switches 114a and 114b.

In a particular embodiment, the switch 114c may also be included (FIGS. 1, 2 and 4), wherein depression thereof may mechanically and/or electrically change the mode of operation from clamping to firing. The switch 114c is recessed within the housing 110 and has high tactile feedback to prevent false actuations. Providing a separate control switch to initialize the firing mode allows the jaws of the end effector to be repeatedly opened and closed, so that the instrument 10 is used as a grasper until the switch 114c is pressed, thus activating the stapling and/or cutting mode. The switch 114 may include one or more microelectronic switches, for example. For example, a microelectronic membrane switch provides a tactile feel, small package size, ergonomic size and shape, low profile, the ability to include molded letters on the switch, symbols, depictions and/or indications, and a low material cost. Additionally, switches 114 (such as microelectronic membrane switches) may be sealed to help facilitate sterilization of the instrument 10, as well as helping to prevent particle and/or fluid contamination.

As an alternative to, or in addition to switches 114, other input devices may include voice input technology, which may include hardware and/or software incorporated in a control system 501 (FIG. 20), or a separate digital module connected thereto. The voice input technology may include voice recognition, voice activation, voice rectification, and/or embedded speech. The user may be able to control the operation of the instrument in whole or in part through voice commands, thus freeing one or both of the user's hands for operating other instruments. Voice or other audible output may also be used to provide the user with feedback.

Figure 2A:
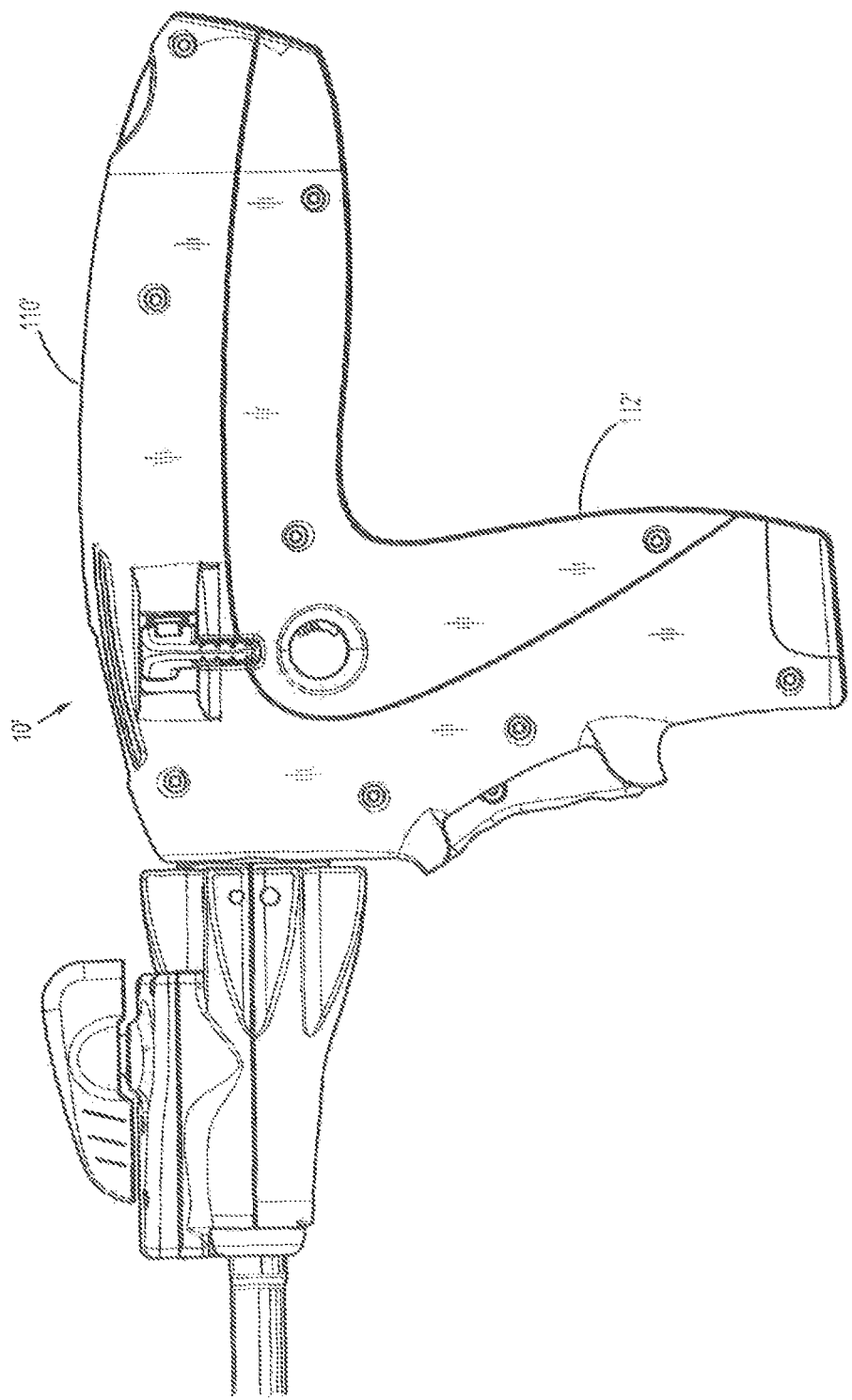
FIG. 2A is a partial enlarged perspective view of a variant of the powered surgical instrument of FIGS. 1 and 2.
Figure 2B:
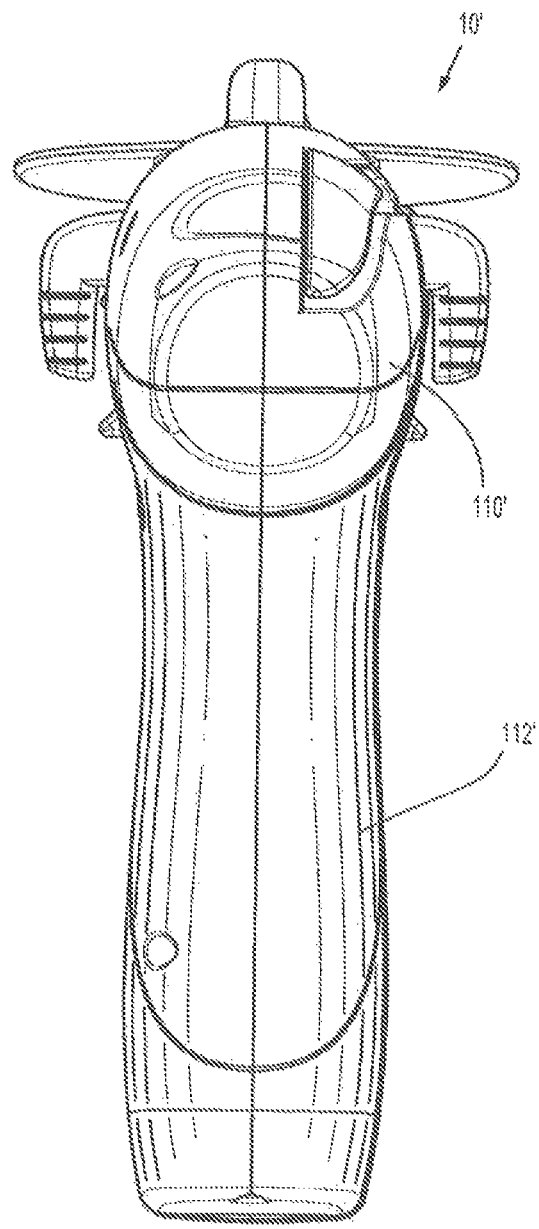
FIG. 2B is a proximal end view of the variant of the powered surgical instrument of FIG. 2A.

Prior to continuing the description of surgical instrument 10, FIGS. 2A and 2B illustrate a variant of surgical instrument 10. More particularly, surgical instrument 10' includes a housing 110' that is configured with a handle 112' having a partial hour-glass shape. Surgical instrument 10' provides an alternative ergonomic configuration to surgical instrument 10.

Figure 3:
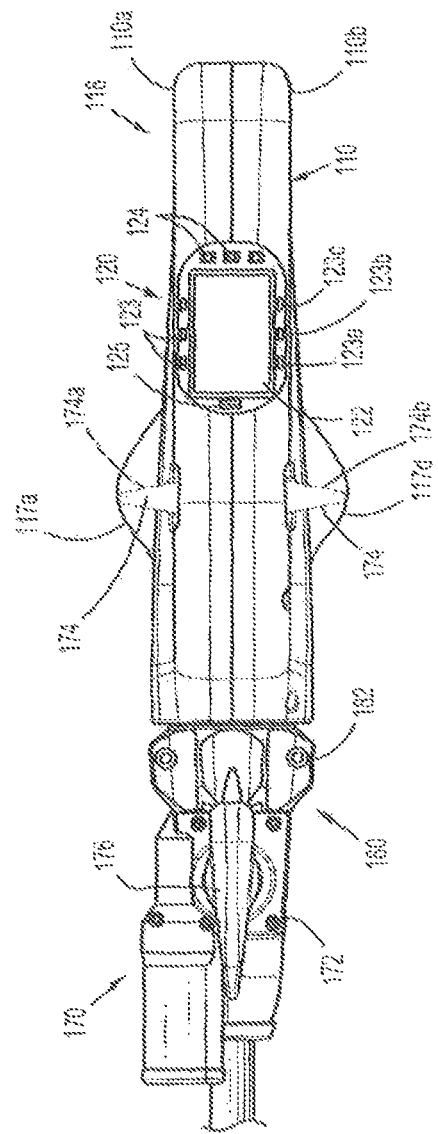
FIG. 3 is a partial enlarged plan view of the powered surgical instrument of FIG. 1.

Returning again to the description of surgical instrument 10 and referring to FIG. 3, a proximal area 118 of housing 110 having a user interface 120 is shown. The user interface 120 includes a screen 122 and a plurality of switches 124. The user interface 120 may display various types of operational parameters of the instrument 10 which may be based on the information reported by sensors disposed in the instrument 10 and communicated to user interface 120. Illustrative operational parameters include "mode" (e.g., rotation, articulation or actuation), "status" (e.g., angle of articulation, speed of rotation, or type of actuation), and "feedback," such as whether staples have been fired. Error and other codes (e.g., improper loading, replace battery, battery level, the estimated number of firings remaining, or any non-functioning sub systems) may also be displayed on user interface 120.

The screen 122 may be an LCD screen, a plasma screen, an electroluminescent screen or the like. In one embodiment the screen 122 may be a touch screen, obviating the need for the switches 124. The touch screen may incorporate resistive, surface wave, capacitive, infrared, strain gauge, optical, dispersive signal or acoustic pulse recognition touch screen technologies. The touch screen may be used to allow the user to provide input while viewing operational feedback. This approach allows sealed screen components to help sterilize the instrument 10, as well as preventing particle and/or fluid contamination. In certain embodiments, the screen 122 is pivotably or rotatably mounted to the instrument 10 for flexibility in viewing screen during use or preparation (e.g., via a hinge or ball-and-socket mount).

The switches 124 may be used for starting and/or stopping movement of the instrument 10 as well as selecting the type of single use loading unit (SULU) or disposable loading unit (DLU), the pivot direction, speed and/or torque. It is also envisioned that at least one switch 124 can be used for selecting an emergency mode that overrides various settings. The switches 124 may also be used for selecting various options on the screen 122, such as responding to prompts while navigating user interface menus and selecting various settings, allowing a user input different tissue types, and various sizes and lengths of staple cartridges.

The switches 124 may be formed from a micro-electronic tactile or non-tactile membrane, a polyester membrane, elastomer, plastic, or metal keys of various shapes and sizes. Additionally, switches may be positioned at different heights from one another and/or may include raised indicia or other textural features (e.g., concavity or convexity) to allow a user to depress an appropriate switch without the need to look at user interface 120.

In addition to the screen 124, the user interface 120 may include one or more visual outputs 123 which may include one or more colored visible lights or light emitting diodes ("LED") to relay feedback to the user. The visual outputs 123 may include corresponding indicators of various shapes, sizes and colors having numbers and/or text which identify the visual outputs 123. The visual outputs 123 are disposed on top of the housing 110 such that the outputs 123 are raised and protrude in relation to the housing 110 providing for better visibility thereof.

The multiple lights display in a certain combination to illustrate a specific operational mode to the user. In one embodiment, the visual outputs 123 include a first light (e.g., yellow) 123a, a second light (e.g., green) 123b and a third light (e.g., red) 123c. The lights are operated in a particular combination associated with a particular operational mode as listed in Table 1 below.

TABLE 1

Light Combination

| Light | Status | Operational Mode |
|---|---|---|
| First Light | Off | No loading unit 169 or staple cartridge is loaded. |
| Second Light | Off | |
| Third Light | Off | |
| First Light | On | The loading unit 169 and/or staple cartridge is properly loaded and power is activated, allowing the end effector 160 to clamp as a grasper and articulate. |
| Second Light | Off | |
| Third Light | Off | |
| First Light | Flashing | A used loading unit 169 or staple cartridge is loaded. |
| Second Light | Off | |
| Third Light | Off | |
| First Light | N/A | Instrument 10 is deactivated and prevented from firing staples or cutting. |
| Second Light | Off | |
| Third Light | N/A | |
| First Light | On | A new loading unit 169 is loaded, the end effector 160 is fully clamped and the instrument 10 is in firing staple and cutting modes. |
| Second Light | On | |
| Third Light | Off | |
| First Light | On | Due to high stapling forces a "thick tissue" mode is in effect, providing for a pulsed or progression time delay during which tissue is compressed. |
| Second Light | Flashing | |
| Third Light | Off | |

TABLE 1-continued

Light Combination

| Light | Status | Operational Mode |
|---|---|---|
| First Light | N/A | No system errors detected. |
| Second Light | N/A | |
| Third Light | Off | |
| First Light | On | Tissue thickness and/or firing load is too high, |
| Second Light | On | this warning can be overridden. |
| Third Light | On | |
| First Light | N/A | Functional system error is detected, instrument |
| Second Light | N/A | 10 should be replaced. |
| Third Light | Flashing | |
| First light | N/A | Replace the battery pack or the power source |
| Second light | N/A | is not properly connected. |
| Third light | ON | |

In another embodiment, the visual output 123 may include a single multi-colored LED which display a particular color associated with the operational modes as discussed above with respect to the first, second and third lights in Table 1.

The user interface 120 also includes audio outputs 125 (e.g., tones, bells, buzzers, integrated speaker, etc.) to communicate various status changes to the user such as lower battery, empty cartridge, etc. The audible feedback can be used in conjunction with or in lieu of the visual outputs 123. The audible feedback may be provided in the forms of clicks, snaps, beeps, rings and buzzers in single or multiple pulse sequences. In one embodiment, a simulated mechanical sound may be prerecorded which replicates the click and/or snap sounds generated by mechanical lockouts and mechanisms of conventional non-powered instruments. This eliminates the need to generate such mechanical sounds through the actual components of the instrument 10 and also avoids the use of beeps and other electronic sounds which are usually associated with other operating room equipment, thereby preventing confusion from extraneous audible feedback. The instrument 10 may include one or more microphones or other voice input devices which can be used to determine the background noise levels and adjust the audible feedback volumes accordingly for clear feedback recognition.

The instrument 10 may also provide for haptic or vibratory feedback through a haptic mechanism (not explicitly shown) within the housing 110. The haptic feedback may be used in conjunction with the auditory and visual feedback or in lieu thereof to avoid confusion with the operating room equipment which relies on audio and visual feedback. The haptic mechanism may be an asynchronous motor that vibrates in a pulsating manner. In one embodiment, the vibrations are at a frequency of about 20 Hz or above, in embodiments from about 20 Hz to about 60 Hz, and providing a displacement having an amplitude of 2 mm or lower, in embodiments from about 0.25 mm to about 2 mm, to limit the vibratory effects from reaching the loading unit 169.

It is also envisioned that user interface 120 may include different colors and/or intensities of text on the screen and/or on the switches for further differentiation between the displayed items. The visual, auditory or haptic feedback can be increased or decreased in intensity. For example, the intensity of the feedback may be used to indicate that the forces on the instrument are becoming excessive.

Figure 5:
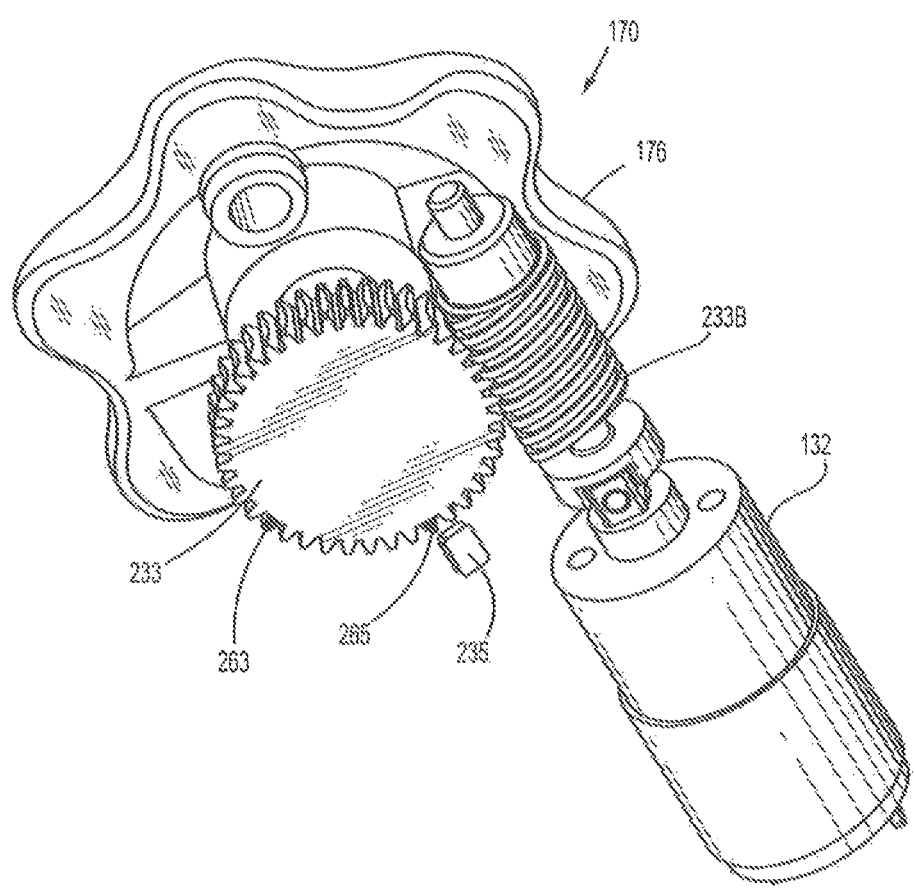
FIG. 5 is a perspective view of an articulation mechanism with parts separated of the powered surgical instrument of FIG. 1.

FIGS. 2, 3 and 4 illustrate an articulation mechanism 170, including an articulation housing 172, a powered articulation switch 174, an articulation motor 132 and a manual articulation knob 176. The articulation switch 174 may be a rocker and/or a slide switch having an arm 174a and 174b on each side of the housing 110 allowing for either right or left hand usage thereof. Translation of the powered articulation switch 174 activates the articulation motor 132. Pivoting of the manual articulation knob 176 will actuate the articulation gear 233 of the articulation mechanism 170 as shown in FIG. 5. Actuation of articulation mechanism 170, by either switch 174 or knob 176, causes the end effector 160 to move from its first position, where longitudinal axis B-B is substantially aligned with longitudinal axis A-A, towards a position in which longitudinal axis B-B is disposed at an angle to longitudinal axis A-A. Preferably, a plurality of articulated positions is achieved. The powered articulation switch 174 may also incorporate similar non-linear speed controls as the clamping mechanism as controlled by the switches 114a and 114b.

Further, the housing 110 includes switch shields 117c and 117d having a wing-like shape and extending from the top surface of the housing 110 over the switch 174. The switch shields 117c or 117d prevent accidental activation of the switch 174 when the instrument 10 is placed down or from physical obstructions during use and require the user to reach below the shield 169 in order to activate the articulation mechanism 170.

Figure 26:
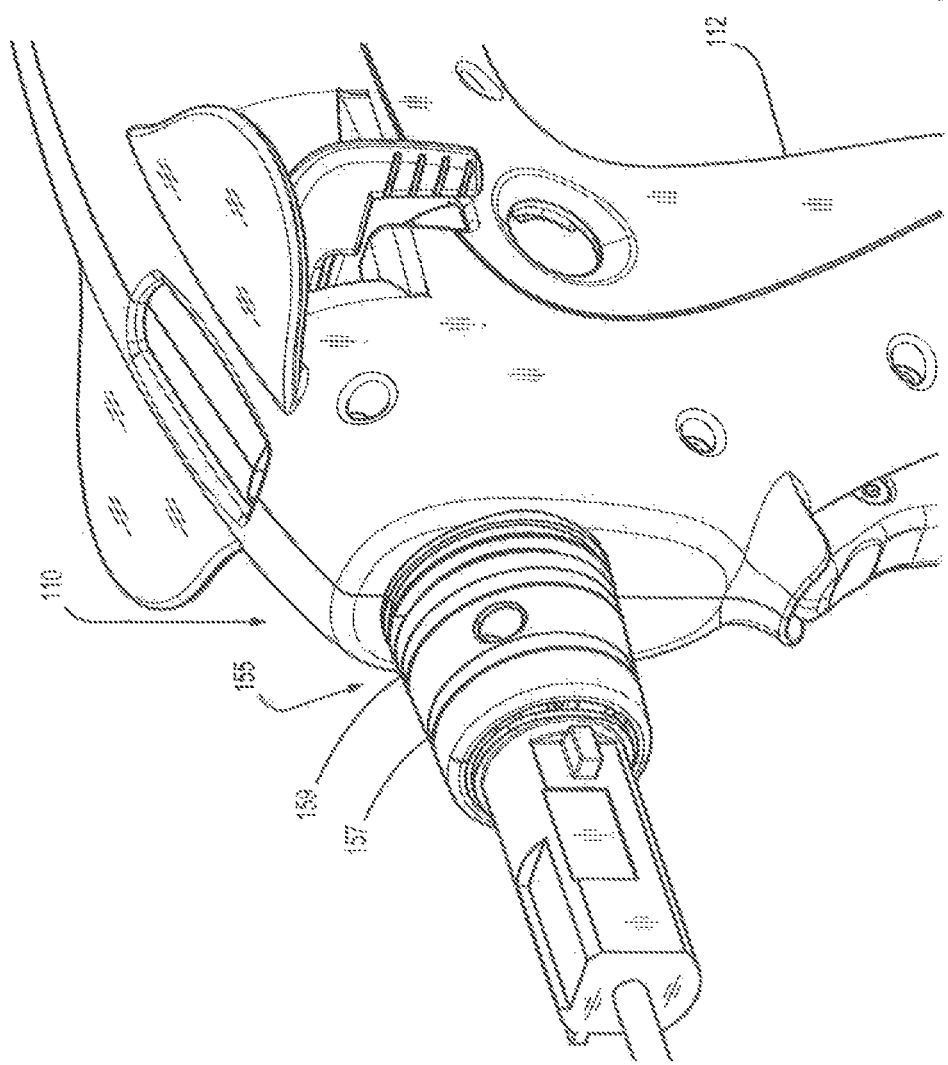
FIG. 26 is a partial perspective view of a nose assembly of the powered surgical instrument in accordance with an embodiment of the present disclosure.

Rotation of a rotation knob 182 about first longitudinal axis A-A causes housing assembly 180 as well as articulation housing 172 and manual articulation knob 176 to rotate about first longitudinal axis A-A, and thus causes corresponding rotation of distal portion 224 of firing rod 220 and end effector 160 about first longitudinal axis A-A. The articulation mechanism 170 is electro-mechanically coupled to first and second conductive rings 157 and 159 which are disposed on housing nose assembly 155 as shown in FIGS. 4 and 26. The conductive rings 157 and 159 may be soldered, glued, press fit, snap fit or crimped onto the nose assembly 155 and are in electrical contact with the power source 400 thereby providing electrical power to the articulation mechanism 170. The nose assembly 155 may be modular (e.g., separate from the housing 110) and may be attached to the housing 110 during assembly to facilitate the aforementioned methods of mounting the rings. The articulation mechanism 170 includes one or more brush and/or spring loaded contacts in contact with the conductive rings 157 and 159 such that as the housing assembly 180 is rotated along with the articulation housing 172 the articulation mechanism 170 is in continuous contact with the conductive rings 157 and 159 thereby receiving electrical power from the power source 400.

Further details of articulation housing 172, powered articulation switch 174, manual articulation knob 176 and providing articulation to end effector 160 are described in detail in U.S. Pat. No. 7,431,188, the contents of which are hereby incorporated by reference in their entirety. It is envisioned that any combinations of limit switches, proximity sensors (e.g., optical and/or ferromagnetic), linear variable displacement transducers or shaft encoders which may be disposed within housing 110, may be utilized to control and/or record an articulation angle of end effector 160 and/or position of the firing rod 220.

FIGS. 4, 5-10 and 11-12 illustrate various internal components of the instrument 10, including a drive motor 200, an internally threaded drive tube 210, and a firing rod 220 having a proximal portion 222 and a distal portion 224. The drive tube 210 is rotatable about drive tube axis C-C extending therethrough. Drive motor 200 is disposed in mechanical cooperation with drive tube 210 and is configured to rotate the drive tube 210 about drive gear axis C-C. In one embodiment, the drive motor 200 may be an electrical motor or a gear motor, which may include gearing incorporated within its housing.

The housing 110 may be formed from two halves 110a and 110b as illustrated in FIG. 3. The two housing portion halves 110a and 110b may be attached to each other using screws at boss locators 111 which align the housing portions 110a and 110b. In one embodiment, ultrasonic welding directors may be used to attach halves 110a and 110b to seal the housing from external contamination. In addition, the housing 110 may be formed from plastic and may include rubber support members applied to the internal surface of the housing 110 via a two-shot molding process. The rubber support members may isolate the vibration of the drive components (e.g., drive motor 200) from the rest of the instrument 10.

The housing halves 110a and 110b may be attached to each other via a thin section of plastic (e.g., a living hinge) that interconnects the halves 110a and 110b allowing the housing 110 to be opened by breaking away the halves 110a and 110b.

In one embodiment, the drive components (e.g., including drive motor 200, drive tube 210, and firing rod 220, etc.) may be mounted on a support plate allowing the drive components to be removed from the housing 110 after the instrument 10 has been used. The support plate mounting in conjunction with the hinged housing halves 110a and 110b provide for reusability and recyclability of specific internal components while limiting contamination thereof.

More particularly, by providing as the support plate a separate, internal, structural member or chassis for the surgical instrument or device, a stronger and higher precision assembly can be produced that is easier to assemble, service, reprocess, reuse or recycle.

Generally, such a structural member or chassis can be much smaller and therefore more accurate dimensionally than an all inclusive handle set cover, e.g., the housing 110 with at least the first and second housing portions 110a and 110b, when produced with similar manufacturing processes. Additional datum planes and locating features can also be designed into the structural member or chassis because of its geometry that is substantially independent of the exterior surface design of the housing 110. The exterior surface geometry of the housing 110 can hinder many aspects of strength and limit numerous aspects of "net shape" molded features.

Higher precision manufacturing methods or processes can also be applied to the structural member or chassis to increase accuracy and decrease required tolerances as compared to the handle set cover. The structural member or chassis may be formed of higher strength/performance materials and/or additional structure as compared to the handle set cover, thereby improving the robustness and fatigue life of at least the operating components contained within the housing 110. That is, the additional precision, alignment and strength can benefit the mechanisms, bearings, gears, clutches, and/or couplings of the surgical instrument 10 or 10', particularly for instruments that are driven and/or powered by electromechanical or pneumatic subsystems that operate under higher linear and/or rotation speeds/loads. Added structure from the structural member or chassis can support extreme or repetitive fatigue loads preventing deformation which can result in misalignment and/or mechanical failures.

Integrating fastener mounting points and/or features into sides of the structural member or chassis allows the housing portions 110a and 110b to be easily removed or replaced while maintaining all of the functional assembly alignments. Components may be assembled from multiple planes of access thereby simplifying the overall assembling, servicing, reprocessing, reusing and recycling of the surgical instrument.

Figure 4A:
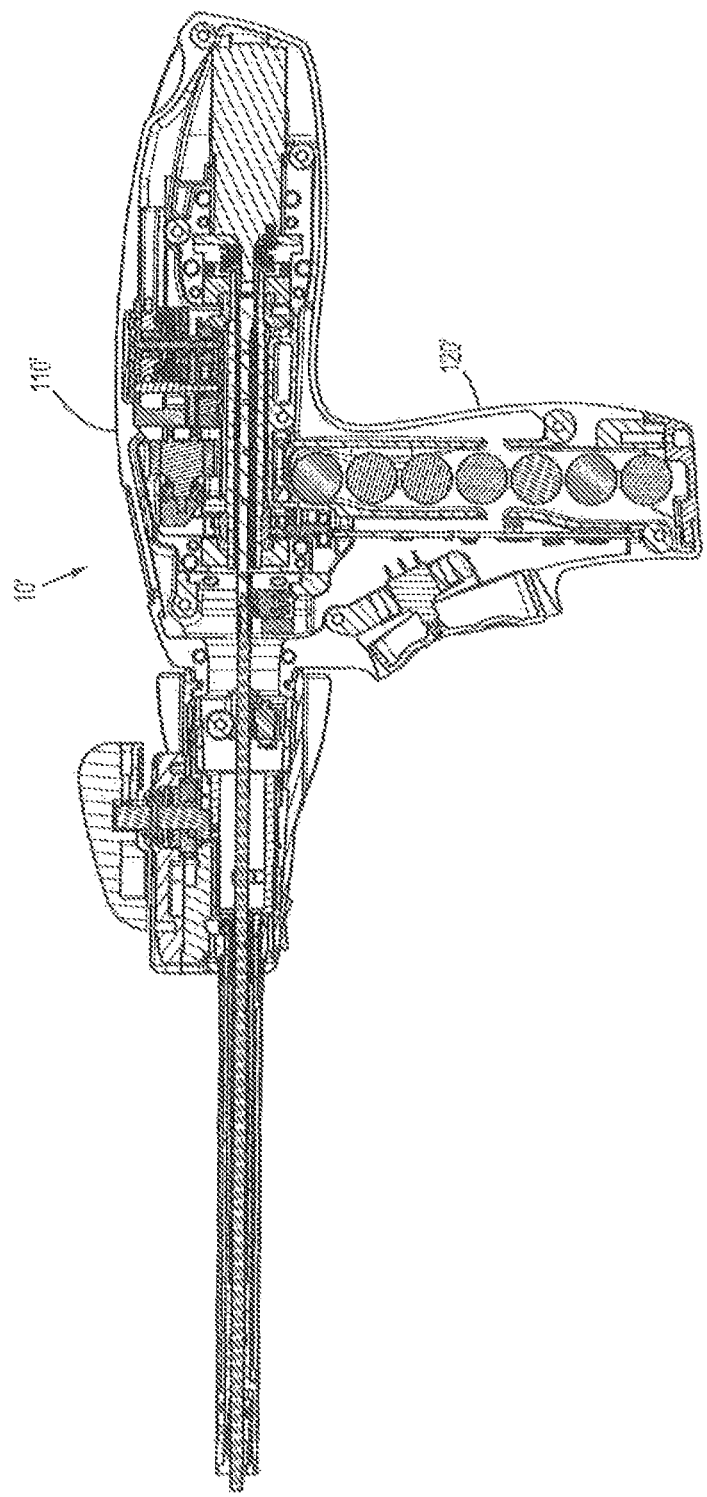
FIG. 4A is a partial view of internal components of the variant of the powered surgical instrument of FIG. 4.

FIG. 4A illustrates the internal components of the variant surgical instrument 10'. FIG. 4A is provided for a general comparison with respect to FIG. 4 and will not be discussed in detail herein.

Returning again to the description of surgical instrument 10 and with reference to FIGS. 4, 5, 6 and 7, a firing rod coupling 190 is illustrated. Firing rod coupling 190 provides a link between the proximal portion 222 and the distal portion 224 of the firing rod 220. Specifically, the firing rod coupling 190 enables rotation of the distal portion 224 of the firing rod 220 with respect to proximal portion 222 of firing rod 220. Thus, firing rod coupling 190 enables proximal portion 222 of firing rod 220 to remain non-rotatable, as discussed below with reference to an alignment plate 350, while allowing rotation of distal portion 224 of firing rod 220 (e.g., upon rotation of rotation knob 182).

Figure 6:
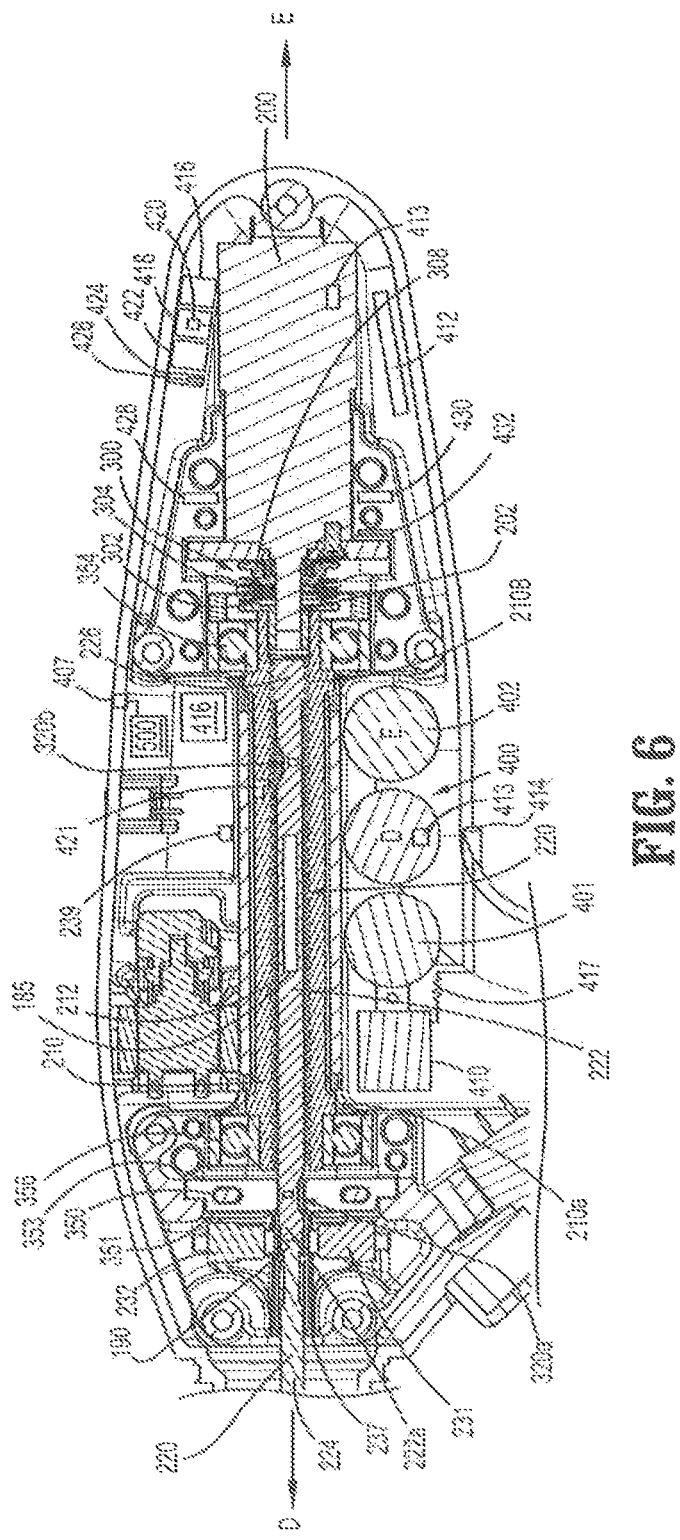
FIG. 6 is a partial cross-sectional view showing internal components of the powered surgical instrument of FIG. 1 disposed in a first position.
Figure 7:
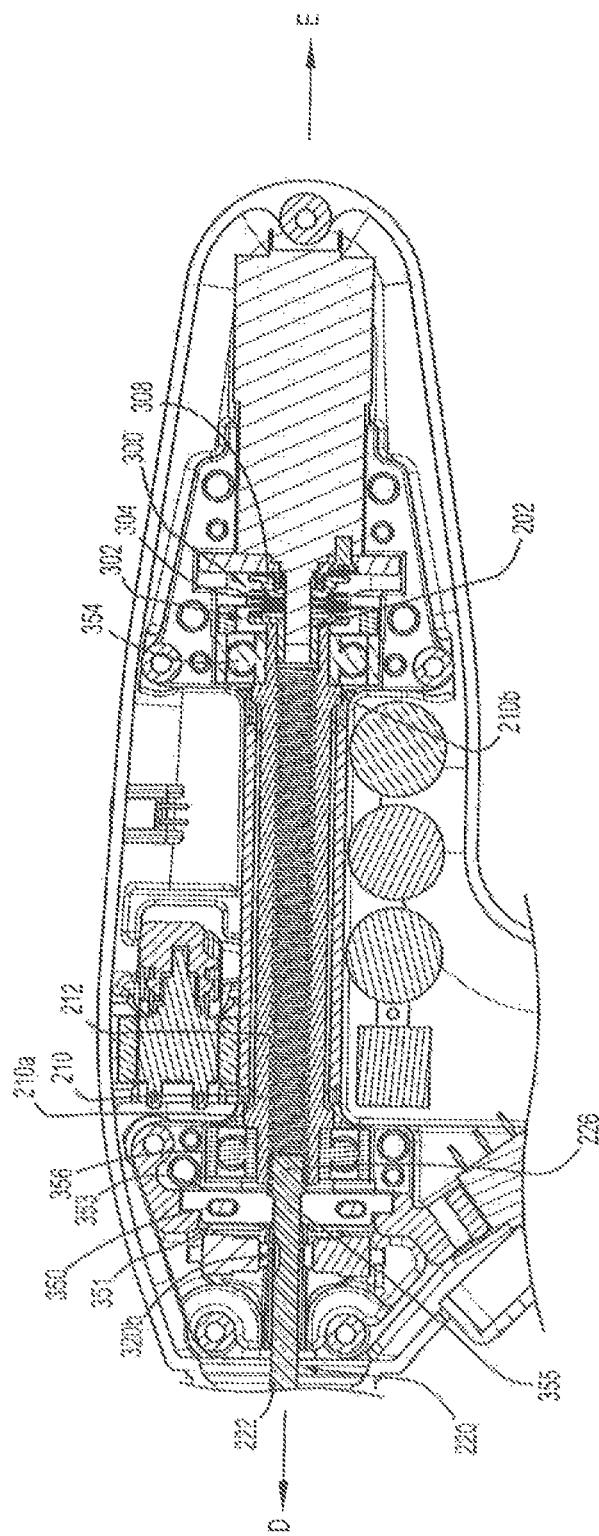
FIG. 7 is a partial cross-sectional view showing internal components of the powered surgical instrument of FIG. 1 disposed in a second position.

With reference to FIGS. 6 and 7, the proximal portion 222 of firing rod 220 includes a threaded portion 226, which extends through an internally-threaded portion 212 of drive tube 210. This relationship between firing rod 220 and drive tube 210 causes firing rod 220 to move distally and/or proximally, in the directions of arrows D and E, along threaded portion 212 of drive tube 210 upon rotation of drive tube 210 in response to the rotation of the drive motor 200. As the drive tube 210 rotates in a first direction (e.g., clockwise), firing rod 220 moves proximally. As illustrated in FIG. 6, the firing rod 220 is disposed at its proximal-most position. As the drive tube 210 rotates in a second direction (e.g., counter-clockwise), firing rod 220 moves distally. As illustrated in FIG. 6, the firing rod 220 is disposed at its distal-most position.

The firing rod 220 is distally and proximally translatable within particular limits. Specifically, a first end 222a of proximal portion 222 of firing rod 220 acts as a mechanical stop in combination with alignment plate 350. That is, upon retraction when firing rod 220 is translated proximally, first end 222a contacts a distal surface 351 of alignment plate 350, thus preventing continued proximal translation of firing rod 220 as shown in FIG. 6. Additionally, threaded portion 226 of the proximal portion 222 acts as a mechanical stop in combination with alignment plate 350. That is, when firing rod 220 is translated distally, the threaded portion 226 contacts a proximal surface 353 of the alignment plate 350, thus preventing further distal translation of firing rod 220 as shown FIG. 7. The alignment plate 350 includes an aperture therethrough, which has a non-round cross-section. The non-round cross-section of the aperture prevents rotation of proximal portion 222 of firing rod 220, thus limiting proximal portion 222 of firing rod 220 to axial translation therethrough. Further, a proximal bearing 354 and a distal bearing 356 are disposed at least partially around drive tube 210 for facilitation of rotation of drive tube 210, while helping align drive tube 210 within housing 110. The drive tube 210 includes a distal radial flange 210a and a proximal radial flange 210b on each end of the drive tube 210 which retain the drive tube 210 between the distal bearing 356 and the proximal bearing 354, respectively.

Figure 9:
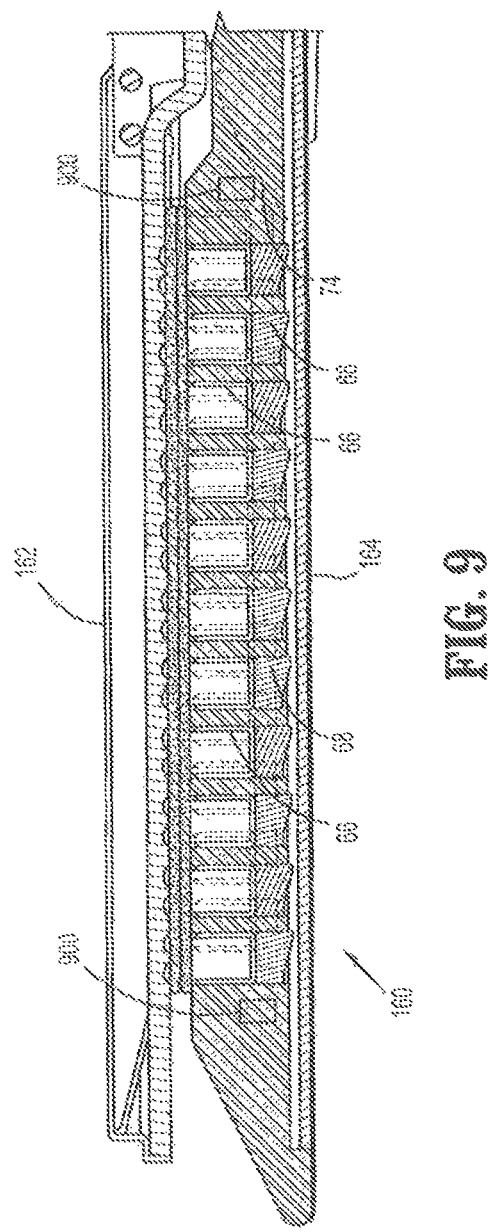
FIG. 9 is a side cross-sectional view of an end effector of the powered surgical instrument of FIG. 1.

Rotation of drive tube 210 in a first direction (e.g., counter-clockwise) corresponds with distal translation of the firing rod 220 which actuates jaw member 162 or 164 (e.g., anvil and cartridge assemblies 162, 164) of the end effector 160 to grasp or clamp tissue held therebetween. Additional distal translation of firing rod 220 ejects surgical fasteners from the end effector 160 to fasten tissue by actuating cam bars and/or an actuation sled 74 (FIG. 9). Further, the firing rod 220 may also be configured to actuate a knife (not explicitly shown) to sever tissue. Proximal translation of firing rod 220 corresponding with rotation of the drive tube 210 in a second direction (e.g., clockwise) actuates the anvil and cartridge assemblies 162, 164 and/or knife to retract or return to corresponding pre-fired positions. Further details of firing and otherwise actuating end effector 160 are described in detail in U.S. Pat. No. 6,953,139, the disclosure of which is hereby incorporated by reference herein.

Figure 8:
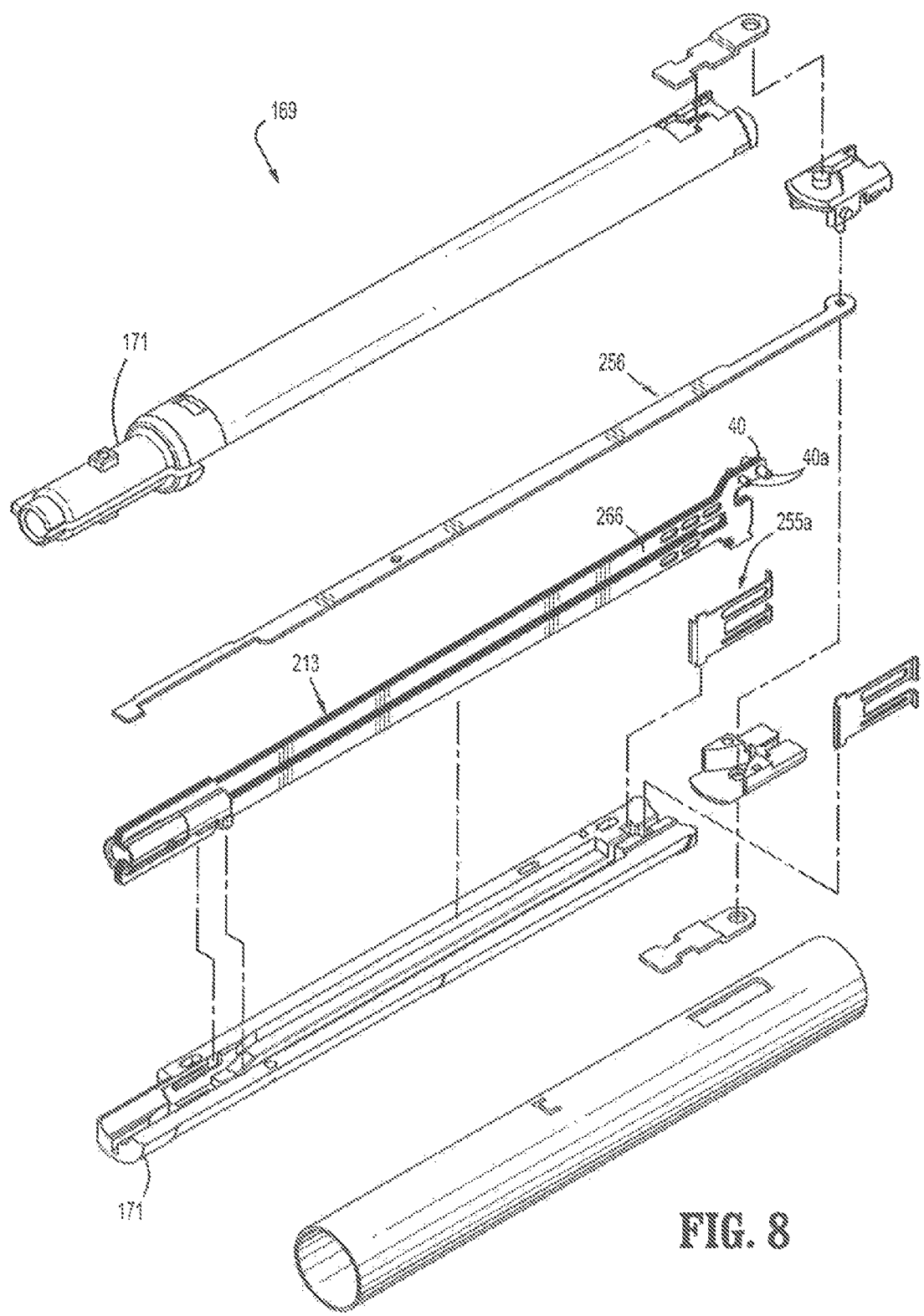
FIG. 8 is a perspective view of the mounting assembly and the proximal body portion of a loading unit with parts separated of the powered surgical instrument of FIG. 1.

FIG. 8 shows a partial exploded view of the loading unit 169. The end effector 160 may be actuated by an axial drive assembly 213 having a drive beam or drive member 266. The distal end of the drive beam 213 may include a knife blade. In addition, the drive beam 213 includes a retention flange 40 having a pair of cam members 40a which engage the anvil and the cartridge assembly 162 and 164 during advancement of the drive beam 213 longitudinally. The drive beam 213 advances an actuation sled 74 longitudinally through the staple cartridge 164. As shown in FIG. 9, the sled 74 has cam wedges for engaging pushers 68 disposed in slots of the cartridge assembly 164, as the sled 74 is advanced. Staples 66 disposed in the slots are driven through tissue and against the anvil assembly 162 by the pushers 66.

Figure 10:
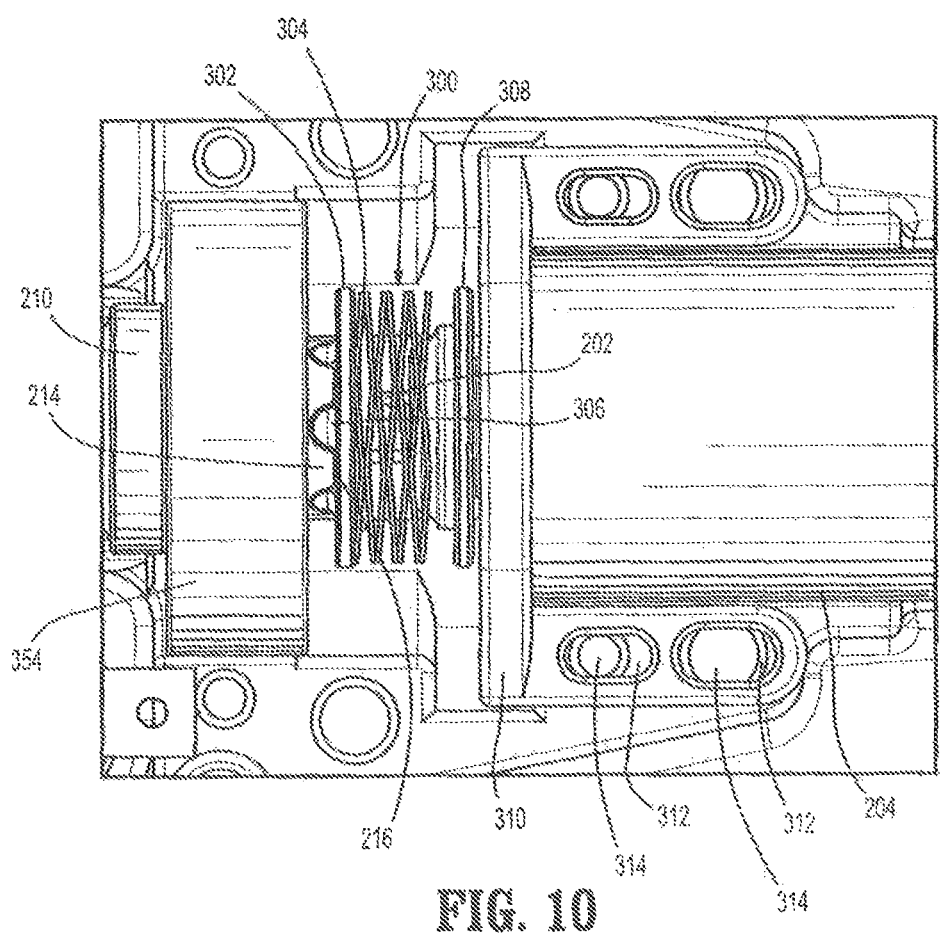
FIG. 10 is a partial enlarged side view showing internal components of the powered surgical instrument of FIG. 1.

With reference to FIG. 10, a drive motor shaft 202 is shown extending from a transmission 204 that is attached to drive motor 200. Drive motor shaft 202 is in mechanical cooperation with clutch 300. Drive motor shaft 202 is rotated by the drive motor 200, thus resulting in rotation of clutch 300. Clutch 300 includes a clutch plate 302 and a spring 304 and is shown having wedged portions 306 disposed on clutch plate 302, which are configured to mate with an interface (e.g., wedges 214) disposed on a proximal face 216 of drive tube 210.

Spring 304 is illustrated between transmission 204 and drive tube 210. Specifically, and in accordance with the embodiment illustrated in FIG. 10, spring 304 is illustrated between clutch face 302 and a clutch washer 308. Additionally, drive motor 200 and transmission 204 are mounted on a motor mount 310. As illustrated in FIG. 8, motor mount 310 is adjustable proximally and distally with respect to housing 110 via slots 312 disposed in motor mount 310 and protrusions 314 disposed on housing 110.

In an embodiment of the disclosure, the clutch 300 is implemented as a slip bi-directional clutch to limit torque and high inertia loads on the drive components. Wedged portions 306 of clutch 300 are configured and arranged to slip with respect to wedges 214 of proximal face 216 of drive tube 210 unless a threshold force is applied to clutch plate 302 via clutch spring 304. Further, when spring 304 applies the threshold force needed for wedged portions 306 and wedges 214 to engage without slipping, drive tube 210 will rotate upon rotation of drive motor 200. It is envisioned that wedged portions 306 and/or wedges 214 are configured to slip in one and/or both directions (i.e., clockwise and/or counter-clockwise) with respect to one another when a firing force is attained on the firing rod 220.

FIG. 10A illustrates a partial enlarged view of the internal components of surgical instrument 10' as described above with respect to FIGS. 2A, 2B and 4A. Again, in a similar manner, FIG. 10A is provided for a general comparison with respect to FIG. 10 and will not be discussed in detail herein. Some of the components that are common with surgical instrument 10 have been identified with the corresponding identification numerals pertaining to surgical instrument 10.

Figure 11:
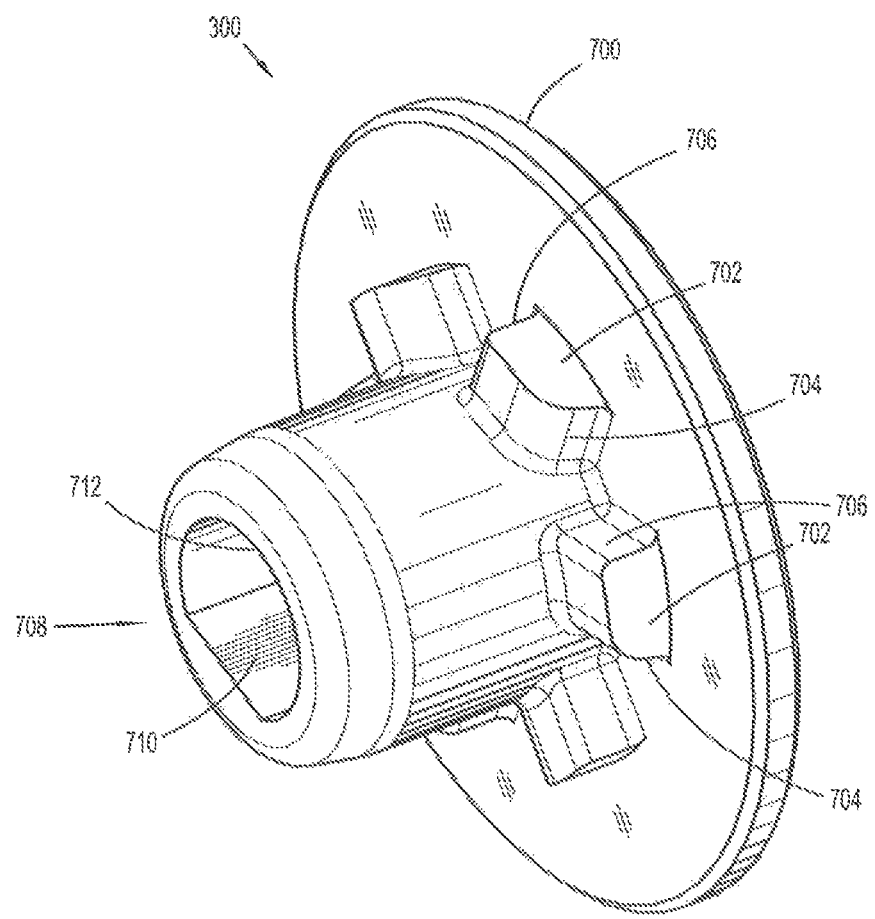
FIG. 11 is a perspective view of a unidirectional clutch plate of the powered surgical instrument of FIG. 1.
Figure 12:
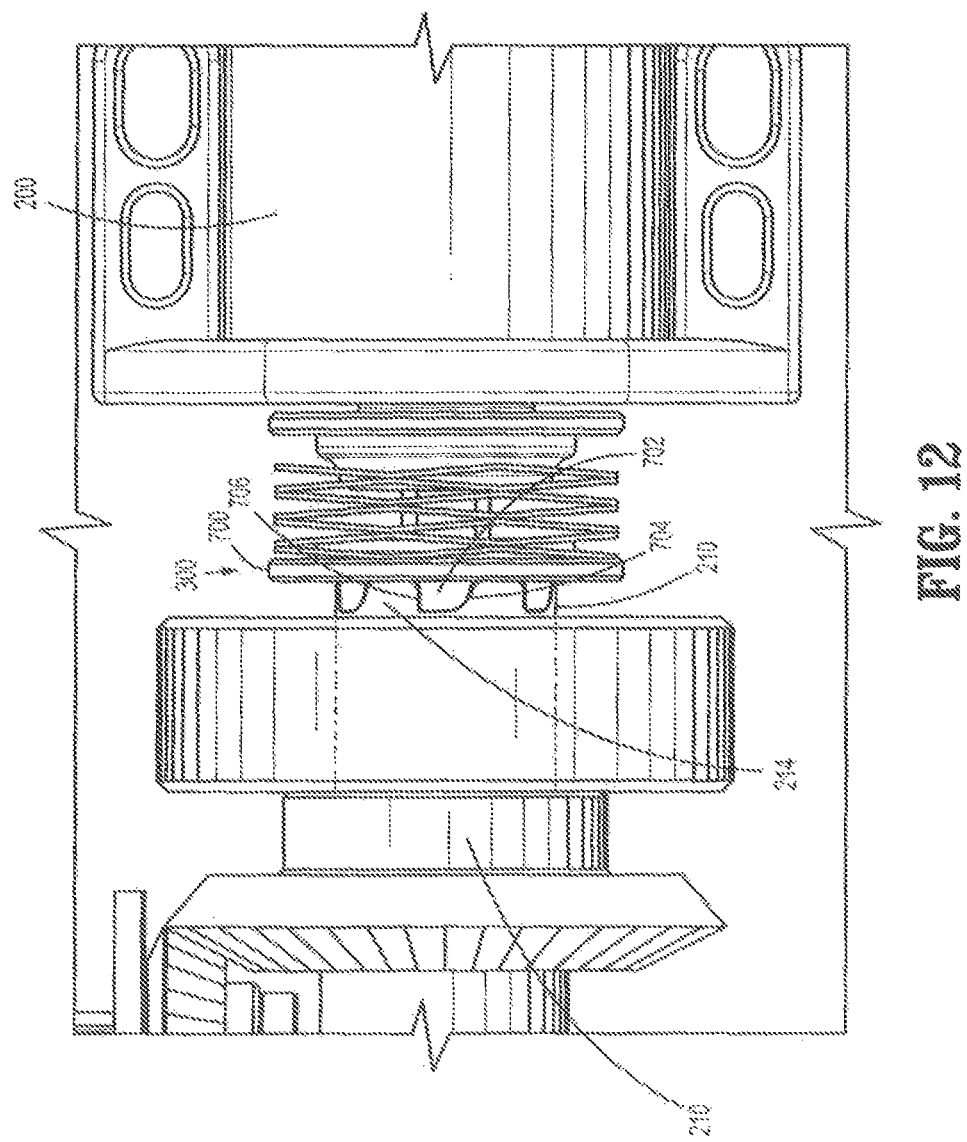
FIG. 12 is a partial enlarged side view showing internal components of the powered surgical instrument of FIG. 1.

Returning again to the description of surgical instrument 10 and with reference to FIGS. 11 and 12, the clutch 300 is shown with a unidirectional clutch plate 700. The clutch plate 700 includes a plurality of wedged portions 702 each having a slip face 704 and a grip face 706. The slip face 704 has a curved edge which engages the wedges 214 of the drive tube 210 up to a predetermined load. The grip face 706 has a flat edge which fully engages the drive tube 210 and prevents slippage. When the clutch plate 700 is rotated in a reverse direction (e.g., counter-clockwise), the grip face 706 of the wedged portions 702 engage the wedges 214 without slipping, providing for full torque from the drive motor 200. This feature helps to assure that jaws 162, 164 will open under retraction during extreme load scenarios. When the clutch plate 700 is rotated in a forward direction (e.g., clockwise), the slip faces 704 of the wedged portions 702 engage the wedges 214 and limit the torque being transferred to the drive tube 210. Thus, if the load being applied to a slip face 704 is over the limit, the clutch 300 slips and the drive tube 210 is not rotated. This can prevent high load damage to the end effector 160 or tissue from the motor and drive components. More specifically, the drive mechanism of the instrument 10 can drive the firing rod 220 in a forward direction with less torque than in reverse. In addition, an electronic clutch may also be used to increase or decrease the motor potential (e.g., driving the drive rod 220 in forward or reverse along with the drive motor 200, drive tube 210, clutch assembly 300, alignment plate 350, and any portion of the firing rod 220) as discussed in more detail below.

It is further envisioned that drive motor shaft 202 includes a D-shaped or non-round cross-section 708, which includes a substantially flat portion 710 and a rounded portion 712. Thus, while drive motor shaft 202 is translatable with respect to clutch plate 700, drive motor shaft 202 will not "slip" with respect to clutch plate 700 upon rotation of drive motor shaft 202. That is, rotation of drive motor shaft 202 will result in a slip-less rotation of clutch plate 700.

The loading unit, in certain embodiments according to the present disclosure, includes an axial drive assembly that cooperates with firing rod 220 to approximate anvil assembly 162 and cartridge assembly 164 of end effector 160, and fire staples from the staple cartridge. The axial drive assembly may include a beam that travels distally through the staple cartridge and may be retracted after the staples have been fired, as discussed above and as disclosed in certain embodiments of U.S. Pat. No. 6,953,139.

With reference to FIG. 4, the instrument 10 includes a power source 400 which may be a rechargeable battery (e.g., lead-based, nickel-based, lithium-ion based, etc.). It is also envisioned that the power source 400 includes at least one disposable battery. The disposable battery may be between about 9 volts and about 30 volts.

The power source 400 includes one or more battery cells 401 depending on the energy and voltage potential needs of the instrument 10. Further, the power source 400 may include one or more ultracapacitors 402 which act as supplemental power storage due to their much higher energy density than conventional capacitors. Ultracapacitors 402 can be used in conjunction with the cells 401 during high energy draw. The ultracapacitors 402 can be used for a burst of power when energy is desired/required more quickly than can be provided solely by the cells 401 (e.g., when clamping thick tissue, rapid firing, clamping, etc.), as cells 401 are typically slow-drain devices from which current cannot be quickly drawn. This configuration can reduce the current load on the cells thereby reducing the number of cells 401. Ultracapacitors 402 can also regulate the system voltage, providing more consistent speed of motor 200 and firing rod 220. It is envisioned that cells 401 can be connected to the ultracapacitors 402 to charge the capacitors.

The power source 400 may be removable along with the drive motor 200 to provide for recycling of these components and reuse of the instrument 10. In another embodiment, the power source 400 may be an external battery pack which is worn on a belt and/or harness by the user and wired to the instrument 10 during use.

The power source 400 is enclosed within an insulating shield 404 which may be formed from an absorbent, flame resistant and retardant material. The shield 404 electrically and thermally isolates components of the instrument 10 from the power source 400. More specifically, the shield 400 prevents heat generated by the power source 400 from heating other components of the instrument 10. In addition, the shield 404 may also be configured to absorb any chemicals or fluids which may leak from the cells 402 during heavy use and/or damage.

The power source 400 may be coupled to a power adapter 406 which is configured to connect to an external power source (e.g., a DC transformer). The external power source may be used to recharge the power source 400 or provide for additional power requirements. The power adapter 406 may also be configured to interface with electrosurgical generators which can then supply power to the instrument 10. In this configuration, the instrument 10 also includes an AC-to-DC power source which converts RF energy from the electrosurgical generators and powers the instrument 10.

In another embodiment the power source 400 is recharged using an inductive charging interface. The power source 400 is coupled to an inductive coil (not explicitly shown) disposed within the proximal portion of the housing 110. Upon being placed within an electromagnetic field, the inductive coil converts the energy into electrical current that is then used to charge the power source 400. The electromagnetic field may be produced by a base station (not explicitly shown) which is configured to interface with the proximal portion of the housing 110, such that the inductive coil is enveloped by the electromagnetic field. This configuration eliminates the need for external contacts and allows for the proximal portion of the housing 110 to seal the power source 400 and the inductive coil within a water-proof environment which prevents exposure to fluids and contamination.

With reference to FIG. 6, the instrument 10 also includes one or more safety circuits such as a discharge circuit 410 and a motor and battery operating module 412. For clarity, wires and other circuit elements interconnecting various electronic components of the instrument 10 are not shown, but such electromechanical connections wires are contemplated by the present disclosure. Certain components of the instrument 10 may communicate wirelessly.

The discharge circuit 410 is coupled to a switch 414 and a resistive load 417 which are in turn coupled to the power source 400. The switch 414 may be a user activated or an automatic (e.g., timer, counter) switch which is activated when the power source 400 needs to be fully discharged for a safe and low temperature disposal (e.g., at the end of surgical procedure). Once the switch 414 is activated, the load 417 is electrically connected to the power source 400 such that the potential of the power source 400 is directed to the load 417. The automatic switch may be a timer or a counter which is automatically activated after a predetermined operational time period or number of uses to discharge the power source 400. The load 417 has a predetermined resistance sufficient to fully and safely discharge all of the cells 401.

The motor and battery operating module 412 is coupled to one or more thermal sensors 413 which determine the temperature within the drive motor 200 and the power source 400 to ensure safe operation of the instrument 10. The sensors may be an ammeter for determining the current draw within the power source 400, a thermistor, a thermopile, a thermocouple, a thermal infrared sensor or the like. Monitoring temperature of these components allows for a determination of the load being placed thereon. The increase in the current flowing through these components causes an increase in temperature therein. The temperature and/or current draw data may then be used to control the power consumption in an efficient manner or assure safe levels of operation.

In order to ensure safe and reliable operation of the instrument 10, it is desirable to ensure that the power source 400 is authentic and/or valid (e.g., conforms to strict quality and safety standards) and operating within a predetermined temperature range. Authentication that the power source 400 is valid minimizes risk of injury to the patient and/or the user due to poor quality.

Figure 13:
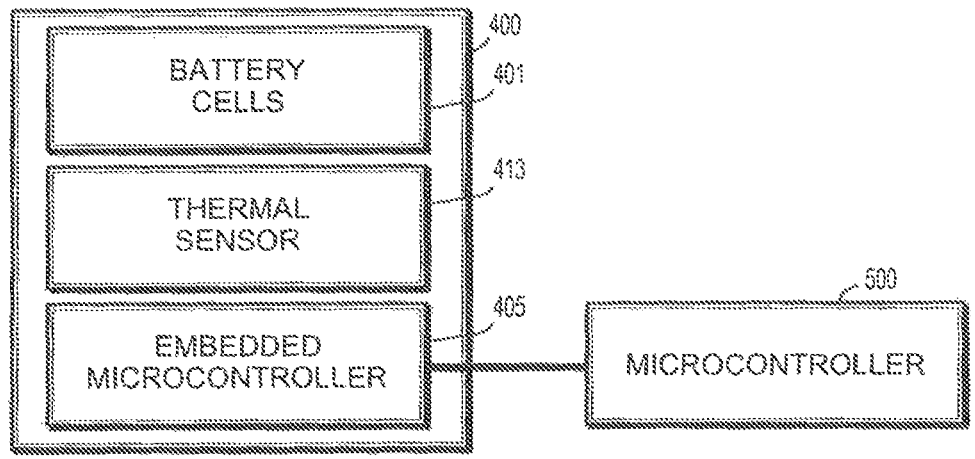
FIG. 13 is a schematic diagram of a power source of the powered surgical instrument of FIG. 1.
Figure 14:
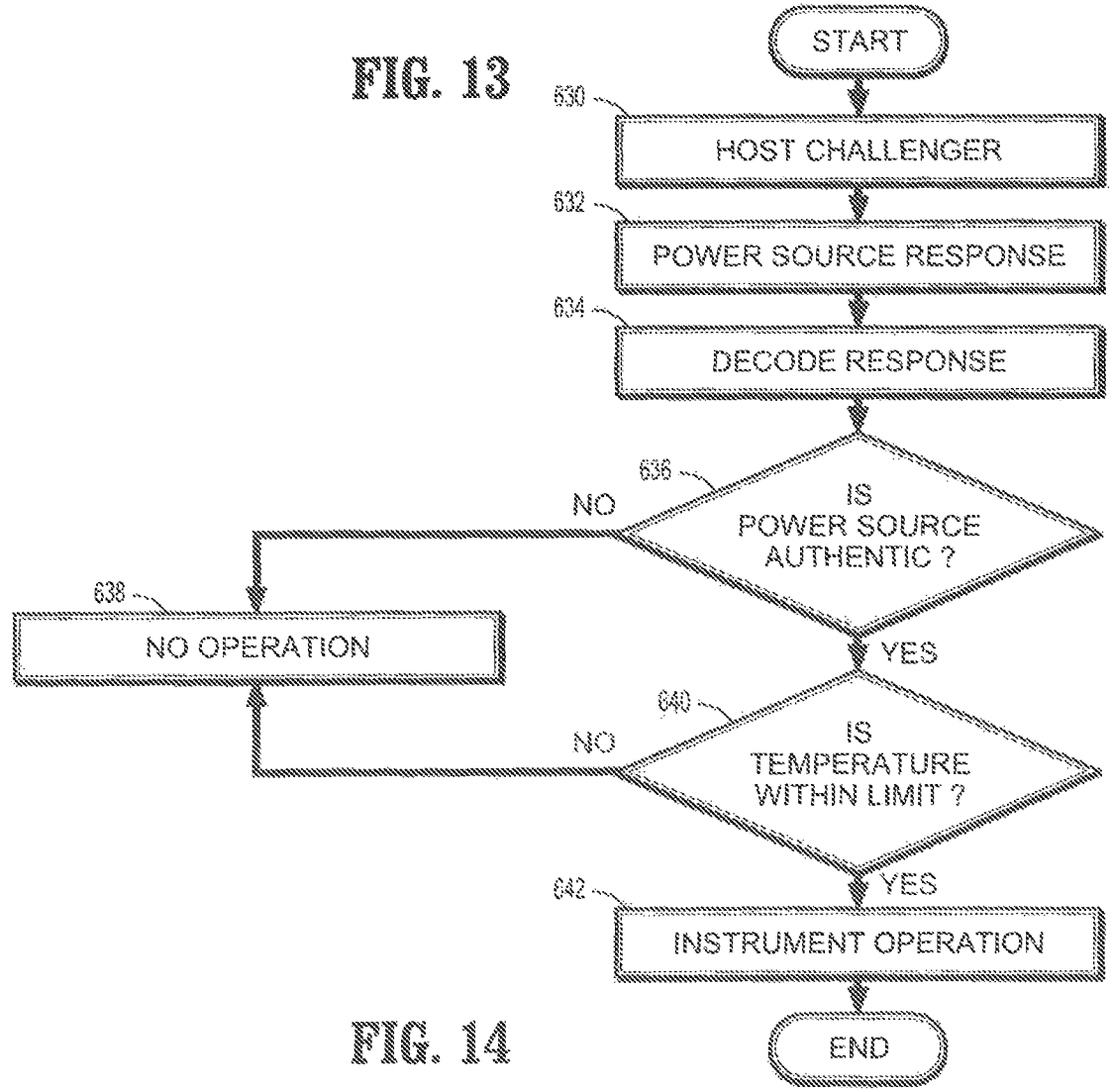
FIG. 14 is a flow chart diagram illustrating a method for authenticating the power source of the powered surgical instrument of FIG. 1.

With reference to FIG. 13, the power source 400 is shown having one or more battery cells 401, the thermal sensor 413 and an embedded microcontroller 405 coupled thereto. The microcontroller 405 is coupled through wired and/or wireless communication protocols to microcontroller 500 (FIGS. 6, 13 and 20) of the instrument 10 to authenticate the power source 400. In one embodiment, the thermal sensor 413 can be coupled directly to the microcontroller 500 instead of being coupled to the embedded microcontroller 405. The thermal sensor 413 may be a thermistor, a thermopile, a thermocouple, a thermal infrared sensor, a resistance temperature detector, linear active thermistor, temperature-responsive color changing strips, bimetallic contact switches, or the like. The thermal sensor 413 reports the measured temperature to the microcontroller 405 and/or microcontroller 500.

The embedded microcontroller 405 executes a so-called challenge-response authentication algorithm with the microcontroller 500 which is illustrated in FIG. 13. In step 630, the power source 400 is connected to the instrument 10 and the instrument 10 is switched on. The microcontroller 500 sends a challenge request to the embedded microcontroller 405. In addition the microcontroller 500 may request the battery temperature from microcontroller 405 which receives it from thermal sensor 413. In step 632, the microcontroller 405 interprets the challenge request and generates a response as a reply to the request. The response may include an identifier, such as a unique serial number stored in a radio frequency identification tag or in memory of the microcontroller 405, a unique electrical measurable value of the power source 400 (e.g., resistance, capacitance, inductance, etc.). In addition, the response includes the temperature measured by the thermal sensor 413.

In step 634, the microcontroller 500 decodes the response to obtain the identifier and the measured temperature. In step 636, the microcontroller 500 determines if the power source 400 is authentic based on the identifier, by comparing the identifier against a pre-approved list of authentic identifiers. If the identifier is not valid, the instrument 10 is not going to operate and displays an error code or a "failure to authenticate battery" message via the user interface 120. If the identifier is valid, the process proceeds to step 640 where the measured temperature is analyzed to determine if the measurement is within a predetermined operating range. If the temperature is outside the limit, the instrument 10 also displays an error message. Thus, if the temperature is within the predetermined limit and the identifier is valid, in step 642, the instrument commences operation, which may include providing a "battery authenticated" message to the user.

Referring back to FIGS. 4 and 6 a plurality of sensors for providing feedback information relating to the function of the instrument 10 are illustrated. Any combination of sensors may be disposed within the instrument 10 to determine its operating stage, such as, staple cartridge load detection as well as status thereof, articulation, clamping, rotation, stapling, cutting and retracting, or the like. The sensors can be actuated by rotational encoders, proximity, displacement or contact of various internal components of the instrument 10 (e.g., firing rod 220, drive motor 200, etc.).

In the illustrated embodiments, the sensors can be rheostats (e.g., variable resistance devices), current monitors, conductive sensors, capacitive sensors, inductive sensors, thermal-based sensors, limit actuated switches, multiple position switch circuits, pressure transducers, linear and/or rotary variable displacement transducers, linear and/or rotary potentiometers, optical encoders, ferromagnetic sensors, Hall Effect sensors, or proximity switches. The sensors measure rotation, velocity, acceleration, deceleration, linear and/or angular displacement, detection of mechanical limits (e.g., stops), etc. This is attained by implementing multiple indicators arranged in either linear or rotational arrays on the mechanical drive components of the instrument 10. The sensors then transmit the measurements to the microcontroller 500 which determines the operating status of the instrument 10. In addition, the microcontroller 500 also adjusts the motor speed or torque of the instrument 10 based on the measured feedback.

In embodiments where the clutch 300 is implemented as a slip clutch as shown in FIGS. 11 and 12, linear displacement sensors (e.g., linear displacement sensor 237 in FIG. 4) are positioned distally of the clutch 300 to provide accurate measurements. In this configuration, slippage of the clutch 300 does not affect the position, velocity and acceleration measurements recorded by the sensors.

With reference to FIG. 4, a load switch 230 is disposed within the housing nose assembly 155. The switch 230 is connected in series with the power source 400, preventing activation of the microcontroller 500 and instrument 10 unless the loading unit 169 is properly loaded into the instrument 10. If the loading unit 169 is not loaded into the instrument 10, the connection to the power source 400 is open, thereby preventing use of any electronic or electric components of the instrument 10. This prevents any possible current draw from the power source 400 allowing the power source 400 to maintain a maximum potential over its specified shelf life.

Figure 18:
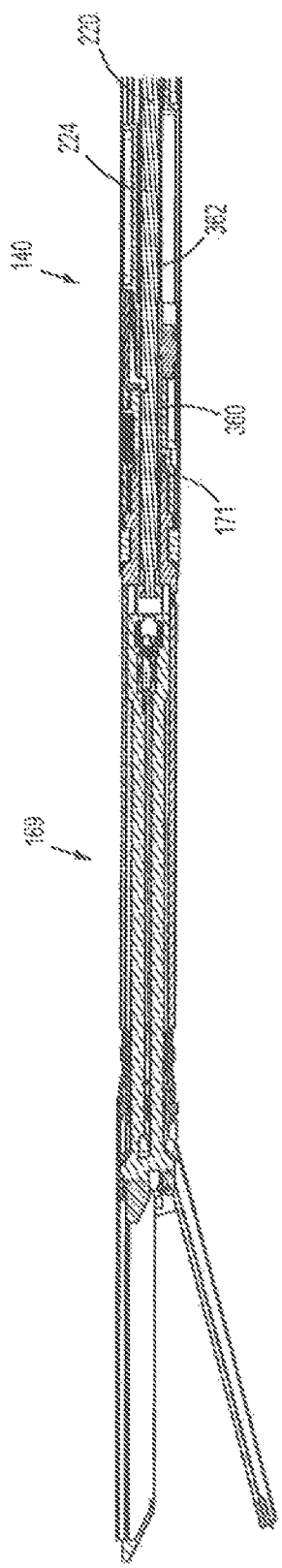
FIG. 18 is a side cross-sectional view of the end effector of the powered surgical instrument of FIG. 1.
Figure 19:
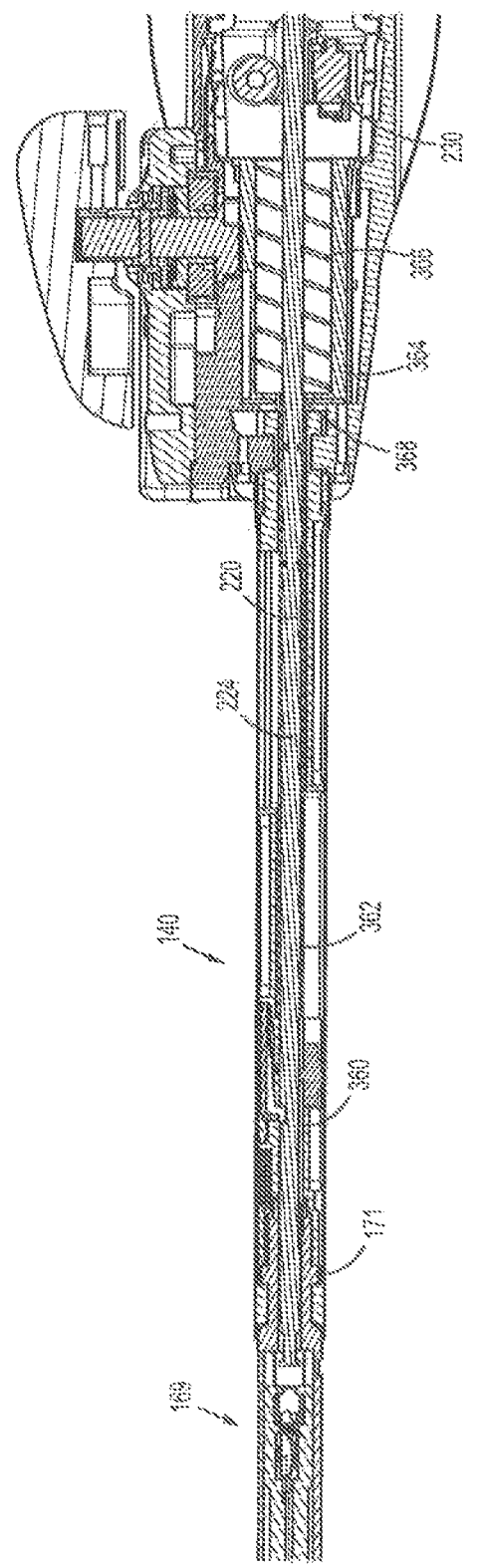
FIG. 19 is a side cross-sectional view of the powered surgical instrument of FIG. 1.

Thus, the switch 230 acts as a so-called "power-on" switch which prevents false activation of the instrument 10 since the switch is inaccessible to external manipulation and can only be activated by the insertion of the loading unit 169. In FIGS. 18 and 19, the switch 230 is activated by displacement of sensor plate 360 to the sensor tube 362 which displaces the sensor cap 364 as the loading unit 169 is inserted into the endoscopic portion 140. Once the switch 230 is activated, the power from the power source 400 is supplied to the electronic components (e.g., sensors, microcontroller 500, etc.) of the instrument 10 providing the user with access to the user interface 120 and other inputs/outputs. This also activates the visual outputs 123 to light up according to the light combination indicative of a properly loaded loading unit 169 wherein all the lights are off as described in Table 1.

More specifically, as shown in FIGS. 18 and 19, the endoscopic portion 140 includes a sensor plate 360 therein which is in mechanical contact with a sensor tube also disposed within the endoscopic portion 140 and around the distal portion 224 of firing rod 220. The distal portion 224 of the firing rod 220 passes through an opening 368 at a distal end of a sensor cap 364. The sensor cap 364 includes a spring and abuts the switch 230. This allows the sensor cap 364 to be biased against the sensor tube 362 which rests on the distal end of the sensor cap 364 without passing through the opening 368. Biasing of the sensor tube 362 then pushes out the sensor plate 360 accordingly.

When the loading unit 169 is loaded into the endoscopic portion 140, the proximal portion 171 abuts the sensor plate 360 and displaces the plate 360 in a proximal direction. The sensor plate 360 then pushes the sensor tube 362 in the proximal direction which then applies pressure on the sensor cap 364 thereby compressing the spring 366 and activating the switch 230 denoting that the loading unit 169 has been properly inserted.

Once the loading unit 169 is inserted into the endoscopic portion, the switch 230 also determines whether the loading unit 169 is loaded correctly based on the position thereof. If the loading unit 169 is improperly loaded, no switches are activated and an error code is relayed to the user via the user interface 120 (e.g., all the lights are off as described in Table 1). If the loading unit 169 has already been fired, any mechanical lockouts have been previously activated or the staple cartridge has been used, the instrument 10 relays the error via the user interface 120, e.g., the first light 123a is flashing.

In one embodiment, a second lock-out switch (not shown) coupled to the microcontroller 500 (see FIG. 6) may be implemented in the instrument 10 as a bioimpedance, capacitance or pressure sensor disposed on the top surface of, or within, the handle portion 112 configured to be activated when the user grasps the instrument 10. Thus, unless the instrument 10 is grasped properly, all switches are disabled.

In one embodiment, with reference to FIG. 6, the instrument 10 includes a position calculator 416 for determining and outputting current linear position of the firing rod 220. The position calculator 416 is electrically connected to a linear displacement sensor 237 and a rotation speed detecting apparatus 418 is coupled to the drive motor 200. The apparatus 418 includes an encoder 420 coupled to the motor for producing two or more encoder pulse signals in response to the rotation of the drive motor 200. The encoder 420 transmits the pulse signals to the apparatus 418 which then determines the rotational speed of the drive motor 200. The position calculator 416 thereafter determines the linear speed and position of the firing rod based on the rotational speed of the drive motor 200 since the rotation speed is directly proportional to the linear speed of the firing rod 220. The position calculator 416 and the speed calculator 422 are coupled to the microcontroller 500 which controls the drive motor 200 in response to the sensed feedback form the calculators 416 and 422. This configuration is discussed in more detail below with respect to FIG. 20.

The instrument 10 includes first and second indicators 320a, 320b disposed on the firing rod 220, which determine the limits of firing rod 220. The linear displacement sensor 237 determines the location of firing rod 220 with respect to drive tube 210 and/or housing 110. For instance, a limit switch may be activated (e.g., shaft start position sensor 231 and clamp position sensor 232) by sensing first and second indicators 320a and/or 320b (e.g., bumps, grooves, indentations, etc.) passing thereby to determine the limits of firing rod 220 and mode of the instrument 10 (e.g., clamping, grasping, firing, sealing, cutting, retracting, etc.). Further, the feedback received from first and second indicators 320a, 320b may be used to determine when firing rod 220 should stop its axial movement (e.g., when drive motor 200 should cease) depending on the size of the particular loading unit attached thereto. The first indicator 320a may also be used to calibrate the instrument 10 as will be described below with reference to FIG. 44.

More specifically, as the firing rod 220 is moved in the distal direction from its resting (e.g., initial) position, the first actuation of the position sensor 231 is activated by the first indicator 320a which denotes that operation of the instrument 10 has commenced. As the operation continues, the firing rod 220 is moved further distally to initiate clamping, which moves first indicator 320a to interface with clamp position sensor 232. Further advancement of the firing rod 220 moves the second indicator 320b to interface with the position sensor 232 which indicates that the instrument 10 has been fired.

As discussed above, the position calculator 416 is coupled to a linear displacement sensor 237 disposed adjacent to the firing rod 220. In one embodiment, the linear displacement sensor 237 may be a magnetic sensor. The firing rod 220 may include magnets or magnetic features. The magnetic sensor may be a ferromagnetic sensor or a Hall Effect sensor which is configured to detect changes in a magnetic field. As the firing rod 220 is translated linearly due to the rotation of the drive motor 200, the change in the magnetic field in response to the translation motion is registered by the magnetic sensor. The magnetic sensor transmits data relating to the changes in the magnetic field to the position calculator 416 which then determines the position of the firing rod 220 as a function of the magnetic field data.

In one embodiment, a select portion of the firing rod 220 may be a magnetic material, such as the threads of the internally-threaded portion 212 or other notches (e.g., indicators 320a and/or 320b) disposed on the firing rod 220 may include or be made from a magnetic material. This allows for correlation of the cyclical variations in the magnetic field with each discrete translation of the threads as the magnetized portions of the firing rod 220 are linearly translated. The position calculator 416 thereafter determines the distance and the position of the firing rod 220 by summing the number of cyclical changes in the magnetic field and multiplies the sum by a predetermined distance between the threads and/or notches.

In one embodiment, the linear displacement sensor 237 may be a potentiometer or a rheostat. The firing rod 220 includes a contact (e.g., wiper terminal) disposed in electromechanical contact with the linear displacement sensor 237. The contact slides along the surface of the linear displacement sensor 237 as the firing rod 220 is moved in the distal direction by the drive motor 200. As the contact slides across the potentiometer and/or the rheostat, the voltage of the potentiometer and the resistance of the rheostat vary accordingly. Thus, the variation in voltage and resistance is transmitted to the position calculator 416 which then extrapolates the distance traveled by the firing rod 220 and/or the firing rod coupling 190 and the position thereof.

In one embodiment, the position calculator 416 is coupled to one or more switches 421 which are actuated by the threads of the internally-threaded portion 212 or the indicators 320a and/or 320b as the firing rod 220 and the firing rod coupling 190 are moved in the distal direction. The position calculator 416 counts the number of threads which activated the switch 421 and then multiplies the number by a predetermined distance between the threads or the indicators 320a and/or 320b.

The instrument 10 also includes a speed calculator 422 which determines the current speed of a linearly moving firing rod 220 and/or the torque being provided by the drive motor 200. The speed calculator 422 is connected to the linear displacement sensor 237 which allows the speed calculator 422 to determine the speed of the firing rod 220 based on the rate of change of the displacement thereof.

The speed calculator 422 is coupled to the rotation speed detecting apparatus 424 which includes the encoder 426. The encoder 426 transmits the pulses correlating to the rotation of the drive motor 200 which the speed calculator 422 then uses to calculate the linear speed of the firing rod 220. In another embodiment, the speed calculator 422 is coupled to a rotational sensor 239 which detects the rotation of the drive tube 210, thus measuring the rate of rotation of the drive tube 210 which allows for determination of the linear velocity of the firing rod 220.

The speed calculator 422 is also coupled to a voltage sensor 428 which measures the back electromotive force ("EMF") induced in the drive motor 200. The back EMF voltage of the drive motor 200 is directly proportional to the rotational speed of the drive motor 200 which, as discussed above, is used to determine the linear speed of the firing rod 220.

Monitoring of the speed of the drive motor 200 can also be accomplished by measuring the voltage across the terminals thereof under constant current conditions. An increase in a load of the drive motor 200 yields a decrease in the voltage applied at the motor terminals, which is directly related to the decrease in the speed of the motor. Thus, measuring the voltage across the drive motor 200 provides for determining the load being placed thereon. In addition, by monitoring the change of the voltage over time (dV/dt), the microprocessor 500 can detect a quick drop in voltage which correlates to a large change in the load or an increase in temperature of the drive motor 200 and/or the power source 400.

In a further embodiment, the speed calculator 422 is coupled to a current sensor 430 (e.g., an ammeter). The current sensor 430 is in electrical communication with a shunt resistor 432 which is coupled to the drive motor 200. The current sensor 430 measures the current being drawn by the drive motor 200 by measuring the voltage drop across the resistor 432. Since the voltage applied to power the drive motor 200 is proportional to the rotational speed of the drive motor 200 and, hence, the linear speed of the firing rod 220, the speed calculator 422 determines the speed of the firing rod 220 based on the voltage potential of the drive motor 200.

The current sensor 430 may also be coupled to the power source 400 to determine the current draw thereof which allows for analysis of the load on the end effector 160. This may be indicative of the tissue type being stapled since various tissue have different tensile properties which affect the load being exerted on the instrument 10 and the power source 400 and/or the motor 200.

The speed calculator 422 may also be coupled to a second voltage sensor (not explicitly shown) for determining the voltage within the power source 400 thereby calculating the power draw directly from the source. In addition, the change in current over time (dI/dt) can be monitored to detect quick spikes in the measurements which correspond to a large increase in applied torque by the drive motor 200. Thus, the current sensor 430 may be used to determine the torque and the load of the drive motor 200.

In addition, the velocity of the firing rod 220 as measured by the speed calculator 422 may be then compared to the current draw of the drive motor 200 to determine whether the drive motor 200 is operating properly. Namely, if the current draw is not commensurate (e.g., large) with the velocity (e.g., low) of the firing rod 220 then the motor 200 is malfunctioning (e.g., locked, stalled, etc.). If a stall situation is detected, or the current draw exceeds predetermined limits, the position calculator 416 then determines whether the firing rod 220 is at a mechanical stop. If this is the case, then the microcontroller 500 can shut down the drive motor 200 or enters a pulse and/or pause mode (e.g., discontinuous supply of power to the drive motor 200) to prevent damage to the motor 200, battery or power source 400, and microcontroller 500, to unlock the instrument 10 and to retract the firing rod 220.

In one embodiment, the speed calculator 422 compares the rotation speed of the drive tube 210 as detected by the rotation sensor 239 and that of the drive motor 200 based on the measurements from and the rotation speed detecting apparatus 424. This comparison allows the speed calculator 422 to determine whether there is clutch activation problem (e.g., slippage) if there is a discrepancy between the rotation of the clutch 300 and that of the drive tube 210. If slippage is detected, the position calculator 416 then determines whether the firing rod 220 is at a mechanical stop. If this is the case, then the microcontroller 500 can shut down the instrument 10 or enter a pulse and/or pause mode (e.g., discontinuous supply of power to the drive motor 200), or retract the firing rod 220.

In addition to linear and/or rotational displacement of the firing rod 220 and other drive components, the instrument 10 also includes sensors adapted to detect articulation of the end effector 160. With reference to FIG. 4, the instrument 10 includes a rotation sensor 241 adapted to indicate the start position, the rotational direction and the angular displacement of the rotating housing assembly 180 at the start of the procedure as detected by the shaft start position sensor 231. The rotation sensor 241 operates by counting the number of indicators disposed on the inner surface of the rotation knob 182 by which the rotation knob 182 has been rotated. The count is then transmitted to the microcontroller 500 which then determines the rotational position of the endoscopic portion 142. This can be communicated wirelessly or through an electrical connection on the endoscopic portion and wires to the microcontroller 500.

The instrument 10 also includes an articulation sensor 235 which determines articulation of the end effector 160. The articulation sensor 235 counts the number of features 263 disposed on the articulation gear 233 by which the articulation knob 176 has been rotated from its 0° position, namely the center position of the articulation knob 176 and, hence, of the end effector 160 as shown in FIG. 5. The 0° position and can be designated by a central unique indicator 265 also disposed on the articulation gear 233 which corresponds with the first position of the end effector 160, where longitudinal axis B-B is substantially aligned with longitudinal axis A-A. The count is then transmitted to the microcontroller 500 which then determines the articulation position of the end effector 160 and reports the articulation angle via the interface 120. The features can include protrusions, magnetic material, transmitters, etc.

In addition, the articulation angle can be used for the so-called "auto stop" mode. During this operational mode, the instrument 10 automatically stops the articulation of the end effector 160 when the end effector 160 is at its central first position. Namely, as the end effector 160 is articulated from a position in which longitudinal axis B-B is disposed at an angle to longitudinal axis A-A towards the first position, the articulation is stopped when the longitudinal axis B-B is substantially aligned with longitudinal axis A-A. This position is detected by the articulation sensor 235 based on the central indicator. This mode allows the endoscopic portion 140 to be extracted without the user having to manually align the end effector 160.

With reference to FIG. 1, the present disclosure provides a loading unit identification system 440 which allows the instrument 10 to identify the loading unit 169 and to determine operational status thereof. The identification system 440 provides information to the instrument 10 on staple size, cartridge length, type of the loading unit 169, status of cartridge, proper engagement, and the like. This information allows the instrument to adjust clamping forces, speed of clamping and firing and end of stroke for various length staple cartridges.

The loading unit identification system 440 may also be adapted to determine and communicate to the instrument 10 (e.g., a control system 501 shown in FIG. 20) various information, including the speed, power, torque, clamping, travel length and/or strength limitations for operating the particular end effector 160. The control system 501 may also determine the operational mode and adjust the voltage, clutch spring loading and stop points for travel of the components. More specifically, the identification system may include a component (e.g., a microchip, emitter or transmitter) disposed in the end effector 160 that communicates (e.g., wirelessly, via infrared signals, etc.) with the control system 501, or a receiver therein. It is also envisioned that a signal may be sent via firing rod 220, such that firing rod 220 functions as a conduit for communications between the control system 501 and end effector 160. In another embodiment, the signals can be sent through an intermediate interface, such as a feedback controller 603 (FIGS. 21-23).

By way of example, the sensors discussed above may be used to determine if the staples have been fired from the staple cartridge, whether they have been fully fired, whether and the extent to which the beam has been retracted proximally through the staple cartridge, and other information regarding the operation of the loading unit. In certain embodiments of the present disclosure, the loading unit incorporates components for identifying the type of loading unit, and/or staple cartridge loaded on the instrument 10, including magnetic, optical, infra-red, cellular, radio frequency or conductive identification chips. The type of loading unit and/or staple cartridge may be received by an associated receiver within the control system 501, or an external device in the operating room for providing feedback, control and/or inventory analysis.

Information can be transmitted to the instrument 10 via a variety of communication protocols (e.g., wired or wireless) between the loading unit 169 and the instrument 10. The information can be stored within the loading unit 169 in a microcontroller, microprocessor, non-volatile memory, radio frequency identification tags, and identifiers of various types such as optical, color, displacement, magnetic, electrical, binary and/or gray coding (e.g., conductance, resistance, capacitance, impedance).

In one embodiment, the loading unit 169 and the instrument 10 include corresponding wireless transceivers, an identifier 442 and an interrogator 444, respectively. The identifier 442 includes memory or may be coupled to a microcontroller for storing various identification and status information regarding the loading unit 169. Once the loading unit 169 is coupled to the instrument 10, the instrument 10 interrogates the identifier 442 via the interrogator 444 for an identifying code. In response to the interrogatory, the identifier 442 replies with the identifying code corresponding to the loading unit 169. During operation, once identification has occurred, the identifier 442 is configured to provide the instrument 10 with updates as to the status of the loading unit 169 (e.g., mechanical and/or electrical malfunction, position, articulation, etc.).

The identifier 442 and the interrogator 444 are configured to communicate with each other using one or more communication protocols, such as Bluetooth®, ANT3®, KNX®, ZWave®, X10® Wireless USB®, IrDA®, Nanonet®, Tiny OS®, ZigBee®, 802.11 IEEE, and other radio, infrared, UHF, VHF communications or the like. In one embodiment, the transceiver 400 may be a radio frequency identification (RFID) tag, either active or passive, depending on the interrogator capabilities of the transceiver 402.

Figure 15A:
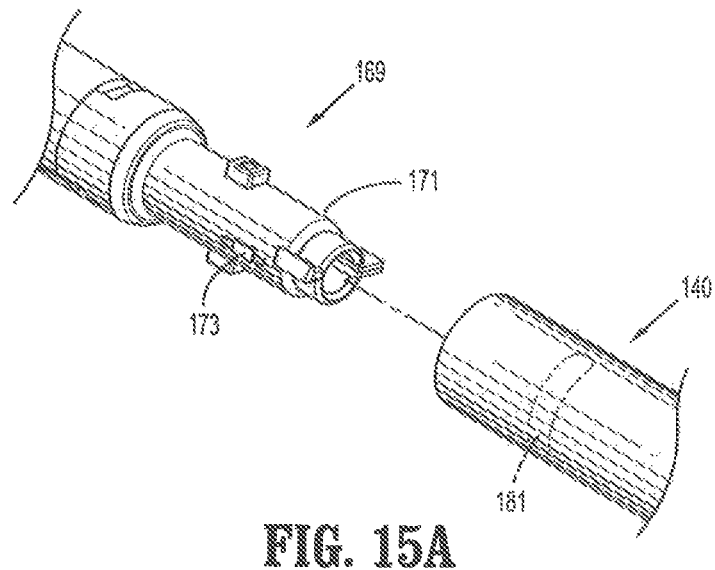
FIGS. 15A-B are partial perspective rear views of a loading unit of the powered surgical instrument of FIG. 1.
Figure 15B:
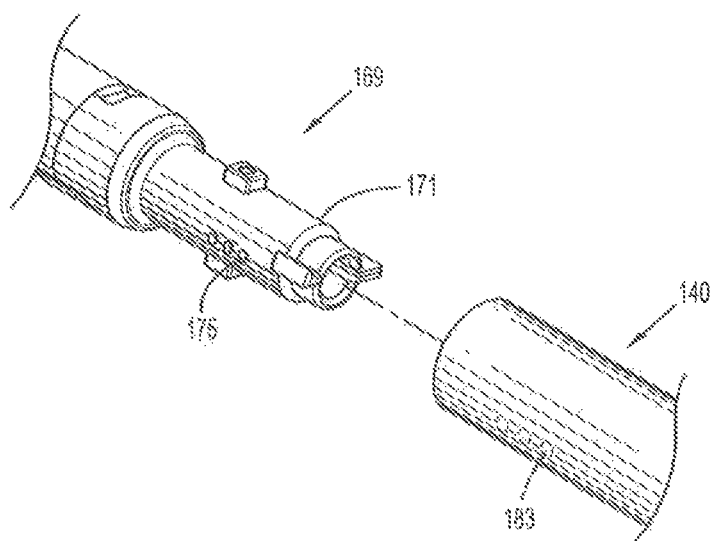

FIGS. 15A and 15B illustrate additional embodiments of the loading unit 169 having various types of identification devices. With reference to FIG. 15A, a proximal end 171 of the loading unit 169 having an electrical identifier 173 is shown. The identifier 173 may include one or more resistors, capacitors, or inductors and is coupled with a corresponding electrical contact 181 disposed on the distal end of the endoscopic portion 140. The contact may include slip rings, brushes and/or fixed contacts disposed in the endoscopic portion. The identifier 173 may be disposed on any location of the loading unit 168 and may be formed on a flexible or fixed circuit or may be traced directly on the surface of the loading unit 169.

When the loading unit 169 is coupled with the endoscopic portion 140, the contact applies a small current through the electrical identifier 173. The interrogator contact also includes a corresponding electrical sensor which measures the resistance, impedance, capacitance, and/or impedance of the identifier 173. The identifier 173 has a unique electrical property (e.g., frequency, wave patterns, etc.) which corresponds to the identifying code of the loading unit 169. Thus, when the electrical property thereof is determined, the instrument 10 determines the identity of the loading unit 169 based on the measured property.

In one embodiment, the identifier 173 may be a magnetic identifier such as gray coded magnets and/or ferrous nodes incorporating predetermined unique magnetic patterns identifying the loading unit 169 by the identifying code. The magnetic identifier is read via a magnetic sensor (e.g., ferromagnetic sensor, Hall Effect sensor, etc.) disposed at the distal end of the endoscopic portion 140. The magnetic sensor transmits the magnetic data to the instrument 10 which then determines the identity of the loading unit 169. It can also be envisioned that the contacts 181 behave as a non-contact antenna of a conductive ink or flex circuit in which the contacts 181 excite identifier 173 to emit a frequency identification signal.

FIG. 15B illustrates the proximal end 171 of the loading unit 169 having one or more protrusions 175. The protrusions 175 can be of any shape, such as divots, bumps, strips, etc., of various dimensions. The protrusions 175 interface with corresponding displacement sensors 183 disposed within the proximal segment of the endoscopic portion 140. The sensors are displaced when the protrusions 175 are inserted into the endoscopic portion. The amount of the displacement is analyzed by the sensors and converted into identification data, allowing the instrument 10 to determine staple size, cartridge length, type of the loading unit 169, proper engagement, or the like. The displacement sensors can be switches, contacts, magnetic sensors, optical sensors, variable resistors, linear and rotary variable displacement transducers which can be spring loaded. The switches are configured to transmit binary code to the instrument 10 based on their activation status. More specifically, some protrusions 175 extend a distance sufficient to selectively activate some of the switches, thereby generating a unique code based on the combination of the protrusions 175.

In another embodiment, the protrusion 175 can be color coded. The displacement sensors 183 include a color sensor configured to determine the color of the protrusion 175 to measure one or more properties of the loading unit 169 based on the color and transmits the information to the instrument 10.

Figure 16:
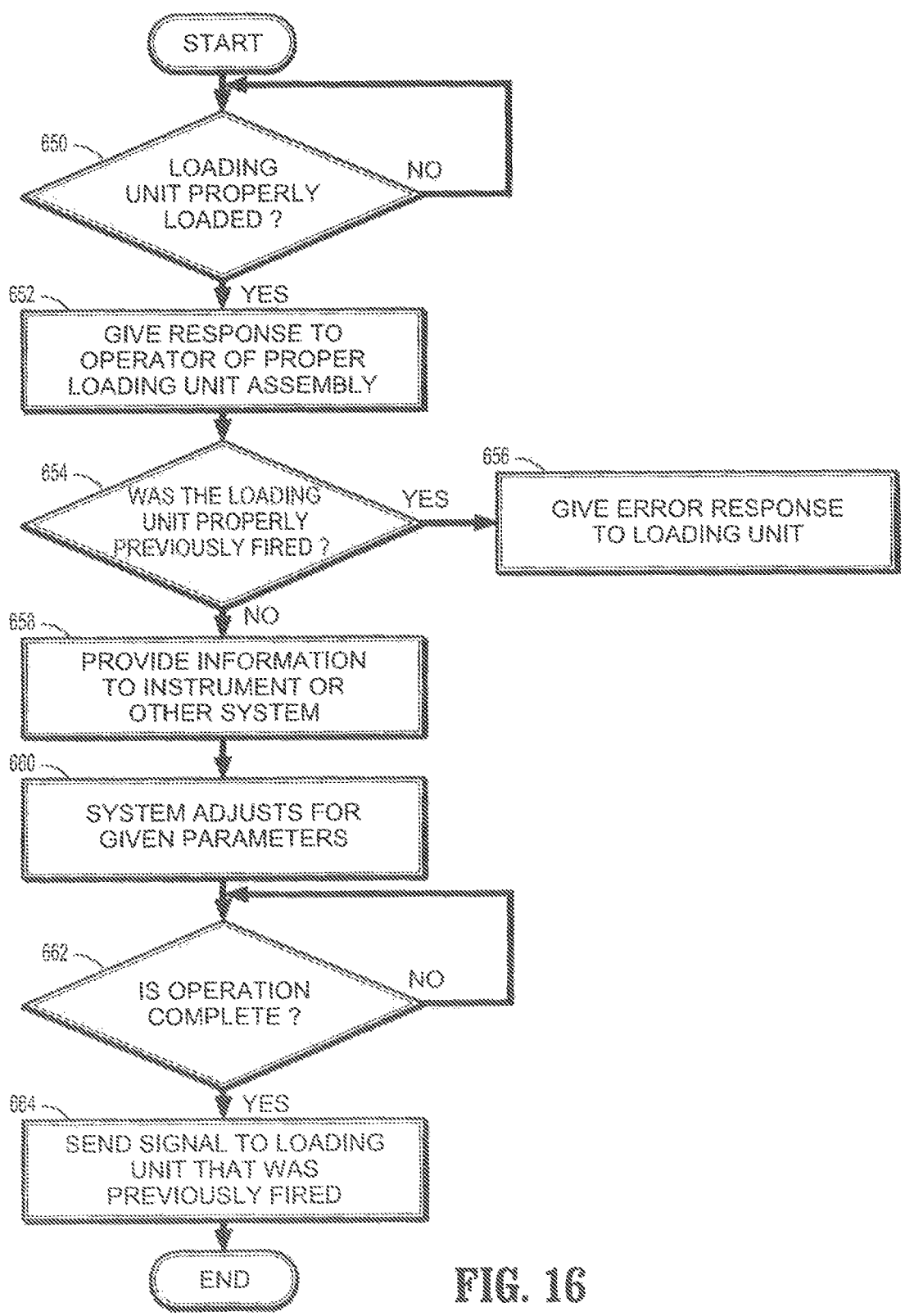
FIG. 16 is a flow chart diagram illustrating a method for authenticating the loading unit of the powered surgical instrument of FIG. 1.

FIG. 16 shows a method for identifying the loading unit 169 and providing status information concerning the loading unit 169 to the instrument 10. In step 650 it is determined whether the loading unit 169 is properly loaded into the instrument 10. This may be determined by detecting whether contact has been made with the identifier 173 and/or protrusions 175. If the loading unit 169 is properly loaded, in step 652, the loading unit 169 communicates to the instrument 10 a ready status (e.g., turning on the first light of the visual outputs 123).

In step 654, the instrument 10 verifies whether the loading unit 169 has been previously fired. This may be accomplished by providing one or more fired sensors 900 disposed in the cartridge assembly 164 (FIG. 9) which determine whether any of the staples 66 have been fired. The fired sensor 900 may be a switch or a fuse which is triggered when the sled 74 is advanced in the distal direction which is indicative of the end effector 160 being used. The fired sensor 900 may be coupled to the identifier 442 which then stores a value indicative of the previously fired status. A second fired sensor 900 may be placed distal of the last row of staples 66 such that when the sensor 900 is triggered, it is indicated that firing of the cartridge assembly 164 is complete.

If the loading unit 169 was fired, in step 656, the instrument 10 provides an error response (e.g., flashing the first light of the visual outputs 123). If the loading unit 169 has not been fired, in step 658 the loading unit 169 provides identification and status information (e.g., first light is turned on) to the instrument 10 via the identification system 440. The determination whether the loading unit 169 has been fired is made based on the saved "previously fired" signal saved in the memory of the identifier 442 as discussed in more detail below with respect to step 664. In step 660, the instrument 10 adjusts its operating parameters in response to the information received from the loading unit 169.

The user performs a surgical procedure via the instrument 10 in step 662. Once the procedure is complete and the loading unit 169 has been fired, the instrument 10 transmits a "previously fired" signal to the loading unit 169. In step 664, the loading unit 169 saves the "previously fired" signal in the memory of the identifier 442 for future interrogations by the instrument 10 as discussed with respect to step 654.

Figure 17:
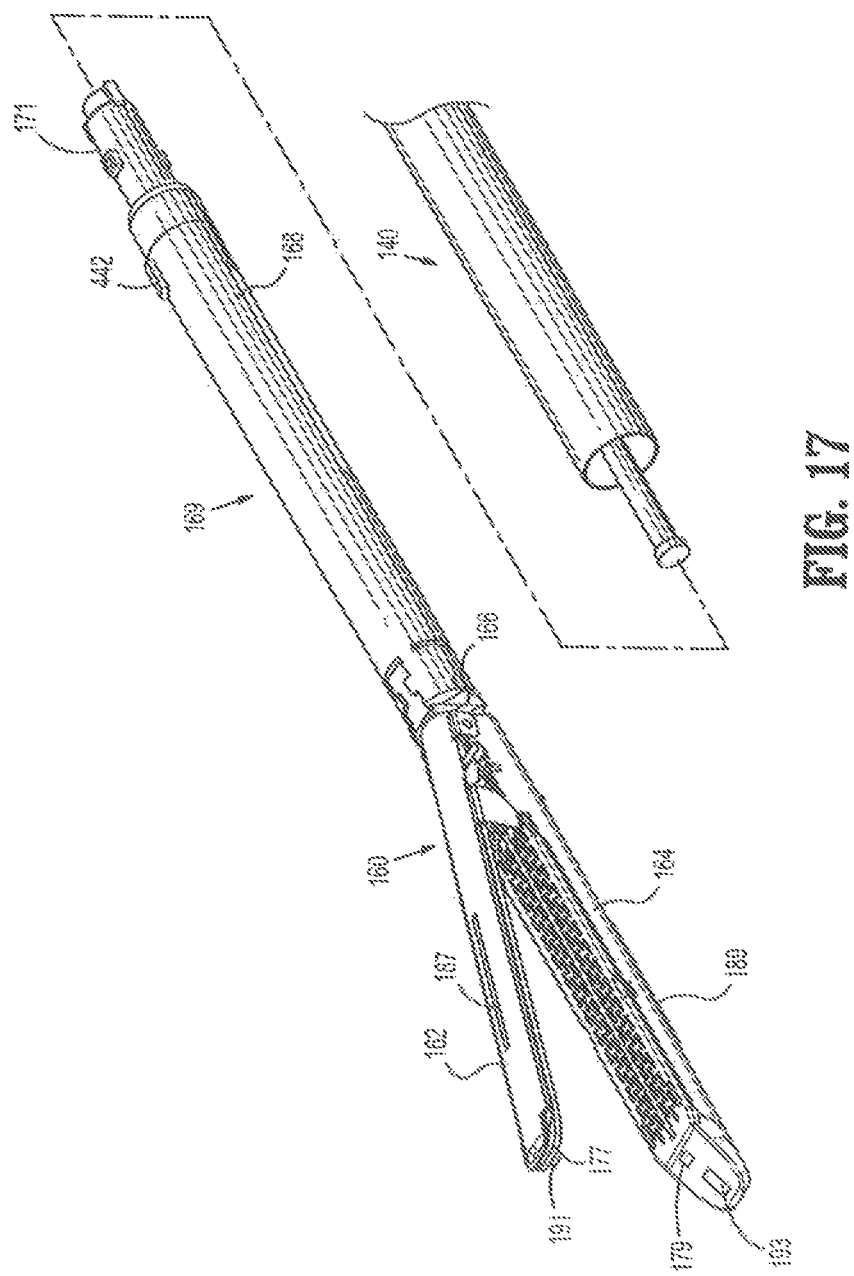
FIG. 17 is a perspective view of the loading unit of the powered surgical instrument of FIG. 1.

With reference to FIG. 17, the loading unit 169 includes one or more tissue sensors disposed within the end effector 160 for detecting the type of object being grasped, such as recognizing non-tissue objects or the tissue type of the object. The sensors can also be configured to determine amount of blood flow being passed between the jaw members of the end effector 160. More specifically, a first tissue sensor 177 is disposed at a distal portion of the anvil assembly 162 and a second tissue sensor 179 is disposed at a distal portion of the cartridge assembly 164. The sensors 177 and 179 are coupled to the identifier 442 allowing for transmission of sensor data to the microcontroller 500 of the instrument 10.

The sensors 177 and 179 are adapted to generate a field and/or waves in one or more arrays or frequencies therebetween. The sensors 177 and 179 may be acoustic, ultrasonic, ferromagnetic, Hall Effect sensors, laser, infrared, radio frequency, or piezoelectric devices. The sensors 177 and 179 are calibrated for ignoring commonly occurring material, such as air, bodily fluids and various types of human tissue and for categorizing specific tissue types (e.g., scar tissue, lung, stomach, sphincter, etc.) or detecting certain types of foreign matter. The foreign matter may be bone, tendons, cartilage, nerves, major arteries and non-tissue matter, such as ceramic, metal, plastic, etc.

The sensors 177 and 179 detect the foreign material passing between the anvil and cartridge assemblies 162 and 164 based on the absorption, reflection and/or filtering of the field signals generated by the sensors. If the material reduces or reflects a signal, such that the material is outside the calibration range and is, therefore, foreign, the sensors 177 and 179 transmit the interference information to the microcontroller 500 which then determines the type of the material being grasped by the end effector 160. The determination may be made by comparing the interference signals with a look up table listing various types of materials and their associated interference ranges. The microcontroller 500 then alerts the user of the foreign material being grasped as well as the identity thereof. This allows the user to prevent clamping, cutting, or stapling through areas containing foreign matter or the control system 501 can alter the performance of the drive motor 200 for specific tissue scenarios.

Figure 20:
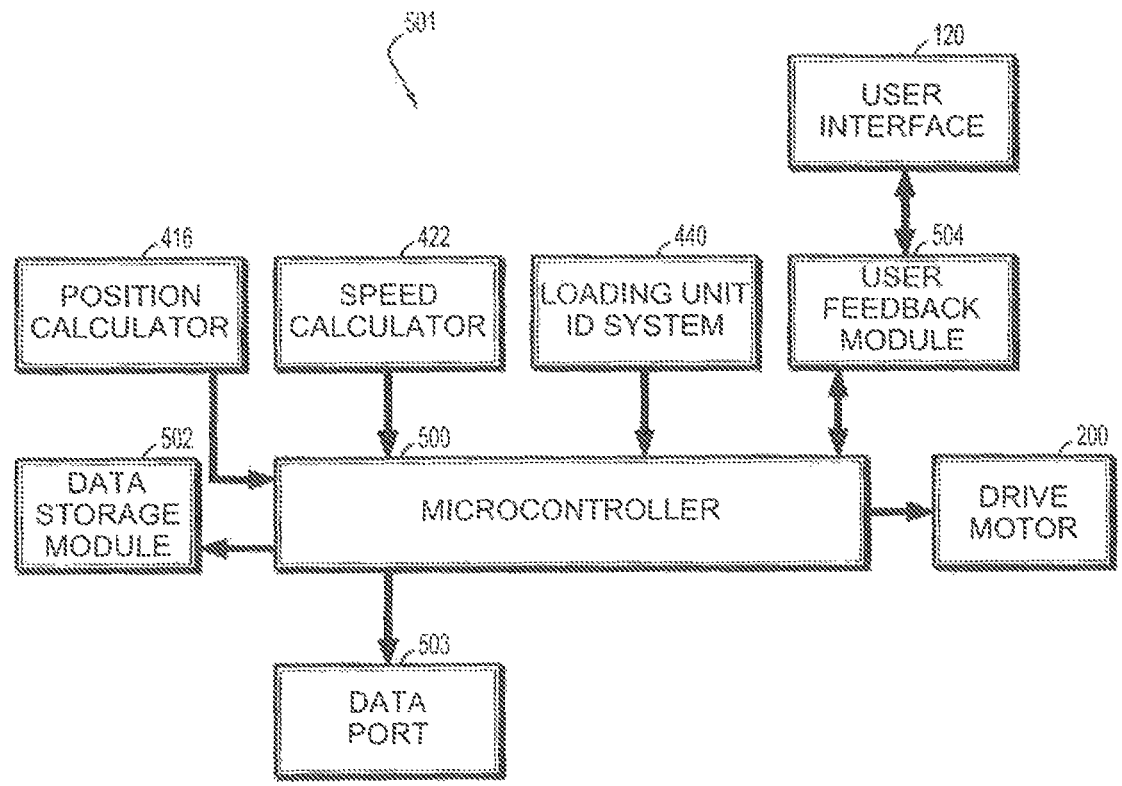
FIG. 20 is a schematic diagram of a control system of the powered surgical instrument of FIG. 1.
Figure 21:
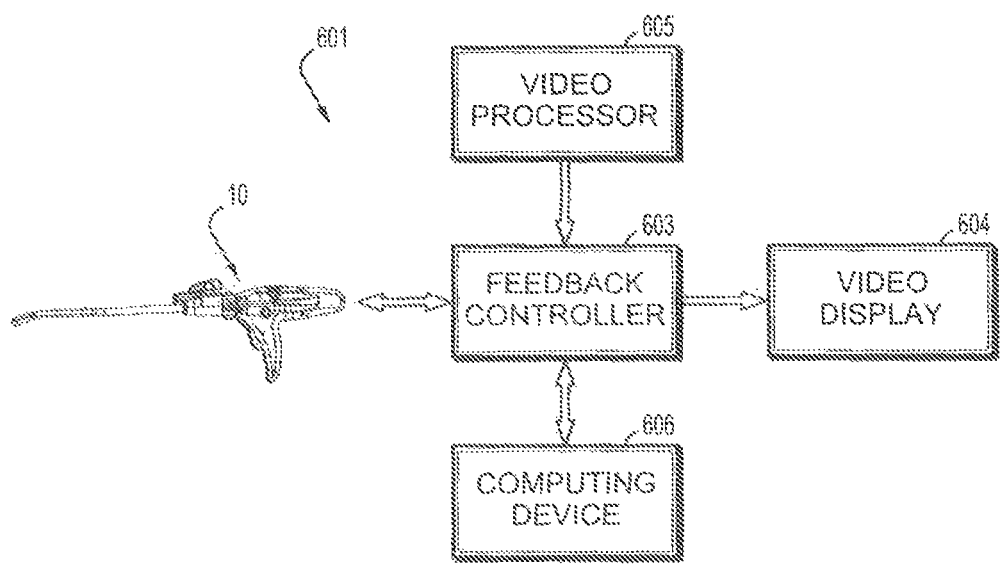
FIG. 21 is a schematic diagram of a feedback control system according to an exemplary embodiment of the present disclosure.

FIG. 20 illustrates a control system 501 including the microcontroller 500 which is coupled to the position and speed calculators 416 and 422, the loading unit identification system 440, the user interface 120, the drive motor 200, and a data storage module 502. In addition the microcontroller 500 may be directly coupled to various sensors (e.g., first and second tissue sensors 177 and 179, the load switch 230, shaft start position sensor 231, clamp position sensor 232, articulation sensor 235, linear displacement sensor 237, rotational sensor 239, firing rod rotation sensor 241, motor and battery operating module 412, rotation speed detecting apparatus 418, switches 421, voltage sensor 428, current sensor 430, the interrogator 444, etc.).

The microcontroller 500 includes internal memory which stores one or more software applications (e.g., firmware) for controlling the operation and functionality of the instrument 10. The microcontroller 500 processes input data from the user interface 120 and adjusts the operation of the instrument 10 in response to the inputs. The adjustments to the instrument 10 may include, for example, powering the instrument 10 on or off, controlling speed by means of voltage regulation or voltage pulse width modulation, limiting torque by reducing duty cycle, or pulsing the voltage on and off to limit average current delivery during a predetermined period of time.

The microcontroller 500 is coupled to the user interface 120 via a user feedback module 504 which is configured to inform the user of operational parameters of the instrument 10. The user feedback module 504 instructs the user interface 120 to output operational data on the screen 122. In particular, the outputs from the sensors are transmitted to the microcontroller 500 which then sends feedback to the user instructing the user to select a specific mode, speed or function for the instrument 10 in response thereto.

The loading unit identification system 440 instructs the microcontroller 500 which type of end effector is on the loading unit. In an embodiment, the control system 501 is capable of storing information relating to the force applied to firing rod 220 and/or end effector 160, such that when the loading unit 169 is identified, the microcontroller 500 automatically selects the operating parameters for the instrument 10. This allows for control of the force being applied to the firing rod 220 so that firing rod 220 can drive the particular end effector 160 that is on the loading unit in use at the time.

In one embodiment, the microcontroller 500 also analyzes the calculations from the position and speed calculators 416 and 422 and other sensors to determine the actual position and/or speed of the firing rod 220 and operating status of components of the instrument 10. The analysis may include interpretation of the sensed feedback signal from the calculators 416 and 422 to control the movement of the firing rod 220 and other components of the instrument 10 in response to the sensed signal. The microcontroller 500 is configured to limit the travel of the firing rod 220 once the firing rod 220 has moved beyond a predetermined point as reported by the position calculator 416. Additional parameters which may be used by the microcontroller 500 to control the instrument 10 include motor and/or battery temperature, number of cycles remaining and used, remaining battery life, tissue thickness, current status of the end effector, transmission and reception, external device connection status, etc.

In one embodiment, the instrument 10 includes various sensors configured to measure current (e.g., ammeter), voltage (e.g., voltmeter), proximity (e.g., optical sensors), temperature (e.g., thermocouples, thermistors, etc.), and force (e.g., strain gauges, load cells, etc.) to determine for loading conditions on the loading unit 169. During operation of the instrument 10 it is desirable to know the forces being exerted by the instrument 10 on the target tissue during the approximation process and during the firing process. Detection of abnormal loads (e.g., outside a predetermined load range) indicates a problem with the instrument 10 and/or clamped tissue which is communicated to the user.

Monitoring of load conditions may be performed by one or more of the following methods: monitoring speed of the drive motor 200, monitoring torque being applied by the motor, monitoring proximity of jaw members 162 and 164, monitoring temperature of components of the instrument 10, or measuring the load on the firing rod 220 via a strain sensor 185 (FIG. 4) and/or other load bearing components of the instrument 10. Speed and torque monitoring is discussed above with respect to FIG. 6 and the speed calculator 422.

Measuring the distance between the jaw members 162 and 164 can also be indicative of load conditions on the end effector 160 and/or the instrument 10. When large amounts of force are imparted on the jaw members 162 and 164, the jaw members are deflected outwards. The jaw members 162 and 164 are parallel to each other during normal operation, however, during deformation, the jaw members are at an angle relative to each other. Thus, measuring the angle between the jaw members 162 and 164 allows for a determination of the deformation of the jaw members due to the load being exerted thereon. The jaw members may include strain gauges 187 and 189 as shown in FIG. 17 to directly measure the load being exerted thereon. Alternatively, one or more proximity sensors 191 and 193 can be disposed at the distal tips of the jaw members 162 and 164 to measure the angle therebetween. These measurements are then transmitted to the microcontroller 500 which analyzes the angle and/or strain measurements and alerts the user of the stress on the end effector 160.

In another embodiment, the firing rod 220 or other load-bearing components include one or more strain gauges and/or load sensors disposed thereon. Under high strain conditions, the pressure exerted on the instrument 10 and/or the end effector 160 is translated to the firing rod 220 causing the firing rod 220 to deflect, leading to increased strain thereon. The strain gauges then report the stress measurements to the microcontroller 500. In another embodiment, a position, strain or force sensor may be disposed on the clutch plate 302.

During the approximation process, as the end effector 160 is clamped about tissue, the sensors disposed in the instrument 10 and/or the end effector 160 indicate to the microprocessor 500 that the end effector 160 is deployed about abnormal tissue (e.g., low or high load conditions). Low load conditions are indicative of a small amount of tissue being grasped by the end effector 160 and high load conditions denote that too much tissue and/or a foreign object (e.g., tube, staple line, clips, etc.) is being grasped. The microprocessor 500 thereafter indicates to the user via the user interface 120 that a more appropriate loading unit 169 and/or instrument 10 should be chosen.

During the firing process, the sensors can alert the user of a variety of errors. Sensors may communicate to the microcontroller 500 that a staple cartridge or a portion of the instrument 10 is faulty. In addition, the sensors can detect sudden spikes in the force exerted on the knife, which is indicative of encountering a foreign body. Monitoring of force spikes could also be used to detect the end of the firing stroke, such as when the firing rod 220 encounters the end of the stapling cartridge and runs into a hard stop. This hard stop creates a force spike which is relatively larger than those observed during normal operation of the instrument 10 and could be used to indicate to the microcontroller that the firing rod 220 has reached the end of loading unit 169. Measuring of the force spikes can be combined with positional feedback measurements (e.g., from an encoder, linear variable displacement transducer, linear potentiometer, etc.) as discussed with respect to position and speed calculators 416 and 422. This allows for use of various types of staple cartridges (e.g., multiple lengths) with the instrument 10 without modifying the end effector 160.

When force spikes are encountered, the instrument 10 notifies the user of the condition and takes preventative measures by entering a so-called "pulse", or pulse width modulation (PWM) or an electronic clutching mode, which is discussed in more detail below. During this mode the drive motor 200 is controlled to run only in short bursts to allow for the pressure between the grasped tissue and the end effector 160 to equalize. The electronic clutching limits the torque exerted by the drive motor 200 and prevents situations where high amounts of current are drawn from the power source 400. This, in turn, prevents damage to electronic and mechanical components due to overheating which accompanies overloading and high current draw situations.

The microcontroller 500 controls the drive motor 200 through a motor driver via a pulse width modulated control signal. The motor driver is configured to adjust the speed of the drive motor 200 either in clockwise or counter-clockwise direction. The motor driver is also configured to switch between a plurality of operational modes which include an electronic motor braking mode, a constant speed mode, an electronic clutching mode, and a controlled current activation mode. In electronic braking mode, two terminals of the drive motor 200 are shorted and the generated back EMF counteracts the rotation of the drive motor 200 allowing for faster stopping and greater positional precision in adjusting the linear position of the firing rod 220.

In the constant speed mode, the speed calculator 422 in conjunction with the microcontroller 500 and/or the motor driver adjust the rotational speed of the drive motor 200 to ensure constant linear speed of the firing rod 220. The electronic clutching mode involves repeat engagement and/or disengagement of the clutch 300 from the drive motor 200 in response to sensed feedback signals from the position and speed calculators 416 and 422. In controlled current activation mode, the current is either ramped up or down to prevent damaging current and torque spikes when transitioning between static to dynamic mode to provide for so-called "soft start" and "soft stop."

The data storage module 502 records the data from the sensors coupled to the microcontroller 500. In addition, the data storage module 502 records the identifying code of the loading unit 169, the status of the end effector 100, number of stapling cycles during the procedure, etc. The data storage module 502 is also configured to connect to an external device such as a personal computer, a PDA, a smartphone, a storage device (e.g., Secure Digital® card, Compact Flash® card, MemoryStick®, etc.) through a wireless or wired data port 503. This allows the data storage module 502 to transmit performance data to the external device for subsequent analysis and/or storage. The data port 503 also allows for so-called "in the field" upgrades of firmware of the microcontroller 500.

Figure 22A:
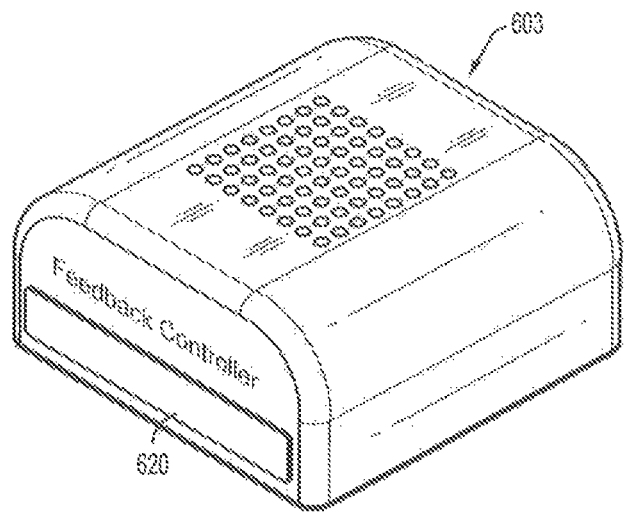
FIGS. 22A-B are perspective front and rear views of a feedback controller of the feedback control system according to an exemplary embodiment of the present disclosure.
Figure 22B:
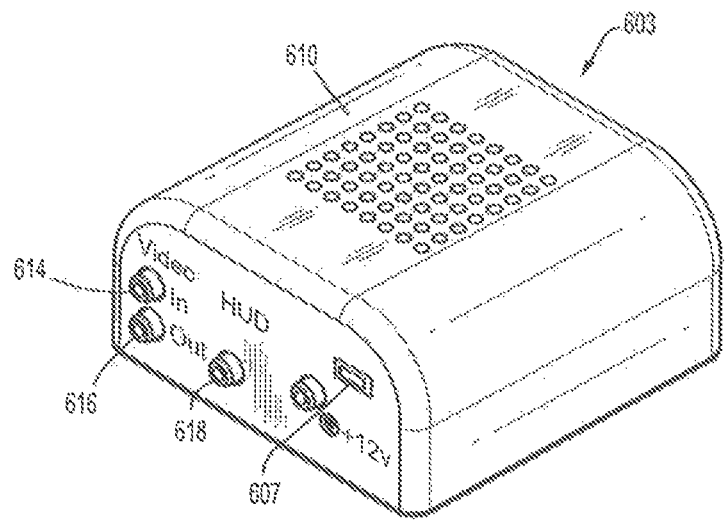
Figure 23:
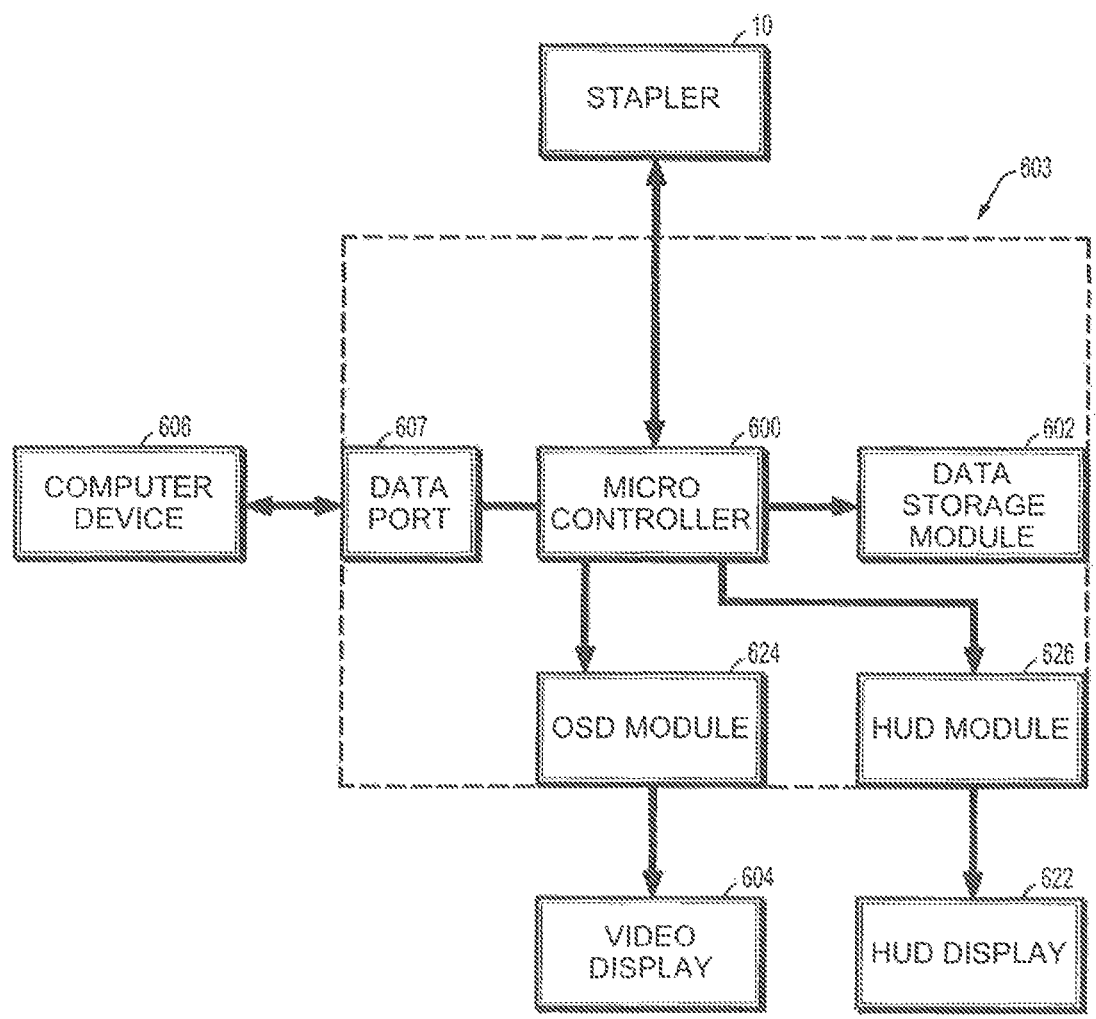
FIG. 23 is a schematic diagram of the feedback controller according to an exemplary embodiment of the present disclosure.

A feedback control system 601 is shown in FIGS. 21-23. The system includes a feedback controller 603 which is shown in FIGS. 22A-B. The instrument 10 is connected to the feedback controller 603 via the data port 502 which may be either wired (e.g., Firewire®, USB®, Serial RS232®, Serial R5485®, USART®, Ethernet®, etc.) or wireless (e.g., Bluetooth®, ANT3®, KNX®, ZWave®, X10® Wireless USB®, IrDA®, Nanonet®, Tiny OS®, ZigBee®, 802.11 IEEE, and other radio, infrared, UHF, VHF communications or the like).

With reference to FIG. 21, the feedback controller 603 is configured to store the data transmitted thereto by the instrument 10 as well as process and analyze the data. The feedback controller 603 is also connected to other devices, such as a video display 604, a video processor 605 and a computing device 606 (e.g., a personal computer, a PDA, a smartphone, a storage device, etc.). The video processor 605 is used for processing output data generated by the feedback controller 603 for output on the video display 604. The computing device 606 is used for additional processing of the feedback data. In one embodiment, the results of the sensor feedback analysis performed by the microcontroller 600 may be stored internally for later retrieval by the computing device 606.

The feedback controller 603 includes a data port 607 (FIG. 22B) coupled to the microcontroller 600 which allows the feedback controller 603 to be connected to the computing device 606. The data port 607 may provide for wired and/or wireless communication with the computing device 606 providing for an interface between the computing device 606 and the feedback controller 603 for retrieval of stored feedback data, configuration of operating parameters of the feedback controller 603 and upgrade of firmware and/or other software of the feedback controller 603.

The feedback controller 603 is further illustrated in FIGS. 22A-B. The feedback controller 603 includes a housing 610 and a plurality of input and output ports, such as a video input 614, a video output 616, a heads-up ("HUD") display output 618. The feedback controller 603 also includes a screen 620 for displaying status information concerning the feedback controller 603.

Components of the feedback controller 603 are shown in FIG. 23. The feedback controller 603 includes a microcontroller 600 and a data storage module 602. The microcontroller 600 and the data storage module 602 provide a similar functionality as the microcontroller 500 and the data storage module 502 of the instrument 10. Providing these components in a stand-alone module, in the form of the feedback controller 603, alleviates the need to have these components within the instrument 10.

The data storage module 602 may include one or more internal and/or external storage devices, such as magnetic hard drives or flash memory (e.g., Secure Digital® card, Compact Flash® card, MemoryStick®, etc.). The data storage module 602 is used by the feedback controller 603 to store feedback data from the instrument 10 for later analysis of the data by the computing device 606. The feedback data includes information supplied by the sensors disposed within the instrument 10 and the like.

The microcontroller 600 is configured to supplant and/or supplement the control circuitry, if present, of the instrument 10. The microcontroller 600 includes internal memory which stores one or more software application (e.g., firmware) for controlling the operation and functionality of the instrument 10. The microcontroller 600 processes input data from the user interface 120 and adjusts the operation of the instrument 10 in response to the inputs. The microcontroller 600 is coupled to the user interface 120 via a user feedback module 504 which is configured to inform the user of operational parameters of the instrument 10. More specifically, the instrument 10 is configured to connect to the feedback controller 603 wirelessly or through a wired connection via a data port 407 (FIG. 6).

In a disclosed embodiment, the microcontroller 600 is connected to the drive motor 200 and is configured and arranged to monitor the battery impedance, voltage, temperature and/or current draw and to control the operation of the instrument 10. The load or loads on battery 400, transmission, drive motor 200 and drive components of the instrument 10 are determined to control a motor speed if the load or loads indicate a damaging limitation is reached or approached. For example, the energy remaining in battery 400, the number of firings remaining, whether battery 400 must be replaced or charged, and/or approaching the potential loading limits of the instrument 10 may be determined. The microcontroller 600 may also be connected to one or more of the sensors of the instrument 10 discussed above.

The microcontroller 600 is also configured to control the operation of drive motor 200 in response to the monitored information. Pulse modulation control schemes, which may include an electronic clutch, may be used in controlling the instrument 10. For example, the microcontroller 600 can regulate the voltage supply of the drive motor 200 or supply a pulse modulated signal thereto to adjust the power and/or torque output to prevent system damage or optimize energy usage.

In one embodiment, an electric braking circuit may be used for controlling drive motor 200, which uses the existing back electromotive force of rotating drive motor 200 to counteract and substantially reduce the momentum of drive tube 210. The electric braking circuit improves the control of drive motor 200 and/or drive tube 210 for stopping accuracy and/or shift location of powered surgical instrument 10. Sensors for monitoring components of powered surgical instrument 10 and to help prevent overloading of powered surgical instrument 10 may include thermal-type sensors, such as thermal sensors, thermistors, thermopiles, thermocouples and/or thermal infrared imaging and provide feedback to the microcontroller 600. The microcontroller 600 may control the components of powered surgical instrument 10 in the event that limits are reached or approached and such control can include cutting off the power from the power source 400, temporarily interrupting the power or going into a pause mode and/or pulse modulation to limit the energy used. The microcontroller 600 can also monitor the temperature of components to determine when operation can be resumed. The above functions of the microcontroller 600 may be used independently of, or factored with current, voltage, temperature and/or impedance measurements.

The result of the analysis and processing of the data by the microcontroller 600 is output on video display 604 and/or the HUD display 622. The video display 604 may be any type of display such as an LCD screen, a plasma screen, electroluminescent screen and the like. In one embodiment, the video display 604 may include a touch screen and may incorporate resistive, surface wave, capacitive, infrared, strain gauge, optical, dispersive signal or acoustic pulse recognition touch screen technologies. The touch screen may be used to allow the user to provide input while viewing operational feedback. The HUD display 622 may be projected onto any surface visible to the user during surgical procedures, such as lenses of a pair of glasses and/or goggles, a face shield, and the like. This allows the user to visualize vital feedback information from the feedback controller 603 without losing focus on the procedure.

The feedback controller 603 includes an on-screen display module 624 and a HUD module 626. The modules 626 process the output of the microcontroller 600 for display on the respective displays 604 and 622. More specifically, the OSD module 624 overlays text and/or graphical information from the feedback controller 603 over other video images received from the surgical site via cameras disposed therein. The modified video signal having overlaid text is transmitted to the video display 604 allowing the user to visualize useful feedback information from the instrument 10 and/or feedback controller 603 while still observing the surgical site.

Figure 24:
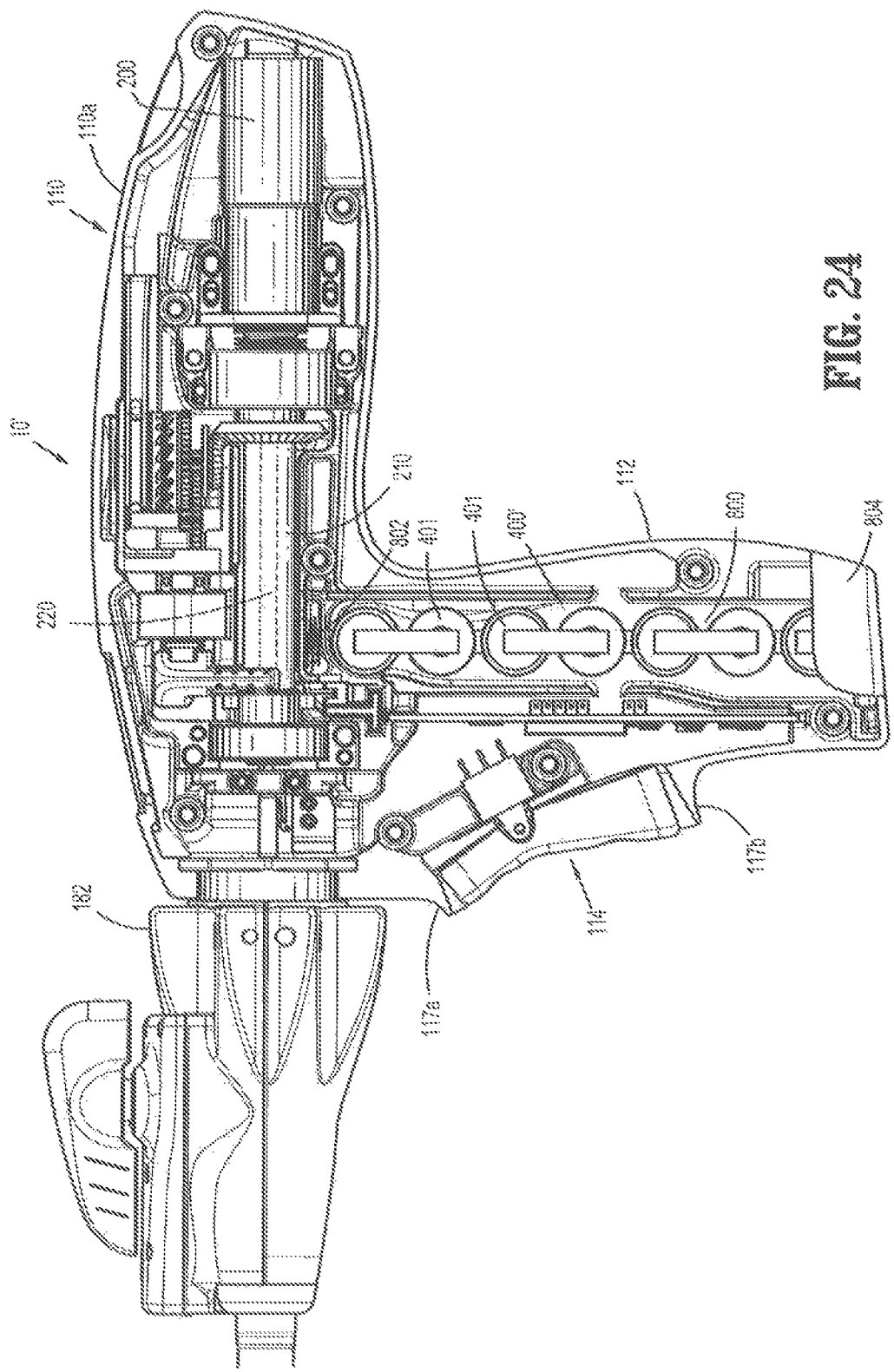
FIG. 24 is a partial sectional view of internal components of a powered surgical instrument in accordance with an embodiment of the present disclosure.
Figure 25:
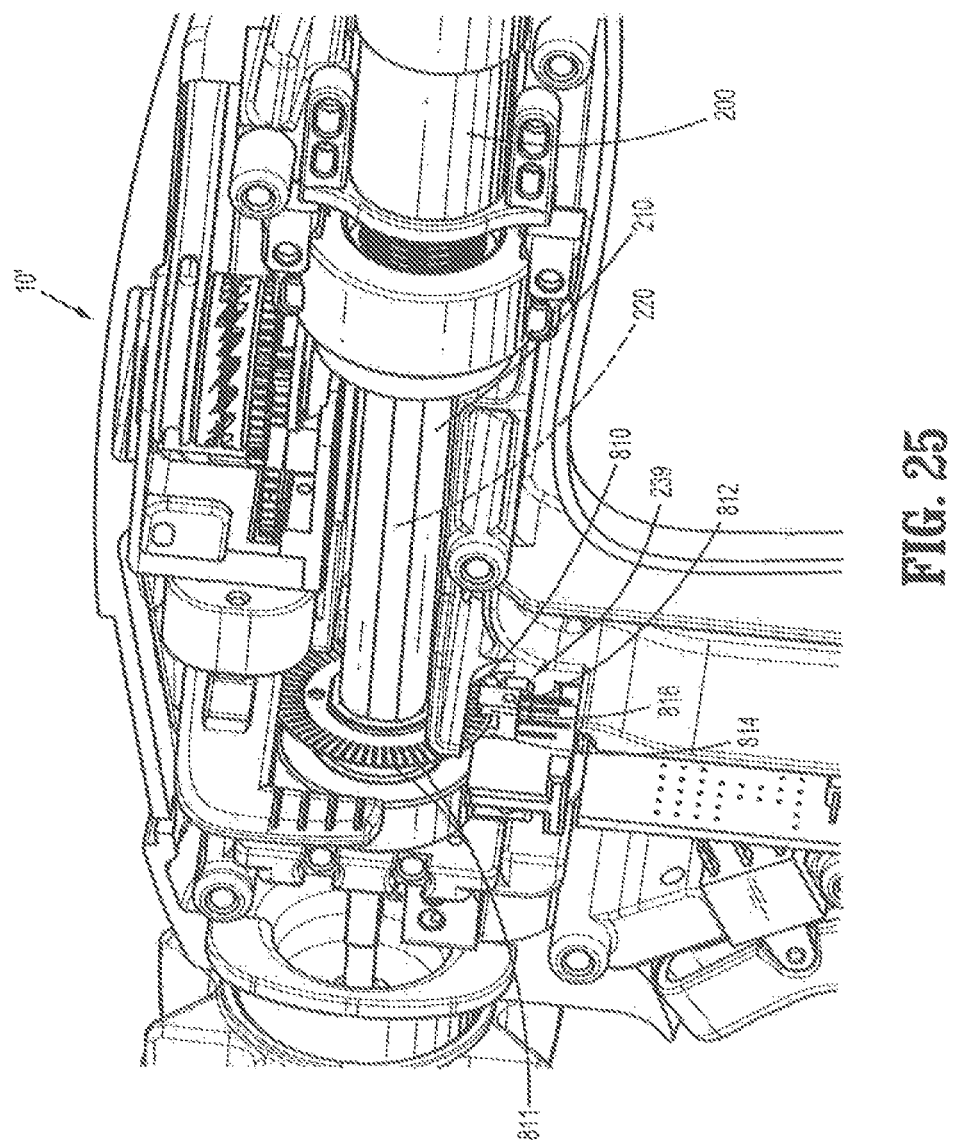
FIG. 25 is a partial perspective sectional view of internal components of the powered surgical instrument in accordance with an embodiment of the present disclosure.

FIGS. 24-25 illustrate another embodiment of the instrument 10'. The instrument 10' includes a power source 400' having a plurality of cells 401 arranged in a straight series configuration. The power source 400' is inserted vertically into a vertical battery chamber 800 within the handle portion 112. The battery chamber 800 includes spring contacts 802 within the top portion thereof to push downward the power source 400'. In one embodiment, the spring contacts 802 may include contacts to electrically couple with the power source 400'. The power source 400' is held within the battery chamber 800 via a battery cap 804 which is configured to slide in a distal direction to lock in place. The cap 804 and the handle 112 may include tongue and groove couplings to keep the cap 804 from sliding out. The power source 400' is biased against the cap 804 due to the downward force of the spring contacts 802. As the cap 804 is slid in a proximal direction, the power source 400' is ejected from the battery chamber 800 by the spring contacts 802.

FIG. 25 shows another embodiment of the rotational sensor 239 which detects the rotation of the drive tube 210, thus, measuring the rate of rotation of the drive tube 210 which allows for determination of the linear velocity of the firing rod 220. The rotational sensor 239 includes an encoder wheel 810 mounted to drive tube 210 and an optical reader 812 (e.g., photo interrupter). The optical reader 812 is configured to determine the number of interruptions in a light beam which is continuously provided between two opposing edges 814 and 816 thereof. The wheel 810 rotates with the drive tube 210 and includes a plurality of slits 811 therethrough.

The outer edge of the wheel 810 is disposed between the opposing edges of the optical reader 812 such that the light being transmitted between the edges 814 and 816 shines through the slits 811. The light beam between the edges 814 and 816 is interrupted by the wheel 810 as the drive tube 210 is rotated. The optical reader 812 measures the number of interruptions in the light beam and rate of occurrences thereof and transmits these measurements to the speed calculator 422 which then determines the speed of the drive rod 220 as discussed above.

FIGS. 27-32 show the instrument 10' having a retraction assembly 820 for retracting the firing rod 220 from a fired position. The retraction assembly 820 provides for a manually driven mechanical interface with the drive tube 210 allowing for manual retraction of the firing rod 220 via ratcheting action of the retraction assembly 820. This may be useful in certain situations to give the user of the instrument manual control over the position of the firing rod 220 (e.g., electrical malfunction, stuck end effector 160, etc.). The retraction assembly 820 may be configured as a modular assembly which can be inserted into the instrument 10'.

Figure 30:
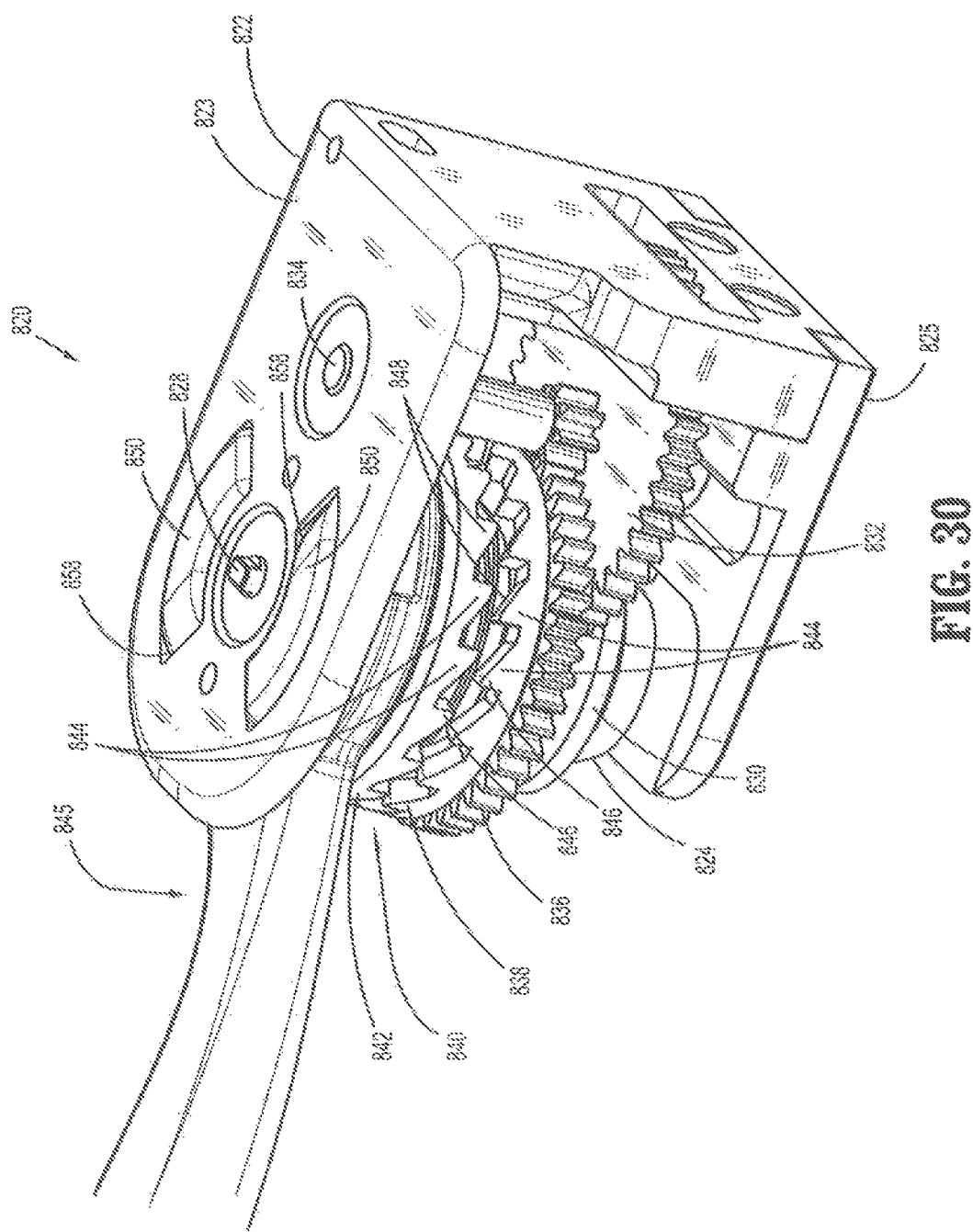
FIG. 30 is a perspective view of a modular retraction assembly of the powered surgical instrument in accordance with an embodiment of the present disclosure.

With reference to FIG. 30, the retraction assembly 820 includes a retraction chassis 822 having a top portion 823 and a bottom portion 825. The retraction assembly 820 interfaces mechanically with the drive tube 210 via a drive gear 826 and a retraction gear 824. First spur gear 830 is rigidly attached to the retraction gear 824. The drive gear 826 is attached to the drive tube 210 and is translated in response to the rotation of the drive tube 210. Conversely, rotation of the drive gear 826 imparts rotation on the drive tube 210. The drive gear 826 and the retraction gear 824 may be bevel gears allowing the gears 824 and 826 to interface in an orthogonal manner.

The retraction gear 824 is coupled to a first spindle 828 which is disposed in a substantially orthogonal manner between the top and bottom portions 823 and 825 of the retraction chassis 822. The first spindle 828 is rotatable around a longitudinal axis defined thereby. The first spindle 828 further includes first spur gear 830 attached thereto and to the retraction gear 824. The first spur gear 830 interfaces with a second spur gear 832 disposed on a second spindle 834 which is also is disposed in a substantially perpendicular manner between the top and bottom portions 823 and 825 of the retraction chassis 822 and is rotatable around a longitudinal axis defined thereby.

Figure 31:
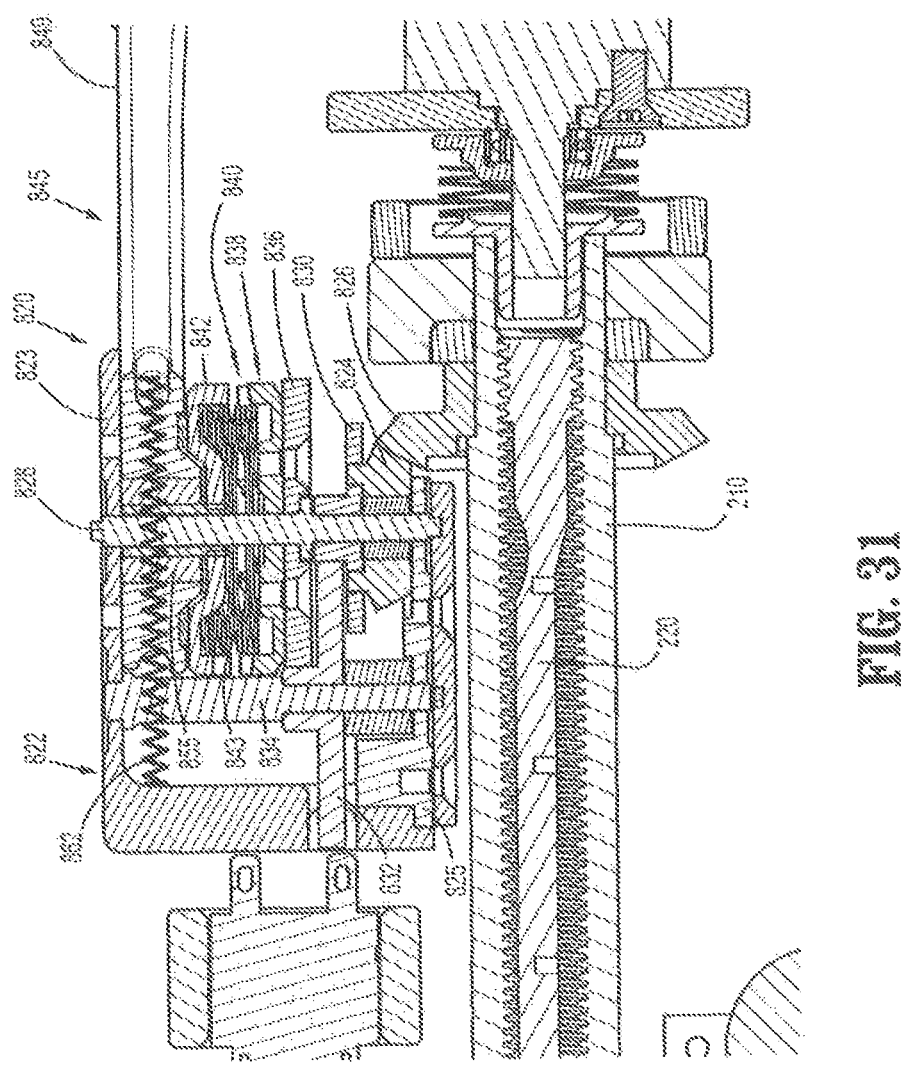
FIG. 31 is an enlarged partial sectional view of internal components of a powered surgical instrument in accordance with an embodiment of the present disclosure.

The second spur gear 832 interfaces mechanically with a third spur gear 836 which is disposed on the first spindle 828. The third spur gear 836 is attached to a first clutch portion 838 of a unidirectional clutch assembly 840. The clutch assembly 840 further includes a second clutch portion 840 rotatably disposed on the first spindle 828 above the first clutch portion 838 with a spring 843 disposed between the first and second clutch portions 838 and 842 thereby biasing the first and second clutch portions 838 and 842 toward a raised non-interlocking configuration (e.g., first configuration) as shown in FIG. 31.

Rotation of the drive tube 210 and/or the drive gear 826 imparts rotation on the retraction gear 824 and the first, second and third spur gears 830, 832 and 836 along with the first portion 838 and the respective spindles 828 and 834. Since, the second clutch portion 842 can rotate about the spindle 828 and is separated from the first clutch portion 838 by the spring 843, the rotation of the first portion 838 is not translated thereto.

Figure 32:
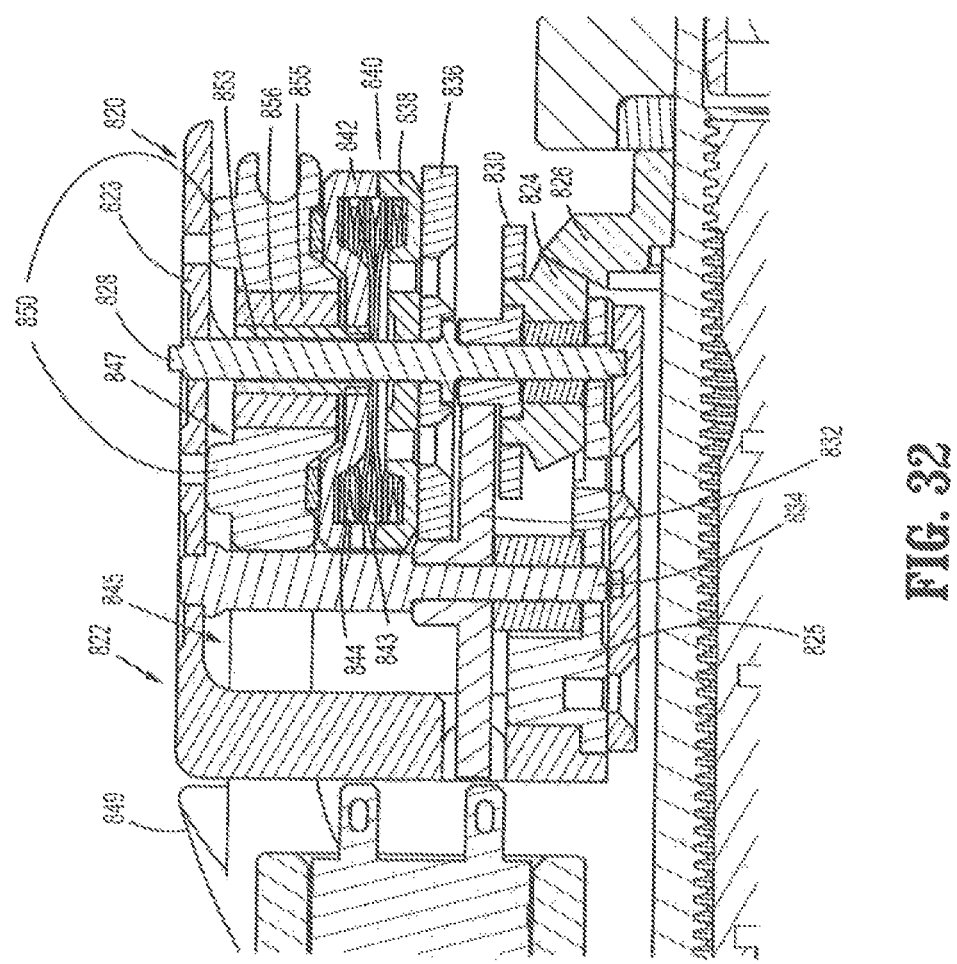
FIG. 32 is an enlarged partial sectional view of internal components of a powered surgical instrument in accordance with an embodiment of the present disclosure.

The first and second clutch portions 838 and 842 include a plurality of interlocking teeth 844 having a flat interlocking surface 846 and a sloping slip surface 848. (See FIG. 30.) The retraction assembly 820 is actuated by a retraction lever 845. As shown in FIG. 32, the second clutch portion 842 is pushed downwards by the retraction lever 845 thereby interfacing the teeth 844. The slip surfaces 848 allow for the interlocking surfaces 846 to come in contact with each other thereby allowing rotation of the second clutch portion 842 to rotate the first clutch portion 838 and all of the interfacing gears.

The retraction lever 845 includes a camming portion 847 and a handle 849 attached thereto. The camming portion 847 includes an opening 853 which houses a unidirectional needle clutch 855 which is in mechanical cooperation with a fitting 856 which is operatively coupled to the first spindle 828 thereby allowing the retraction lever 845 to rotate about the first spindle 828.

Figure 27:
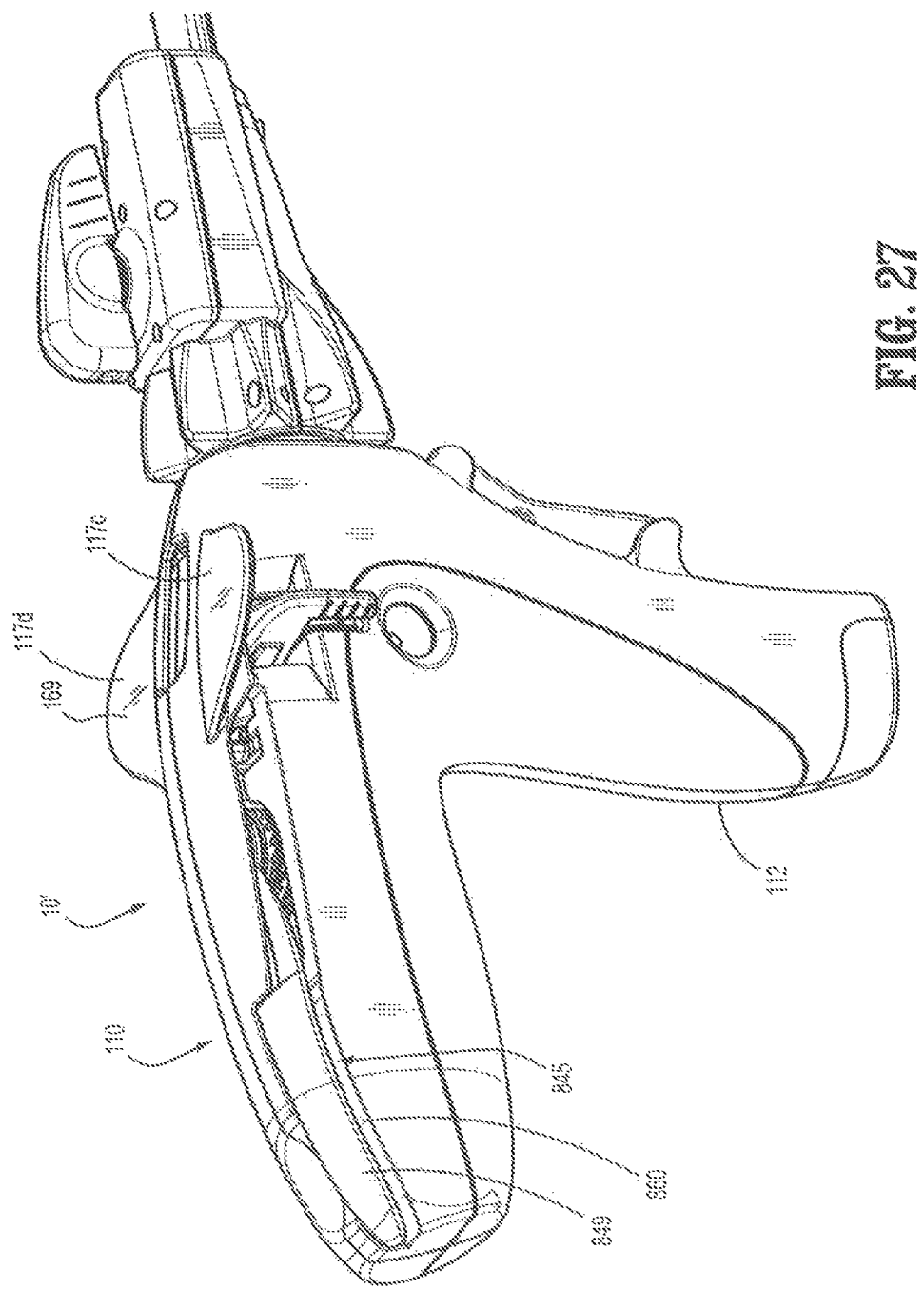
FIG. 27 is a partial perspective view of a retraction lever of the powered surgical instrument in accordance with an embodiment of the present disclosure.
Figure 29:
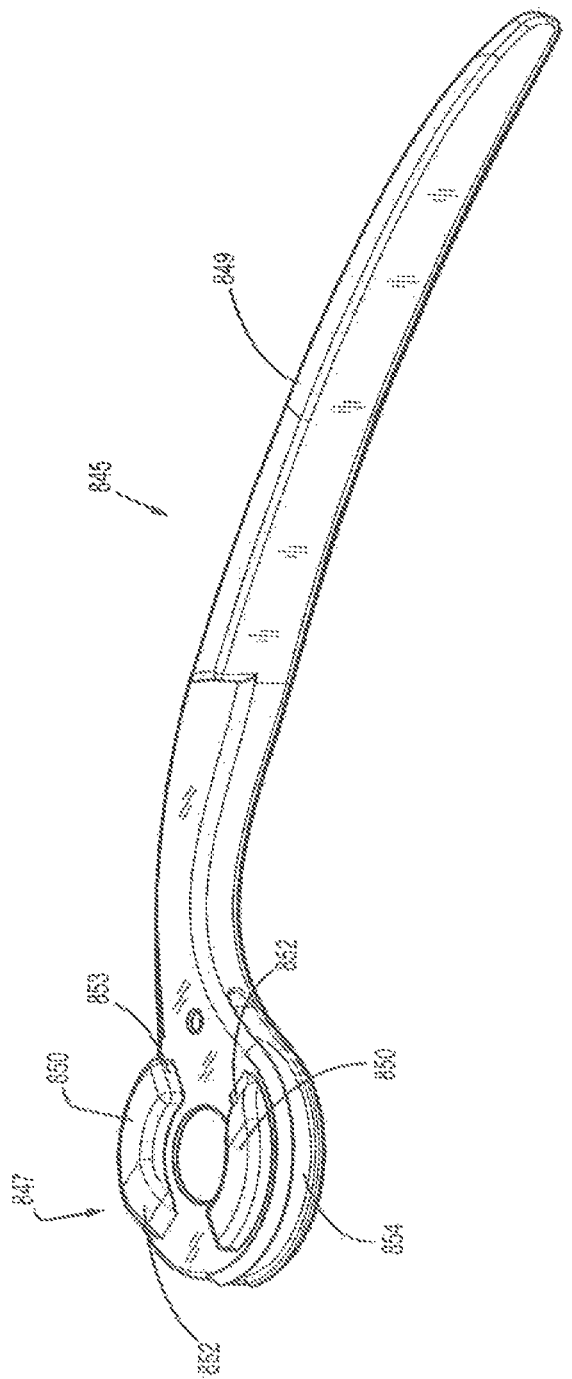
FIG. 29 is a perspective view of a lever in accordance with an embodiment of the present disclosure.

With reference to FIG. 29, the lever 845 includes a one or more camming members 850 each having a camming surface 852. In the first configuration, the lever 845 is disposed along a lever pocket 860 of the housing 110 as shown in FIG. 27. By nesting the lever 845 into the housing 110, a longer lever can be utilized which gives the user a much greater mechanical advantage over other manual retraction systems. The lever 845 is pushed up by the spring 843 against the top portion 823 and the camming members 850 are disposed within corresponding cam pockets 858. The lever 845 is also maintained in the first configuration by a return extension spring 862 mounted between the top portion 823 and the camming portion 847. The camming members 850 and the lever pocket 860 limit the rotational range of the lever 845.

As the lever 845 is pulled out of the lever pocket 860, the camming members 850 interface with the corresponding cam pockets 823 and push the camming portion 847 of the lever 845 in a downward direction. The downward movement compresses the spring 843 and pushes the first and second clutch portions 838 and 842 together interlocking the teeth 844 thereby engaging the portions 838 and 842 in a second configuration. Rotation of the camming portion 847 in a counterclockwise direction actuates the needle clutch 855 which interfaces with the fitting 856 and is axially coupled to the first spindle 828. Continual rotation of the lever 845 rotates the clutch assembly 840 which in turn rotates the fitting 856 which is keyed to the upper clutch 842, which is now mated to the lower clutch 838. This lower clutch 838 is fastened to the third spur gear 836 which then drives the spur gears 836, 832 and 830 and the retraction and drive gears 824 and 826. This in turn rotates drive tube 210 and retracts the drive rod 220.

Figure 28:
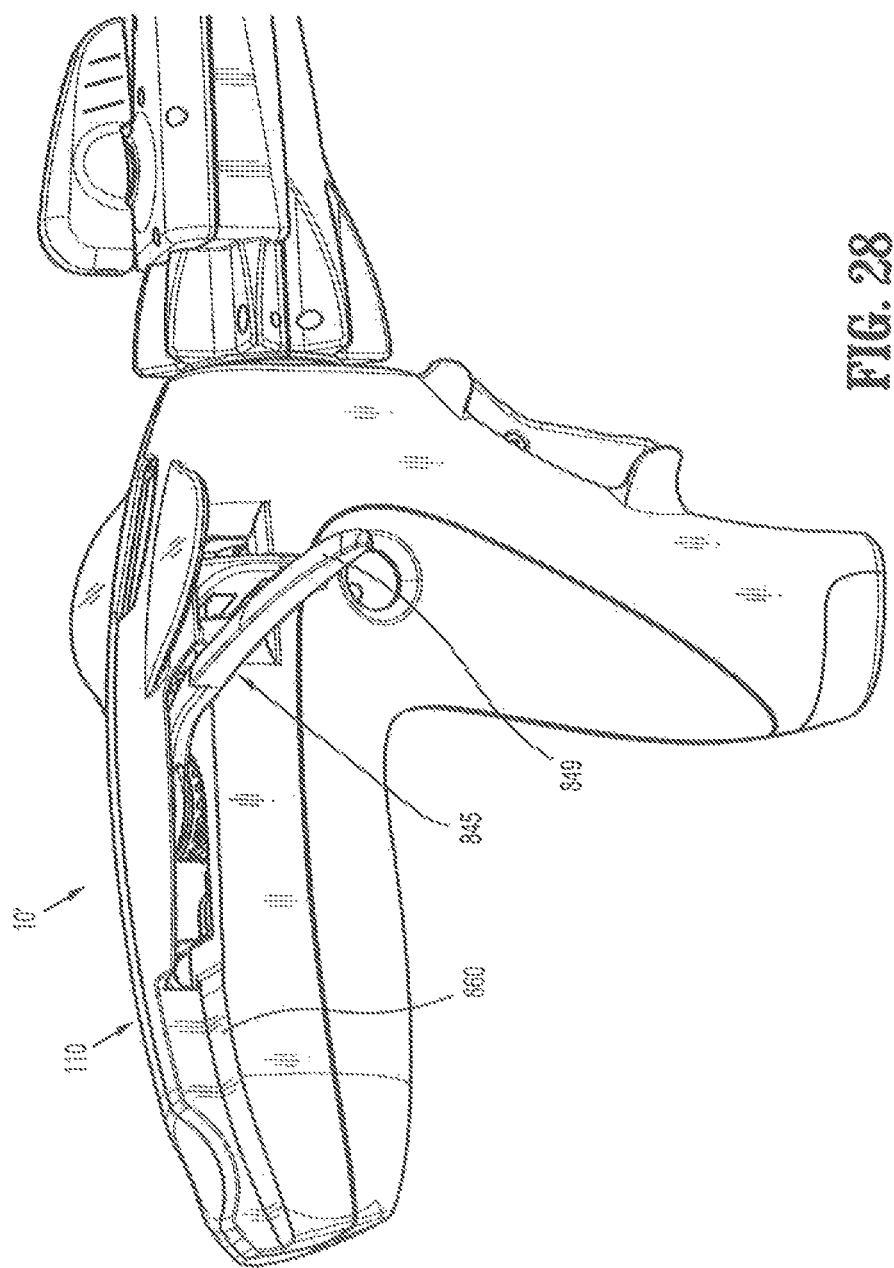
FIG. 28 is a partial perspective view of the powered surgical instrument in accordance with an embodiment of the present disclosure.

The lever 845 can be rotated until the handle 849 abuts the housing 110 as shown in FIG. 28. Thereafter, the lever 845 is brought back to its first configuration by the return extension spring 862 which rides in the radial groove 854. This raises the camming portion 847 allowing the second clutch portion 842 to also move upward and disengage the first clutch portion 838. The needle clutch 855 releases the fitting 856 allowing the lever 845 to return to the first configuration without affecting the movement of the drive tube 210. Once the lever 845 is returned to the first configuration, the lever 845 may be retracted once again to continue to ratchet the driving rod 220. Thus, the assembly can be configured for one or more movements of the lever 845 to partially or fully retract the firing rod 220.

With respect to other aspects of the present disclosure, to advance the state of the art of minimizing medical waste, it is contemplated that a sealed battery pack compartment, and/or a sealed instrument housing and/or a sealed handle assembly can be configured as part of a surgical apparatus according to the present disclosure to prevent contamination of batteries of battery-powered surgical apparatuses. Thus, the perimeter at which sealing of the battery pack occurs can be extended, in one embodiment, from the battery pack to the handle assembly and in yet another embodiment to the instrument housing.

Figure 33:
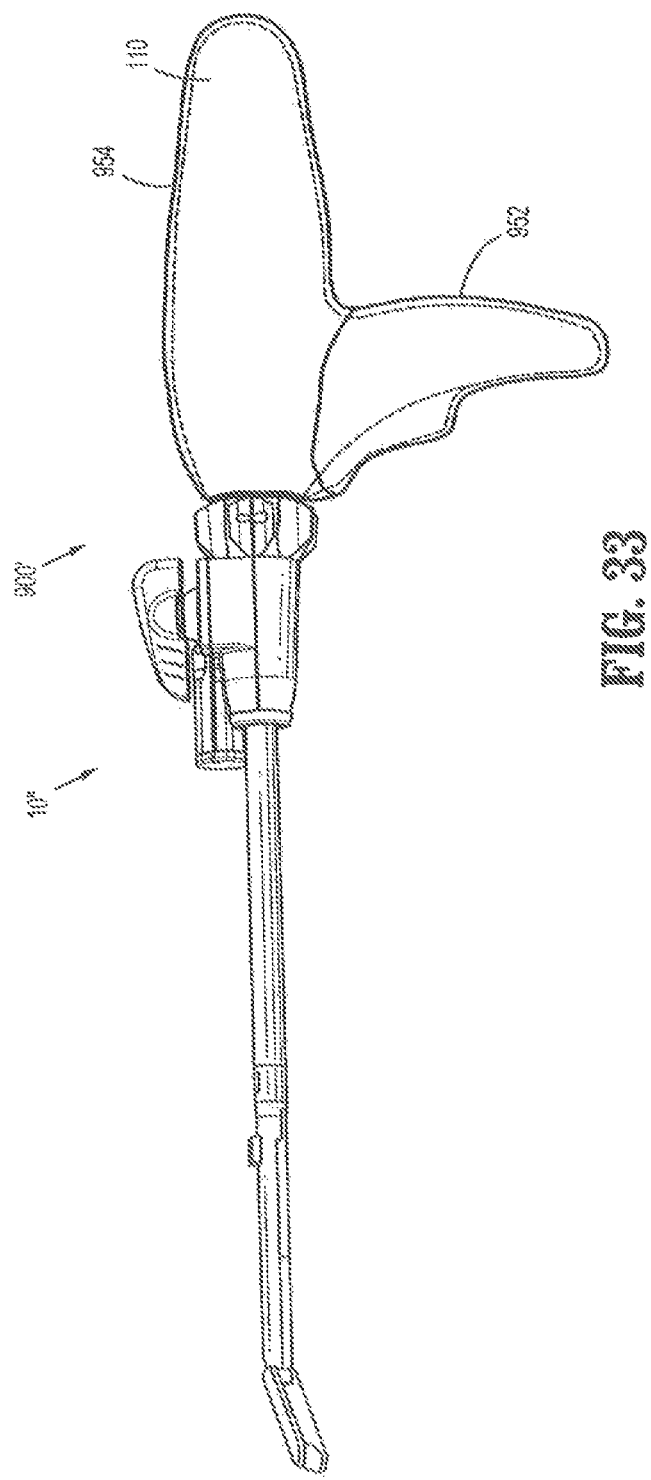
FIG. 33 is a perspective view of a powered surgical instrument having one or more sealing members around a power head of the instrument according to an embodiment of the present disclosure.
Figure 34:
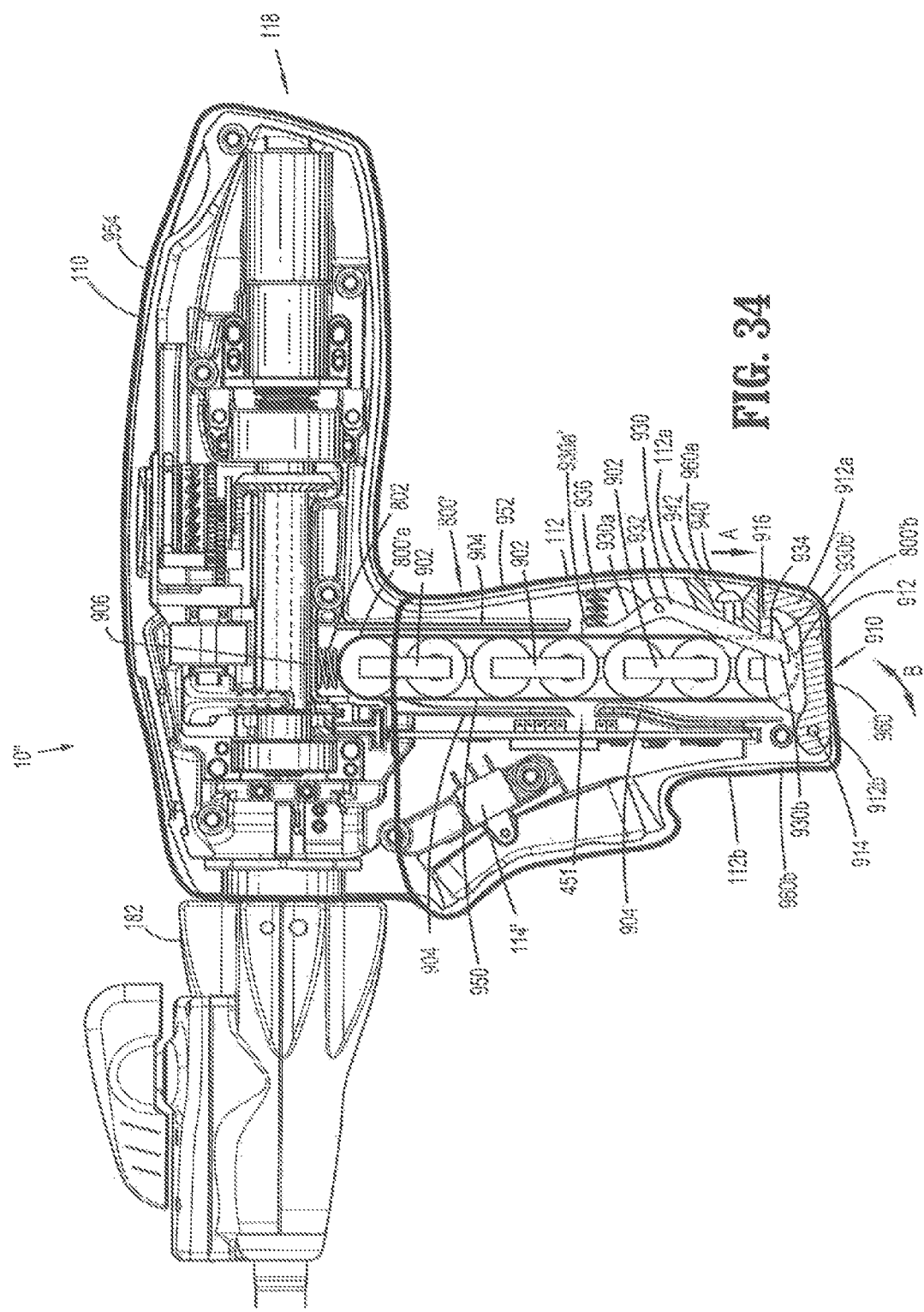
FIG. 34 is a partial cross-sectional view of the power head of FIG. 33 illustrating the internal components of the power head and the one or more sealing members.
Figure 35:
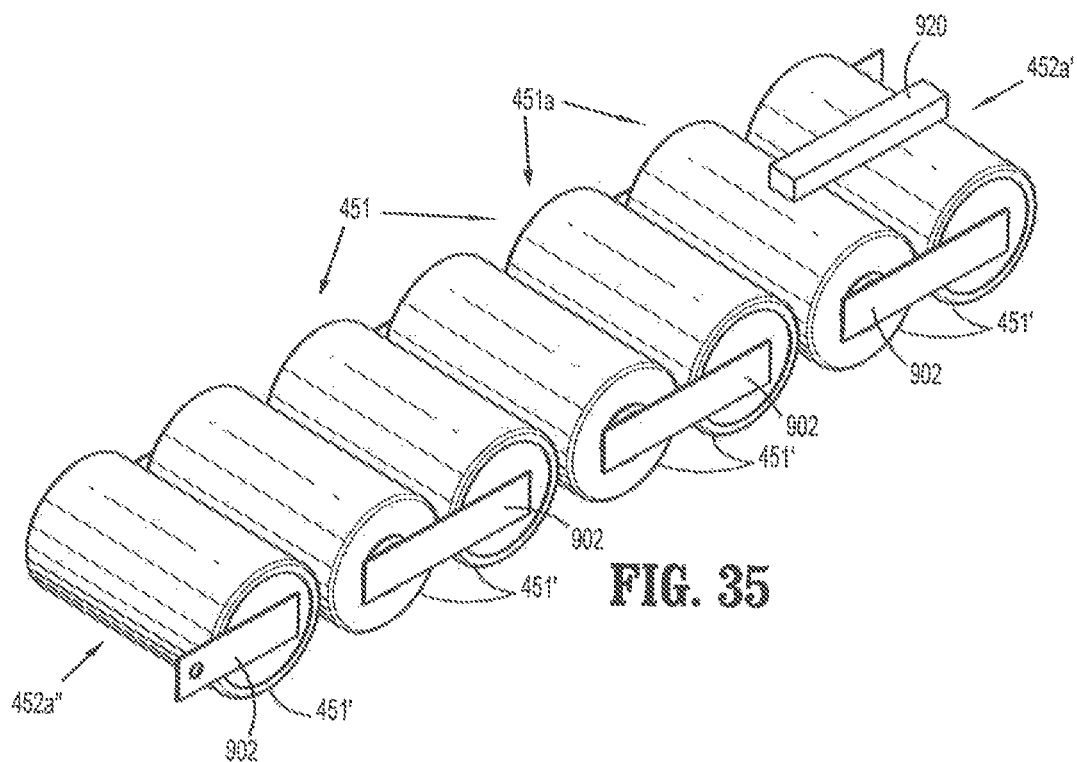
FIG. 35 is a perspective view illustrating a battery pack or power supply pack for the power head of FIGS. 33 and 34 according to one embodiment of the present disclosure.
Figure 36:
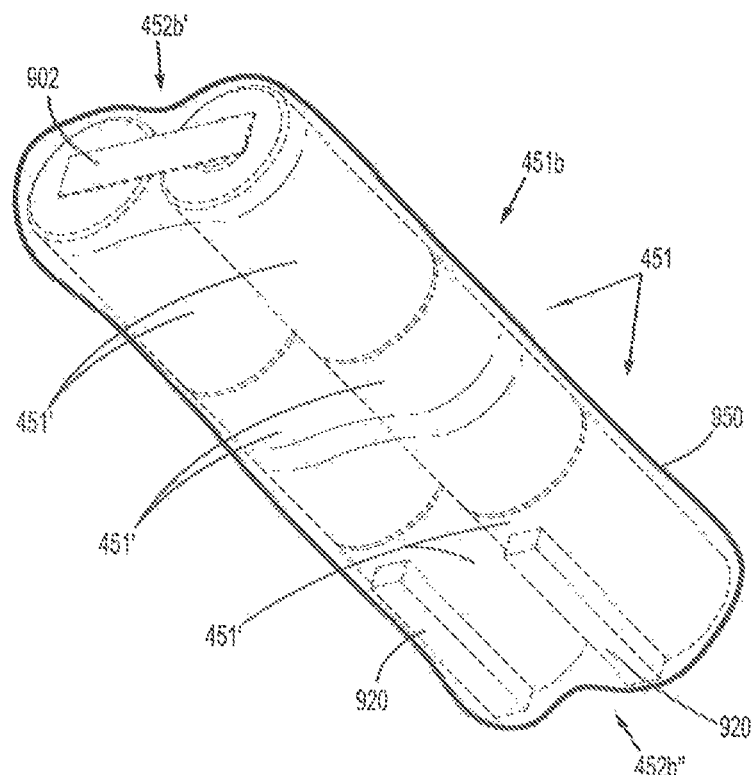
FIG. 36 is a perspective view of a battery pack or power supply pack having a sealing member according to one embodiment of the present disclosure.

More particularly, referring to FIGS. 33-36, surgical instrument 10" is illustrated. Surgical instrument 10" is substantially identical to surgical instrument 10' except that surgical instrument 10" includes at least one battery-retaining structure such as battery chamber or compartment 800' that differs from battery chamber or compartment 800. In addition, although surgical instrument 10' also includes a power head, surgical instrument 10" includes a power head 900' that is configured to include the battery chamber or compartment 800'. As defined herein, the power head 900' is the portion of the surgical instrument 10" extending from proximal portion 118 of the housing 110 to a distal portion 118' of the housing portion 110. Power head 900' includes, as defined below with respect to FIG. 38 and FIGS. 4-12, a set of operating components that provide power and operate the surgical instrument 10" and that are mounted within or adjacent the housing 110. For reference purposes, the battery chamber 800' includes an upper end 800'a and a lower end 800'b. As illustrated in FIGS. 35 and 36, at least one battery 451' or a plurality of the cells or batteries 451' forming a battery pack 451 may be oriented either in a side-by-side configuration 451a as illustrated in FIG. 35 or in an end-to-end configuration 451b as illustrated in FIG. 36. As defined herein, a battery may include, in addition to battery cells 451', a capacitor or an induction coil each storing electrical charge or a fuel cell or other suitable power supply mechanism. The battery cells 451' in configurations 451a and 451b provide a cell alignment/shape/configuration that facilitates ejection of the cell or battery pack 451' from the battery chamber 800' so as to avoid medical contamination of the individual battery cells 451' or of the battery pack 451 either during or after the ejection process. The battery packs in the side-by-side configuration 451a include terminal connector strips 902 that alternately extend between and connect positive and negative polarized terminals of the battery cells 451'. In configuration 451a, the battery pack 451 includes an upper end 452a' and a lower end 452a".

The battery packs in the end-to-end configuration 451b include terminal connector strips 902 that are disposed only at the longitudinal ends of the battery cells 451'. In configuration 451b, the battery pack 451 includes an upper end 452b' and a lower end 452b". Alignment posts and/or keys 920 may be disposed on the perimeter or exterior of the battery pack 451 to ensure correct orientation during mating/loading into the battery chamber 800'. Correct orientation also ensures proper battery terminal polarity within the battery chamber 800' or housing of the device.

Electrical contacts 906 may be disposed at the upper end 800'a of the battery chamber 800' to mate with the corresponding polarized terminals on the particular battery pack 451 and are in electrical communication with power circuitry (not shown). The contacts 906 may serve at least two functions.

In one embodiment, referring to FIG. 34, the contacts 906 may be spring loaded positive and negative electrical connections 802. During loading of the battery pack 451 into the battery chamber 800' through battery chamber port 910, the upper ends 452a', 452b' of either battery pack configuration 451a or 451b, respectively, are inserted through the chamber port 910 so that the alignment keys 920 can align properly within the chamber 800' via receptacles (not shown) until contact is made with the contacts 906 that are spring loaded and that are located at the upper end 800'a of the chamber 800'. The battery chamber 800' includes ribbing 904 in the instrument housing 110 to captivate, isolate and easily eject the battery pack 451. The ribbing 904 assists in containing and aligning the battery pack 451 and defines a battery ejection path within the battery chamber 800' that forms at least one battery-retaining structure of the power head 900'.

When compressed by contact with the battery pack 451, the contacts 906 create a compression force that tends to eject the battery pack 451 in a direction, as shown by arrow A, towards the lower end 800'b of the battery chamber 800' back through the chamber port 910, thus further defining the battery-ejection path through the chamber port 910.

A battery chamber access door 912 is configured to sealingly interface with chamber port 910 at the lower end 800'b of the chamber 800'. The access door 912 is rotatably mounted on the handle portion 112 via an offset hinge or pivot connection 914 that is disposed to enable the access door 912 to rotatably swing downwardly or upwardly, as shown by arrow B, either away from the chamber port 910 or towards the chamber port 910, respectively, to either expose or seal the chamber port 910, respectively. The hinge or pivot connection 914 may include a spring (not shown) to leverage an additional closure force, as explained below. The access door 912 includes a free end 912a that rotatably swings downwardly and upwardly as shown by arrow B and a fixed end 912b that is mounted at the offset hinge or pivot connection 914. The free end 912a is configured as a receiving end 916 to engage with, and receive, a barb on a latch, as discussed below. In one embodiment, the hinge or pivot connection 914 is mounted on a distal side 112b of the handle portion 112, as illustrated in FIG. 34.

As mentioned above, a latch 930, having an upper arm 930a with an end 930a' and a lower arm 930b with a lower end 930b', is movably mounted within the handle portion 112 in the vicinity of a proximal side 112a via a pivot connection 932 that is disposed to enable the latch 930 to rotatably swing around the pivot connection 932 such that the ends 930a and 930b of the latch 930 rock alternately to and from the proximal side 112a. The lower arm 930b of the latch 930 is configured as an engaging end or barb 934 that engages with or meshes with the receiving end 916 of the access door 912, thereby engaging the end or barb 934 of the latch 930.

In one embodiment, an energy storage mechanism 936, e.g., a compression spring, may also be disposed in the interior of the handle portion 112 on the proximal side 112a so as to limit motion of the upper arm 930a of the latch 930 in the proximal direction towards proximal side 112a and to bias motion of the upper arm 930a towards the distal side 112b.

A battery chamber access actuation mechanism 940, e.g., an elongated push button as shown, may be disposed in a recessed aperture 942 on the proximal side 112a of the handle portion 112. The battery chamber access mechanism 940 is configured to be actuated by a user of the surgical instrument 10". The recessed aperture 942 penetrates through the proximal side 112a and enables contact between the access actuation mechanism 940 and the lower arm 930b of the latch 930.

When the battery chamber access actuation mechanism 940 is depressed in the distal direction towards distal side 112b, the battery chamber access actuation mechanism 940 urges the lower arm 930b in the distal direction, thereby forcing the latch 930 to rotatably swing around the pivot connection 932, against the compression force of the spring 936, and causing disengagement of the engaging end or barb 934 of the latch 930 from the receiving end 916 of the access door 912. The disengagement of the engaging end or barb 934 of the latch 930 from the receiving end 916 of the access door 912 enables the access door 912 to rotatably swing or rotate downwardly in the direction of arrow B by pivoting around the hinge or pivot connection 914, thereby transferring the access door 912 from a closed position, as shown, to an open position (not shown) and at least partially exposing the chamber port 910. Disposal of the battery chamber access actuation mechanism 940 in the recessed aperture 942 reduces the probability of inadvertent actuation of the battery pack 451 during a surgical procedure. An interlock feature (not shown), e.g., a mechanical feature such as a cap, may be provided to lock the battery chamber access actuation mechanism 940 during the surgical procedure. If the battery pack 451 does not perform adequately during the surgical procedure, the power head 900' may be removed from the operating area to perform the ejection of the battery pack 451.

The rotating or swinging of the access door 912 is further enabled by the compression force, created by the contacts 906, that, as described above, tend to eject the battery pack 451 in a direction, as shown by arrow A, towards the lower end 800'b of the battery chamber back through the chamber port 910. The combination of the rotating or swinging of the access door 912, together with the compression force, and the assistance of gravity, enables the battery pack 451 to overcome constraining frictional forces and to be ejected in a direction that may include the direction of gravity into a sterile environment or container for charging, non-hazardous waste disposal, or recycling. The streamlined configuration of the battery pack 451, together with the provision of the ribbing 904 in the battery chamber 800', facilitates both loading and ejection of the battery pack 451 from the battery chamber 800'. Thus, surgical apparatus 10" is configured to enable ejection of the at least one battery cell 451' of the battery pack 451 by one hand of a user without medical contamination thereof. The access actuation mechanism 940 thus provides access to the battery chamber 800' by opening the access door 912. In effect, the access door 912 serves as a hinged housing cover for the power head 900'. More particularly, since the battery chamber 800' forms at least one battery-retaining structure of the power head 900', the battery-retaining structure further includes the hinged cover or access door 912. When the hinged cover or access door 912 is in a closed position, the hinged cover or access door 912 prevents access to the at least one battery 451' and when the hinged cover or access door 912 is in an open position, the hinged cover or access door 912 enables ejection of the at least one battery 451' from the at least one battery-retaining structure along the battery ejection path.

Additionally, the spring loaded positive and negative electrical connections 802 of contacts 906 provide structure that breaks or interrupts the electrical connection or electrical communication from the battery pack 451 to all external contacts, including to at least one electrical component, within the power head 900' to assist in handling and disposability of the battery pack 451. As defined herein, an electrical component includes an electronic component.

It is contemplated that structure that breaks or interrupts the electrical connection or electrical communication from the battery pack 451 may further include a breakable foil or wire bridge. It is also contemplated that a slow discharge resistor or circuit may be incorporated into the power head 900' to slowly drain the battery at a safe, low temperature rate to further assist in handling and disposability.

In a separate embodiment, the button can be a switch to activate one or more solenoids that translate output shafts to unlatch the battery door and/or release a spring force to eject the battery. For example, the energy storage mechanism 936, e.g., the compression spring, that may also be disposed in the interior of the handle portion 112 on the proximal side 112a so as to limit motion of the upper arm 930a of the latch 930 in the proximal direction towards proximal side 112a and to bias motion of the upper arm 930a towards the distal side 112b, may be replaced by a solenoid (not shown) that is activated by the battery chamber access actuation mechanism 940.

All or part of the spring ejection forces for the battery pack 451 can be restrained or isolated from the pack with a pin or latch so that the battery pack 451 does not normally experience the compression force from the spring 802 during routine operation. The resulting potential energy from the spring 802 can then be released by a separate mechanism (not shown) activated when the battery ejection button is depressed.

In one embodiment, as illustrated in FIGS. 33-34, the power head 900' of the surgical apparatus or instrument 10" further includes at least one sealing member 950 that extends around the one or more battery-retaining structures, e.g., battery chamber 800', such that the sealing member 950 is configured to enable ejection of at least one battery cell 451' of the battery pack 451, or of the entire battery pack 451, from the one or more battery-retaining structures, e.g., the battery chamber 800', along the battery-ejection path as described above without medical contamination of the battery cell(s) 451' or the battery pack 451. The sealing member 950 may incorporate an O-ring or gasket 960 that forms a perimeter on the sealing member 950, that may extend from a position 960a on the proximal side 112a of handle 112 to a position 960b on the distal side 112b of handle 112, to enable the access door 912 to open during ejection of the battery cell(s) 451' or the battery pack 451.

In one embodiment, the power head 900' of the surgical apparatus or instrument 10" includes a handle assembly, e.g., handle portion 112, wherein the handle assembly or handle portion 112 includes the one or more battery-retaining structures, e.g., battery chamber 800', and wherein at least one sealing member 952 extends around the handle assembly or handle portion 112 or the one or more battery-retaining structures such as battery chamber 800' such that the one or more sealing members 952 are configured to enable ejection of at least one battery cell 451', or the entire battery pack 451, from the one or more battery-retaining structures, e.g., battery chamber 800', along the battery-ejection path as described above without medical contamination of the battery cell(s) 451' or the battery pack 451. In a similar manner as with respect to sealing member 950, sealing member 952 may incorporate O-ring or gasket 960, that may extend from a position 960a on the proximal side 112a of handle 112 to a position 960b on the distal side 112b of handle 112, to enable the access door 912 to open during ejection of the battery cell(s) 451' or the battery pack 451.

In one embodiment, the power head 900' of the surgical apparatus or instrument 10" includes an instrument housing, e.g., instrument housing 110, wherein the instrument housing 110 includes the one or more battery-retaining structures, e.g., battery compartment 800', wherein sealing member 954 extends around the instrument housing 110 or the one or more battery-retaining structures such as battery chamber 800' such that the one or more sealing members 954 are configured to enable ejection of at least one battery cell 451', or the entire battery pack 451, from the one or more battery-retaining structures, e.g., battery chamber 800', without medical contamination of the battery cell(s) 451' or the battery pack 451. Again, as with respect to sealing members 950 and 952, sealing member 954 may incorporate O-ring or gasket 960, that may extend from a position 960a on the proximal side 112a of handle 112 to a position 960b on the distal side 112b of handle 112, to enable the access door 912 to open during ejection of the battery cell(s) 451' or the battery pack 451.

As can be appreciated from the foregoing description of the sealing members 950, 952 and 954 of the power head 900', the sealing members 950, 952 and 954 provide an integral or separate seal or gasket or adhesive system between the battery pack 451 and other housing components, while allowing electrical communication between the battery pack 451 and the contacts 906 that may be spring loaded positive and negative electrical connections 802.

As can also be appreciated from the foregoing description, the present disclosure relates also to the power head 900' having at least one battery-retaining retaining structure, e.g., battery chamber 800', that is configured to retain at least one battery cell 451'. The one or more battery-retaining structures are configured to enable ejection of the battery cell(s) 451' without medical contamination thereof, e.g., by ejection along a battery ejection path defined by the ribbing 904 within the battery chamber 800'.

In one embodiment, the at least one battery-retaining structure, e.g., battery chamber 800', is configured to enable ejection of the battery cell(s) 451' by one hand of a user. The ejection of the battery cell(s) 451' occurs without medical contamination thereof, e.g., by ejection along a battery ejection path defined by the ribbing 904 within the battery chamber 800'.

In one embodiment, as illustrated in FIG. 34, the power head 900' includes at least one energy storage mechanism, e.g., spring 802, that is operatively coupled to the one or more battery-retaining structures, e.g., battery chamber 800', wherein actuation of the one or more energy storage mechanisms, e.g., spring 802, enables ejection of the battery cell(s) 451' without medical contamination thereof, e.g., by ejection along a battery ejection path defined by the ribbing 904 within the battery chamber 800'.

In a similar manner as described above with respect to energy storage mechanism 936, the spring 802 may be replaced by a solenoid (not shown) that is activated by battery chamber access actuation mechanism 940.

In one embodiment, as also illustrated in FIG. 34, the power head 900' includes at least one energy storage mechanism, e.g., spring 802, that is operatively coupled to the one or more battery-retaining structures, e.g., battery chamber 800', and is configured wherein actuation of the one or more energy storage mechanisms, e.g., spring 802 via actuation of the battery chamber access actuation mechanism 940, enables ejection of the battery cell(s) 451' by one hand of a user and is configured wherein the ejection of the battery cell(s) 451' by the one hand of a user enables ejection of the battery cell(s) 451' without medical contamination thereof, e.g., by ejection along a battery ejection path defined by the ribbing 904 within the battery chamber 800'.

Returning again to FIGS. 4-12, as described previously, FIGS. 4-12 illustrate various internal components of the instrument 10, including a drive motor 200, a drive tube 210 and a firing rod 220 having a proximal portion 222 and a distal portion 224. The drive tube 210 is rotatable about drive tube axis C-C extending therethrough. Drive motor 200 is disposed in mechanical cooperation with drive tube 210 and is configured to rotate the drive tube 210 about drive gear axis C-C. In one embodiment, the drive motor 200 may be an electrical motor or a gear motor, which may include gearing incorporated within its housing.

Referring now to FIGS. 37-43, power head 900' of surgical instrument 10" includes the first housing portion 110a and the second housing portion 110b defining the plurality of ports or boss locators 111, which as described above with respect to FIG. 3, align the two housing halves or portions 110a and 110b to each other and are disposed within the second housing portion 110b to enable joining of the first housing portion 110a and the second housing portion 110b.

Figure 37:
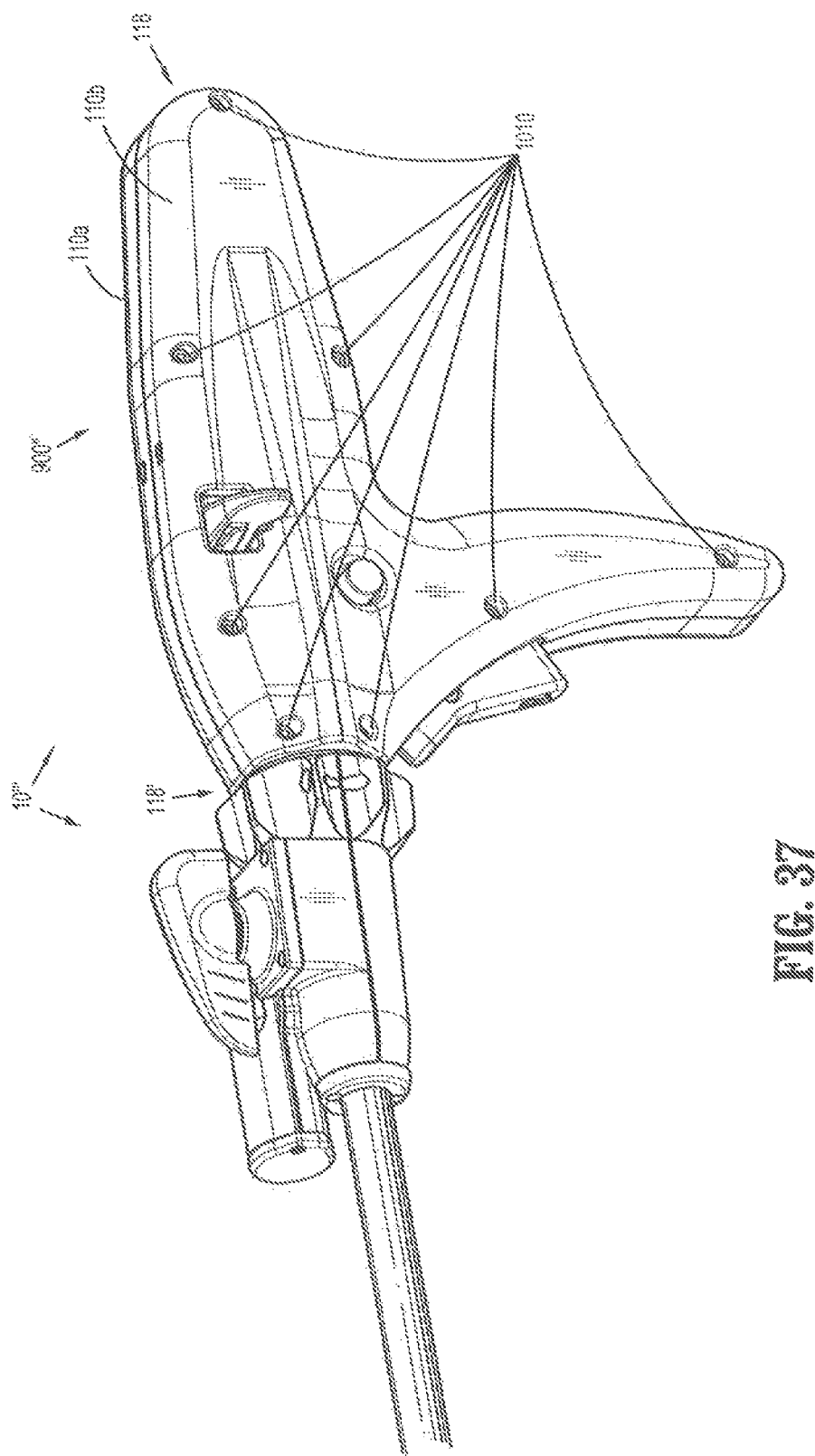
FIG. 37 is a perspective view of the exterior of the housing of the power head of the surgical instrument according to the present disclosure.
Figure 38:
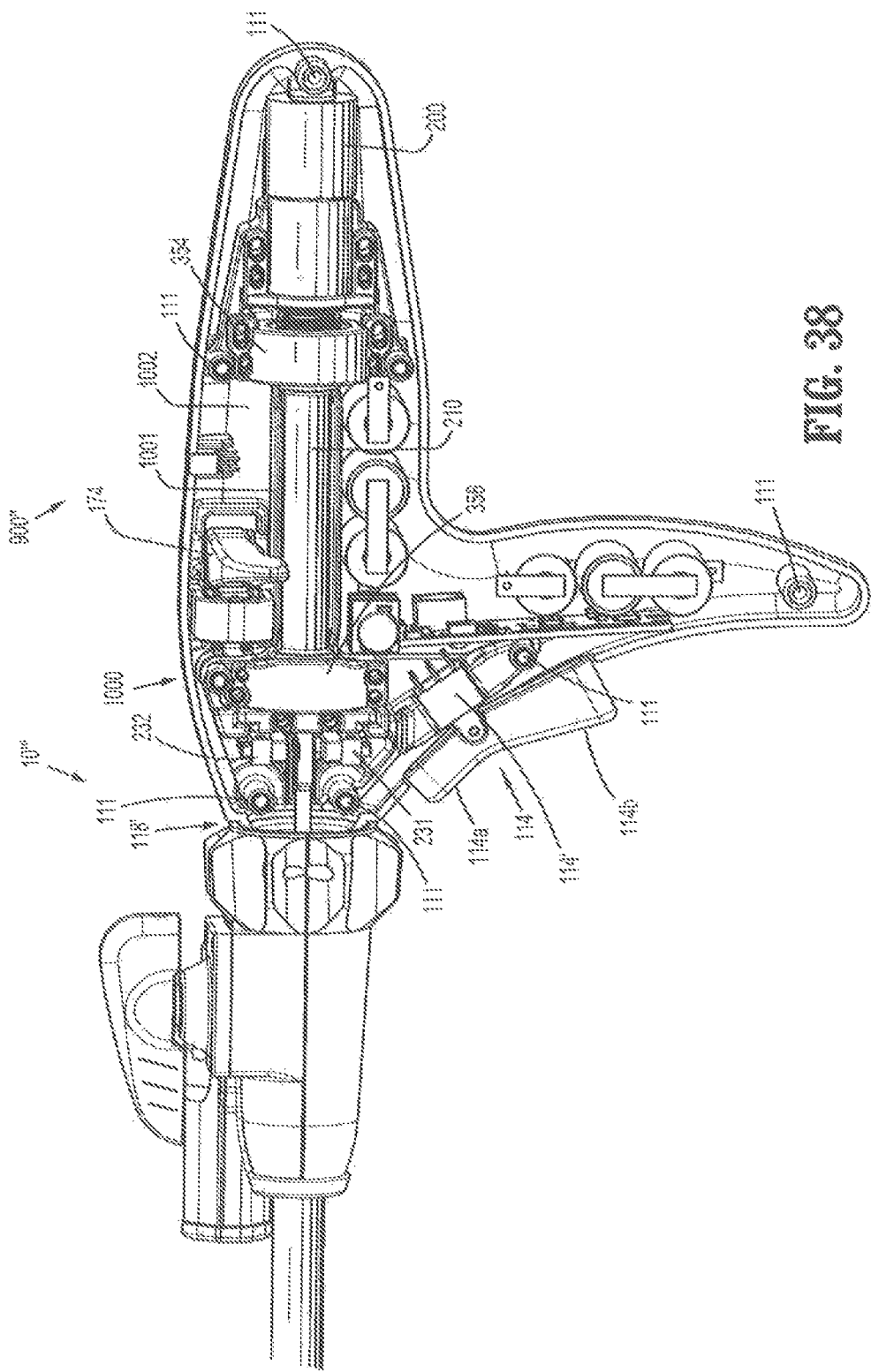
FIG. 38 is a partial cross-sectional view of the power head of FIG. 37 illustrating a set of operating components mounted on a structural member or chassis according to one embodiment of the present disclosure.

Referring particularly to FIGS. 37-38, in one embodiment according to the present disclosure, power head 900' of surgical instrument 10" includes a structural member or chassis 1001 for mounting a set of operating components 1000 of the power head 900' and/or surgical instrument 10'''. The housing 110, being formed of the first housing portion 110a and the second housing portion 110b, enables access to an interior volume 1002 of the power head 900' of surgical instrument 10''' that is encompassed by the housing 110. As described above with respect to FIGS. 4-12, a set of operating components are mounted in the interior volume 1002. More particularly, the set of operating components 1000 includes, among others, drive motor 200 (and associated gear assembly), proximal bearing 354 and distal bearing 356, drive tube 210, powered articulation switch 174, and portions of switch 114, that may include first and second switches 114a and 114b formed together as a toggle switch external to the interior volume 1002 and having an internal interface 114' that is substantially disposed within the interior volume 1002, and position and limit switches (e.g., shaft start position sensor 231 and clamp position sensor 232) that are disposed within the interior volume 1002.

As described above, the boss locators 111 align the two housing halves 110a and 110b to join together as housing 110. In addition, since the set of operating components 1000 have a proper configuration for alignment when mounted within the interior volume 1002 encompassed by the housing 110, the boss locators 111 also enable the proper configuration for alignment of the set of operating components 1000.

In one embodiment according to the present disclosure, the set of operating components 1000 may be mounted on the chassis 1001 rather than directly on the housing halve or portion 110a as applicable to power head 900' of surgical instrument 10 (see FIG. 4).

Figure 39:
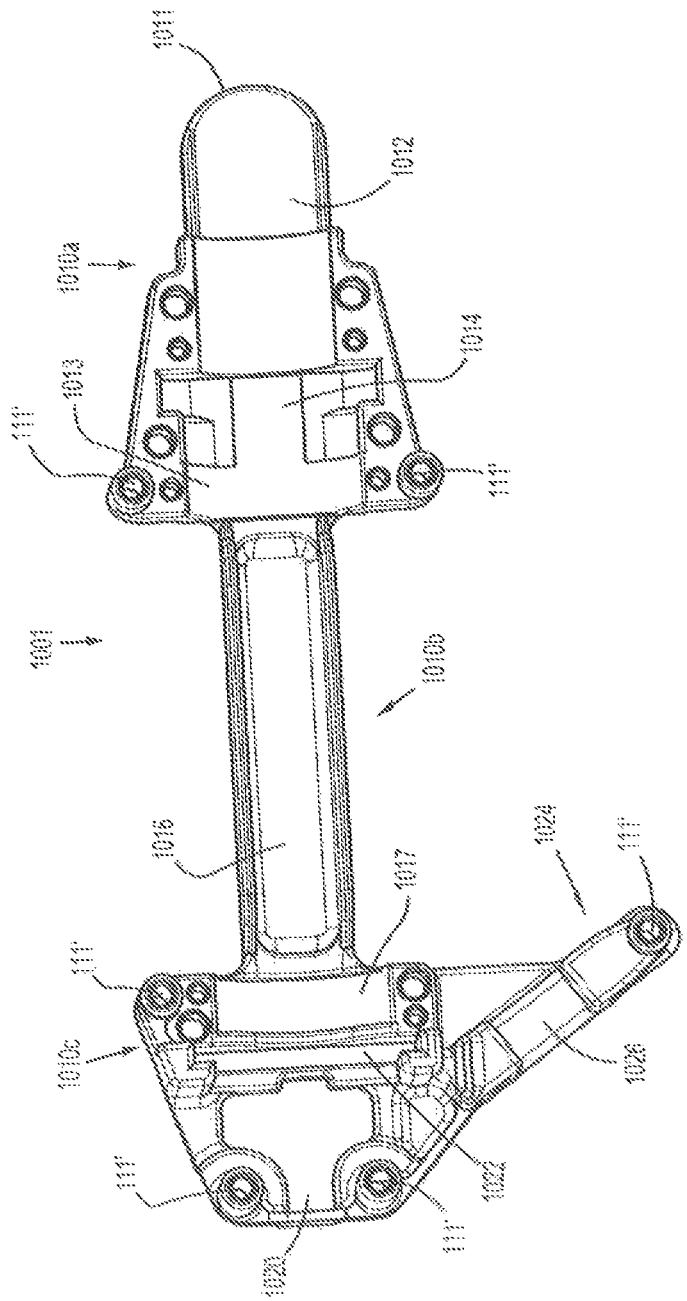
FIG. 39 is a view of one side of the structural member or chassis showing the features for mounting the operating components according to one embodiment of the present disclosure.

As illustrated in FIG. 39, the chassis 1001 includes boss locator ports 111' that are configured to align with the boss locators 111 of the housing halves or portions 110a and 110b (see FIG. 38). The chassis 1001 is configured with a proximal portion 1010a, a central portion 1010b, and a distal portion 1010c, wherein the proximal portion 1010a, the central portion 1010b and the distal portion 1010c are operatively connected therebetween or integrally formed therebetween to yield the chassis 1001. The proximal portion 1010a is configured with a first recess 1012 and a second recess 1014, both recesses being formed within the chassis 1001 to receive particular components of the set of operating components 1000. The second recess 1014 is distal to the first recess 1012. More particularly, first recess 1012 is configured to receive and align the drive motor 200 (and associated gear assembly) while the second recess 1014 is configured to receive and align the proximal bearing 354 (see FIG. 38). In the exemplary embodiment illustrated in FIG. 38, the proximal portion 1010*a* has a proximal portion 1011 with a partially oval-shaped cross section and is adjacent to a distal portion 1013 that has a trapezoidal-shaped cross section. The first recess 1012 is formed in the proximal portion 1011 that has a partially oval-shaped cross section while the second recess 1014 is formed within the distal portion 1013 that has a trapezoidal-shaped cross section.

The central portion 1010*b*, which may be semi-cylindrically shaped with a corresponding rectangular-shaped cross section, is configured with a recess 1016 formed within the chassis 1001. The recess 1016 is configured to receive and align the drive tube 210.

In the exemplary embodiment illustrated in FIG. 39, in conjunction with FIG. 38, the distal portion 1010*c* has a trapezoidal-shaped cross section with a recess 1017 formed therein that is configured to receive and align the distal bearing 356. The distal portion 1010*c* has a generally T-shaped aperture 1020 that is distal to the recess 1017. The aperture 1020 is configured to enable receipt, retention and alignment of the position and limit switches, e.g., shaft start position sensor 231 and clamp position sensor 232. The distal portion 1010*c* further includes a slot 1022 formed therein and disposed between the recess 1017 and the aperture 1020. The slot 1022 serves as a datum for alignment of the set 1000 of operating components and is configured and disposed to retain and align the alignment plate 350 which locates the firing rod 220 concentrically, as previously described with respect to FIGS. 6 and 7. Again, the alignment plate 350 includes an aperture 355 therethrough, which has a non-round cross-section (see FIG. 7). The non-round cross-section of the aperture 355 prevents rotation of proximal portion 222 of firing rod 220, thus limiting proximal portion 222 of firing rod 220 to axial translation therethrough. The alignment plate 350 also functions as a bearing support and mechanical stop. The distal surface 351 of the alignment plate 350 is also used as a mounting face and datum for the start position sensor 231 and the clamp position sensor 232.

The distal portion 1010*c* further includes a downwardly directed protrusion or extension 1024 in which is formed a recess 1026 that is configured to receive and align the internal interface 114' of the toggle switch 114, and that is substantially disposed within the interior volume 1002.

As can be appreciated from the foregoing description, the chassis 1001 is configured to provide the proper configuration for alignment for the set of operating components 1000 mounted on the chassis 1001 if the chassis 1001 and set of operating components 1000 are mounted within the interior volume 1002 of the housing 110. Though not explicitly illustrated in FIGS. 37-43, the chassis 1001 is configured to provide the proper configuration for alignment for a replacement set of operating components (not explicitly shown) of the surgical instrument 10''' mounted on the chassis 1001 if the chassis 1001 and replacement set of operating components are mounted within the interior volume 1002 of the housing 110. Thus the chassis 1001 is configured to provide the proper configuration for alignment for the set of operating components 1000 and/or the replacement set of operating components including either the set of operating components 1000 or the replacement set of operating components. Those skilled in the art will recognize that although the replacement set of operating components is generally identical to an original set of operating components 1000 that would be first provided by the manufacturer with the power head 900'' of surgical instrument 10''', the replacement set of operating components need only be identical to the original set of operating components 1000 to the extent necessary to maintain alignment, fit and suitable operability of the surgical instrument 10''' when inserted within the interior volume 1002.

Referring to FIG. 37, and as described above with respect to FIGS. 4-12, the housing 110 includes at least first housing portion 110*a* and second housing portion 110*b*. At least the first housing portion 110*a* is removable to expose at least a portion of the interior volume 1002 of the surgical instrument 10'. The first housing portion 110*a* defines a plurality of ports 111 and the second housing portion 110*b* defines a plurality of ports 1010 that are disposed to enable the proper configuration for alignment of the set of operating components 1000 and of a replacement set of operating components (not explicitly shown) if the first housing portion 110*a* and the second housing portion 110*b* are joined together.

In addition, as illustrated in FIG. 39, the chassis 1001 defines a plurality of ports 111' that are disposed to enable the proper configuration for alignment of the set of operating components 1000 and of a replacement set of operating components (not explicitly shown) if or wherein the first housing portion 110*a* and the second housing portion 110*b* are joined together and if or wherein the chassis 1001 and the set of operating components 1000 or replacement set of operating components are mounted within the interior volume 1002 of the housing 110.

It is contemplated that clips, buckles, snaps, quick turn fasteners or other suitable connectors make be incorporated at appropriate locations on the first and second housing portions 110*a* and 110*b*, respectively, and/or on the chassis 1001 to provide ease of disassembly.

The chassis 1001 can be made from ferrous, conductive or magnetic metals to shield electronic components, e.g., the control switch 114 or shaft start position sensor 231 and clamp position sensor 232, from radio frequency (RF) noise and electro-magnetic interference (EMI). The structural member/chassis 1001 can also be operatively coupled or operatively connected to such components, including the drive motor 200, as a common ground for direct current (DC) applications.

Figure 40:
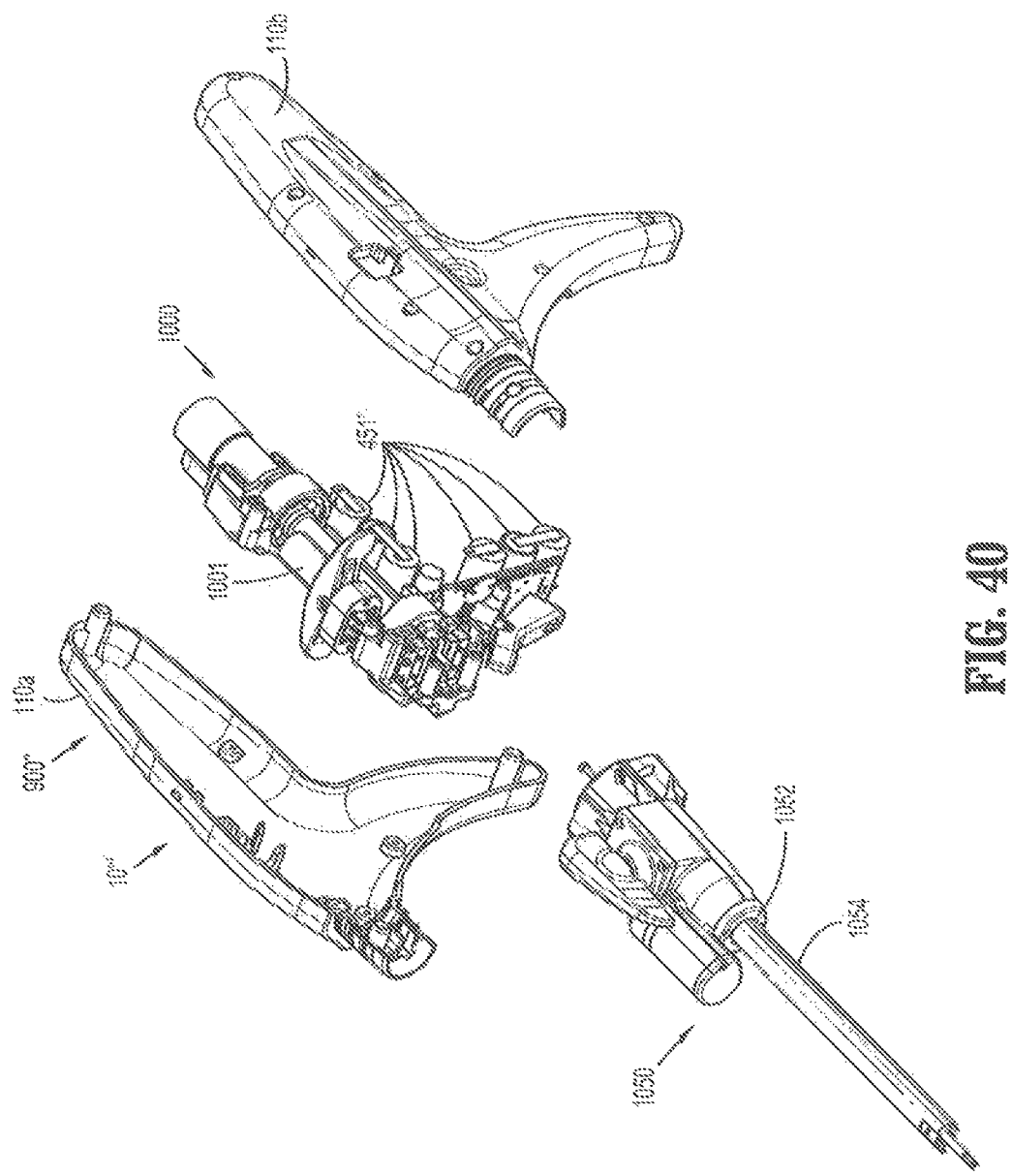
FIG. 40 is an exploded perspective view of the power head of FIG. 36 showing the housing portions and a set of operating components mounted on the structural member or chassis according to the present disclosure.
Figure 41:
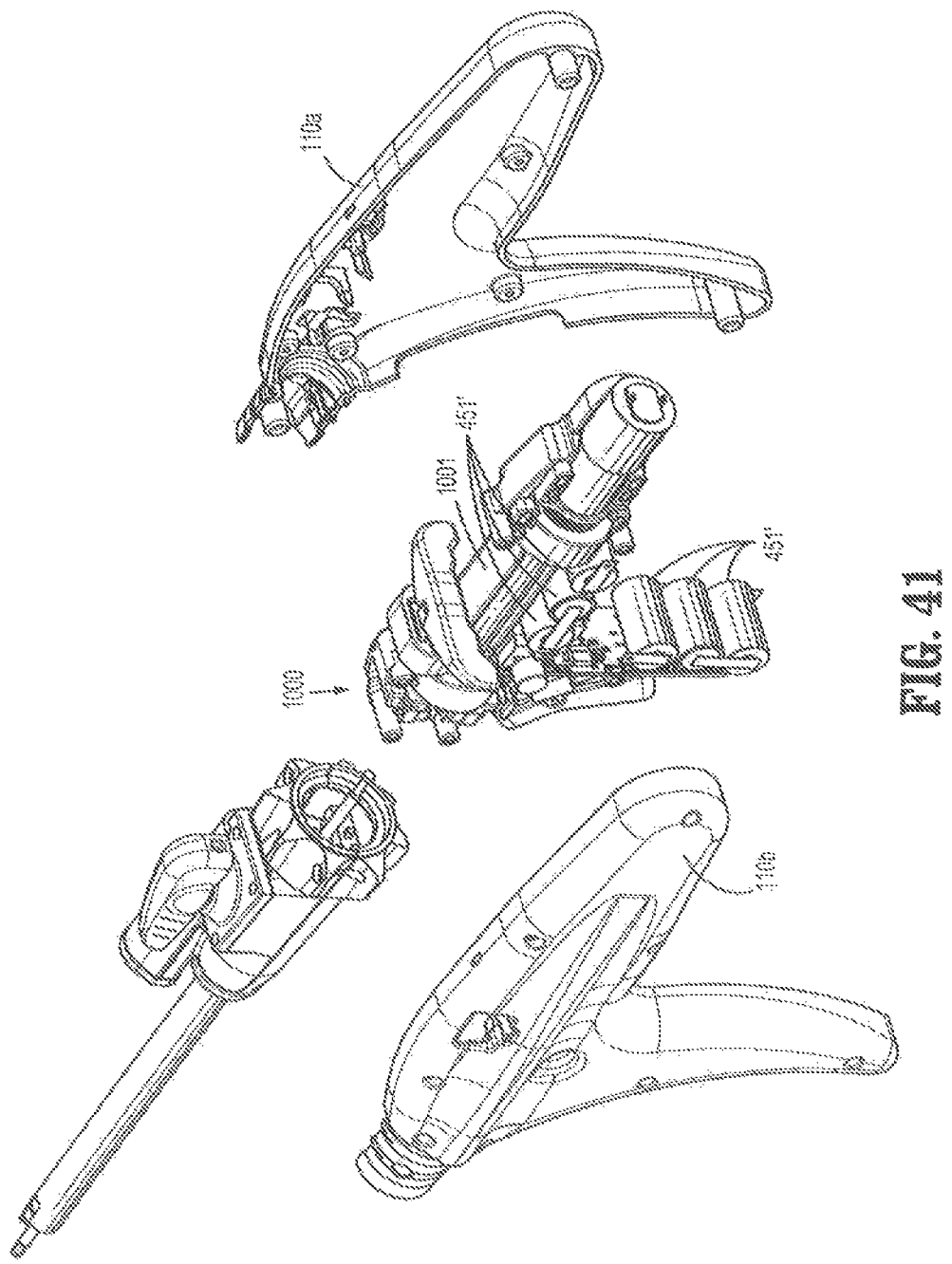
FIG. 41 is another exploded perspective view of the power head of FIG. 36 showing the housing portions and a set of operating components mounted on the structural member or chassis according to the present disclosure.

FIGS. 40-41 illustrate exploded views of the surgical instrument 10''' showing first and second housing portions 110*a* and 110*b* and, as described above with respect to FIGS. 37-39, the set of operating components 1000 mounted on the chassis 1001.

The electrosurgical instrument 10''' includes a rotating front end interchange assembly 1050 that is operatively coupled to the power head 900'' to enable the power head 10'' to drive and operate the firing rod 220 (see FIG. 6). The rotating front end interchange assembly 1050 includes an interface connection 1052 to enable interchanging of front end 1054 of firing rod 220. A Tyco Healthcare Model EGIA front end 1054 is shown. The interchange assembly 1050 is configured to receive and operate other front ends 1054, e.g., Tyco Healthcare Model EEA having a circular cross-section, Model EEA having a circular cross-section, Model TA having a right angle cross-section, or a cutter, a cautery, an RF energy, or a clamp or a grasper front end.

Figure 42:
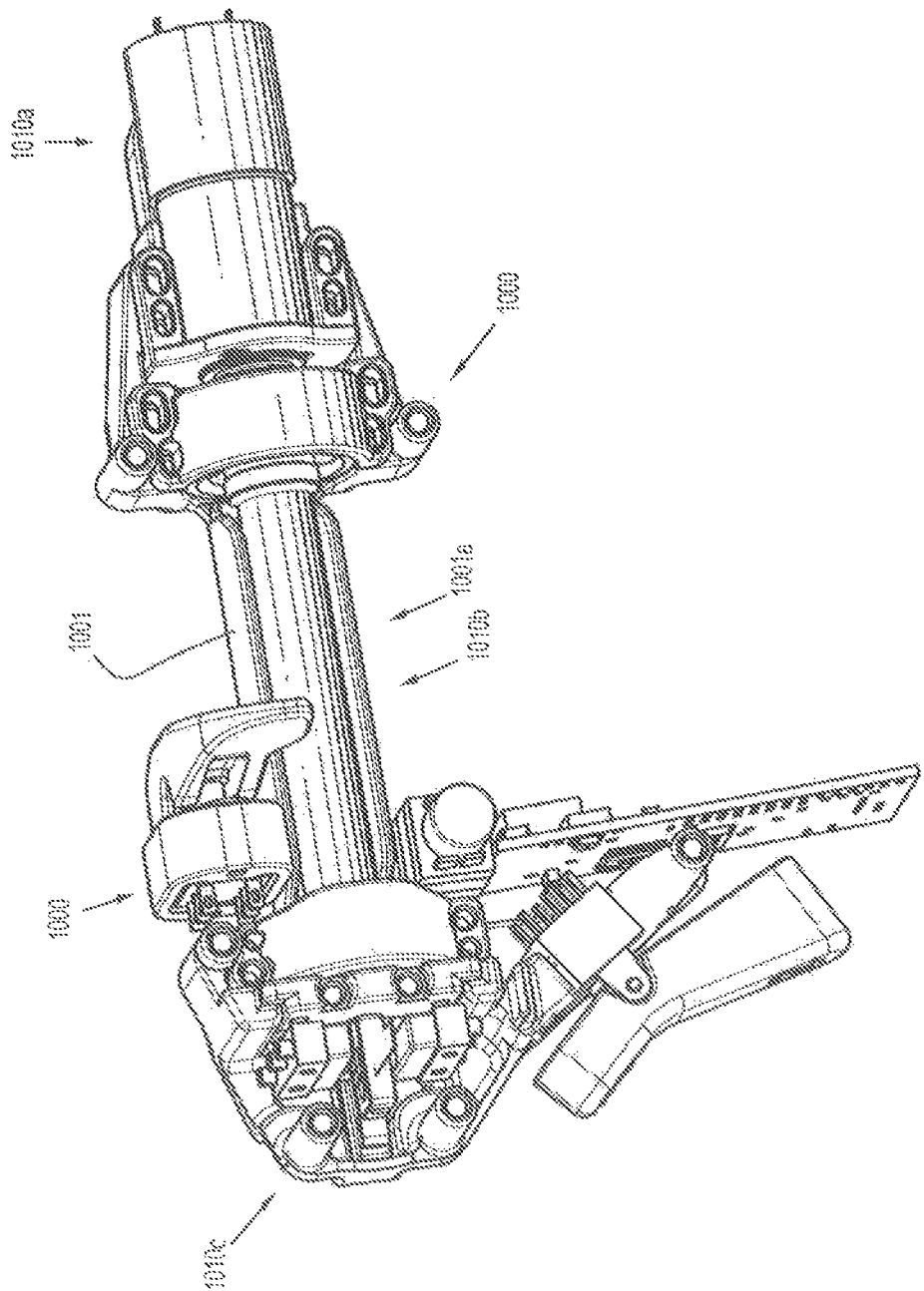
FIG. 42 is a view of the side of the structural member or chassis as illustrated in FIG. 39 and illustrating a set of operating components mounted on the structural member or chassis.
Figure 43:
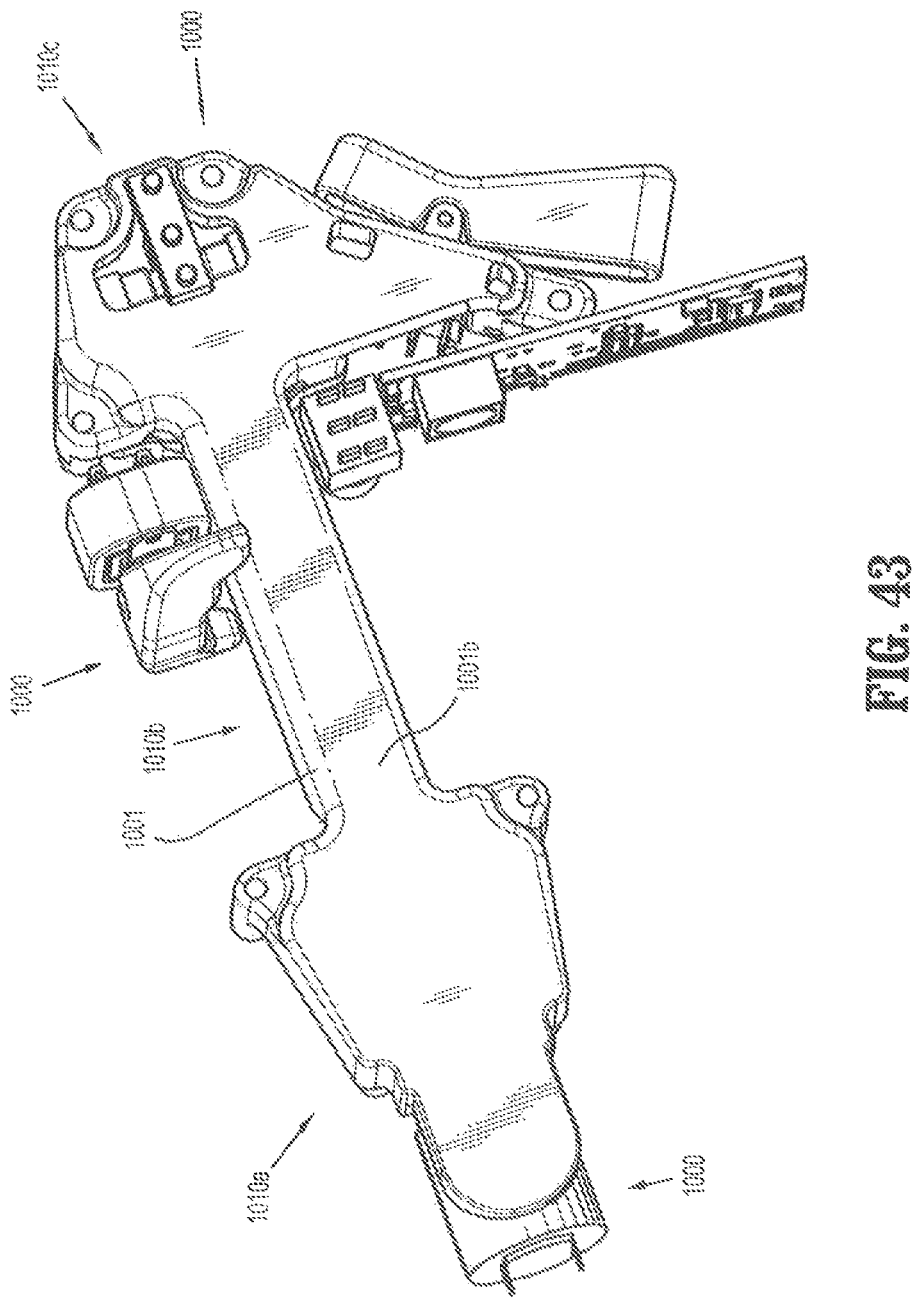
FIG. 43 is a view of another side of the structural member or chassis and illustrating a set of operating components mounted on the structural member or chassis.

FIG. 42 is a view of an open side 1001a of the chassis 1001 showing the set of operating components 1000 as mounted on the chassis 1001 with the open side 1001a facing the viewer. FIG. 43 is a view of a closed side 1001b of the chassis 1001 showing the set of operating components 1000 as mounted on the chassis 1001 with the closed side 1001b facing the viewer.

In one embodiment, the chassis 1001 is formed from metal and the housing 110 is formed from a polymer. The set of operating components 1000 or the replacement set of operating components (not shown) includes at least one electrical component, e.g., battery cell(s) 451' (see FIGS. 40-41), and the chassis 1001 is configured to enable electrical grounding of the electrical component.

Thus, as can be appreciated from the above disclosure, a power head 900' of a surgical instrument such as surgical instrument 10", wherein the power head 900' includes the chassis 1001 improves reusability or reprocessing of costly components by enabling easier removal/disposal of a contaminated housing or cover while enabling maintaining all or many critical component assembly alignments and positions. In addition, chassis 1001 provides the following advantages:
   a. enables additional durability, strength and structural support for the surgical instrument 10";
   b. enables utilization or deployment as a chassis platform for mounting components, fasteners and removable housing covers;
   c. enables easier multi-plane accessibility for assembling or repairing parts versus a single plane housing cover assembly configuration;
   d. enables greater endurance of multiple cycles of installing and removing fasteners for multiple reprocess, service and/or repair cycles vs. standard plastic housing fastener bosses;
   e. enables higher tolerance datum positioning for accurate bearing and mechanism alignment as compared to net molded housing assembly methods;
   f. enables utilization or deployment as an electrical ground platform for all components within a DC or microelectronic device; and
   g. creates Radio Frequency (RF) and Electromagnetic Interference (EMI) shielding for electronic components within the device.

Figure 44:
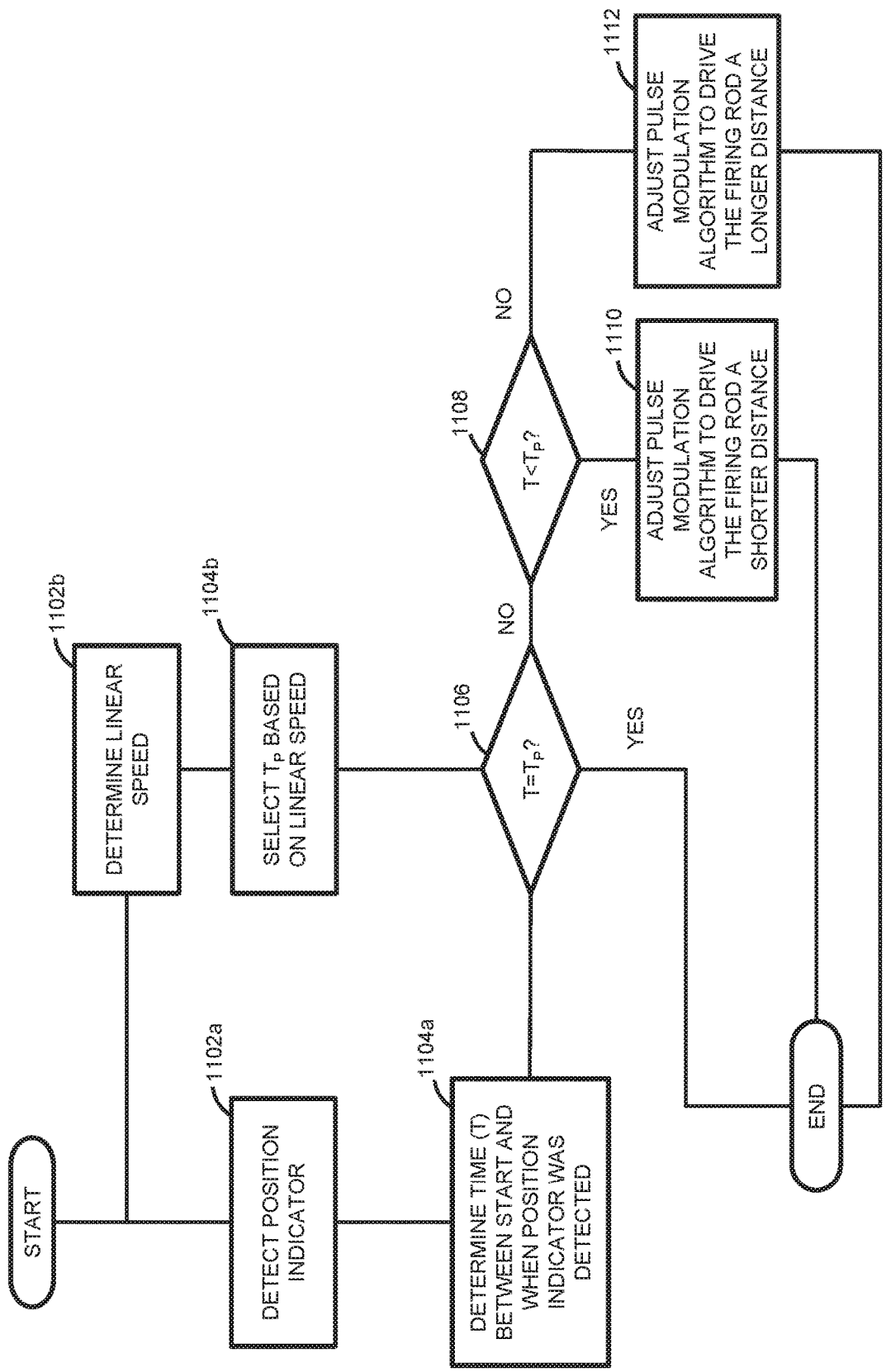
FIG. 44 is a flow chart depicting a method for calibrating a powered surgical instrument according to an embodiment of the present disclosure.

FIG. 44 is a flowchart depicting a calibration algorithm stored in the microcontroller 500 for calibrating the instrument 10. The microcontroller 500 stores a pulse modulation algorithm that is used to control the drive motor 200. The calibration algorithm of microcontroller 500 is used to adjust program coefficients in the pulse modulation algorithm to calibrate the instrument 10. As shown in FIG. 44, instrument 10 is started and the firing rod 220 is translated while the linear displacement sensor 237 is placed in an active state in order to detect the first indicator 320a. Upon detection of the first indicator 320a, by the linear displacement sensor 237 in step 1102a, the position calculator 416 determines, in step 1104a, a time "T" that elapsed between when the firing rod 220 started translating and when the linear displacement sensor 237 detected the first indicator 320a. The position calculator also determines the linear speed of the firing rod 220 based on a rotational speed of the drive motor 200 in step 1102b. The position calculator 416 provides the time "T" and the linear speed to the microcontroller 500, which compares the time "T" to a stored predetermined time "$T_P$". The stored predetermined time "$T_P$" is selected by the microprocessor 500 based on the received linear speed in step 1104b. In step 1106, if the microcontroller 500 determines that the time "T" is equal to the predetermined time "$T_P$", the calibration algorithm is ended and the drive motor 200 translates the firing rod its predetermined distance. If the times "T" and "$T_P$" are not equal, the algorithm proceeds to step 1108 where the microcontroller 500 determines whether time "T" is less than the predetermined time "$T_P$". If time "T" is less than the predetermined time "$T_P$", the algorithm proceeds to step 1110 where the microcontroller 500 adjusts a program coefficient in the pulse modulation algorithm to control the drive motor 200 to advance the firing rod 220 for a distance shorter than the predetermined distance. If time "T" is greater than the predetermined time "$T_P$", the calibration algorithm proceeds to step 1112 where the microcontroller 500 adjusts the program coefficient in the pulse modulation algorithm to control the drive motor 200 to advance the firing rod 220 for a distance longer than the predetermined distance.

It will be understood that various modifications may be made to the embodiments shown herein. Therefore, the above description should not be construed as limiting, but merely as exemplifications of preferred embodiments. Those skilled in the art will envision other modifications within the scope and spirit of the claims appended hereto.

What is claimed is:

1. A method for calibrating a surgical instrument comprising:
   initiating translation of a firing rod;
   detecting the translation of the firing rod;
   determining a time between when translation of the firing rod is initiated and when the translation is detected by a sensor;
   comparing the time with a predetermined time; and
   displaying the translation of the firing rod, the detecting the translation of the firing rod, and the comparing of the time with the predetermined time on a video display with corresponding voice pronouncements.

2. The method of claim 1, wherein:
   initiating translation of the firing rod includes a drive motor configured to translate the firing rod; and
   adjusting at least one program coefficient in a pulse modulation algorithm based on a comparison between the time and the predetermined time, the pulse modulation algorithm stored in a memory.

3. The method of claim 2, further comprising:
   determining a linear speed of the firing rod; and
   selecting the predetermined time based on the determined linear speed of the firing rod.

4. The method of claim 3, wherein if the time is less than the predetermined time, the at least one program coefficient is adjusted so that the firing rod is translated a relatively shorter distance.

5. The method of claim 3, wherein if the time is greater than the predetermined time, the at least one program coefficient is adjusted so that the firing rod is translated a relatively longer distance.

6. A surgical instrument comprising:
   a firing rod translatable along an axis of the surgical instrument;
   a sensor configured to detect translational motion of the firing rod along the axis, the sensor determining a linear speed of the firing rod;
   a microcontroller having a pulse modulation algorithm stored therein, the microcontroller receiving the time from the position calculator and comparing the time to a predetermined time and adjusting the at least one program coefficient based on the comparison between the time and the predetermined time, wherein the microcontroller selects the predetermined time based on the linear speed of the firing rod; and a position calculator configured to determine a time between when the firing rod begins translational motion along the axis and when the sensor detects the translational motion of the firing rod along the axis, wherein the microcontroller executes a calibration algorithm to adjust at least one program coefficient in the pulse modulation algorithm.

7. The surgical instrument of claim 6, wherein the microcontroller executes displaying on a video display the time of detecting of the translation of the firing rod, the comparing of the time with the predetermined time, and the adjusting the at least one program coefficient in the pulse modulation algorithm based on the comparison between the time and the predetermined time with corresponding voice pronouncements.

8. The surgical instrument of claim 6, wherein the sensor detecting the translational motion of the firing rod is enabled by at least one indicator on the firing rod.

9. A method of assembling a power head of a surgical instrument comprising:

mounting a set of operating components of a power head on a chassis such that the set of operating components has a proper configuration for alignment in at least two orthogonal planes when the chassis and the set of components mounted thereon are deployed within an interior volume encompassed by a housing of the power head; and deploying the set of operating components mounted on the chassis within the interior volume encompassed by the housing, wherein deploying the set of operating components mounted on the chassis within the interior volume provides the proper configuration for alignment in the at least two orthogonal planes of the set of operating components.

10. The method of assembling a power head according to claim 9, wherein mounting the set of operating components on the chassis occurs outside of the housing and prior to deploying the set of operating components mounted on the chassis within the interior volume.

11. The method of assembling a power head according to claim 9, wherein mounting of the set of operating components on the chassis includes removably attaching a loading unit to an endoscopic portion, the loading unit including an end effector being in mechanical cooperation with a firing rod of the power head so that the firing rod drives a surgical function of the end effector; and configuring a control system that includes sensors coupled to a drive motor of the power head, to the firing rod, and to the loading unit wherein the sensors of the control system are configured to guide deploying the set of operating components mounted on the chassis within the interior volume to provide the proper configuration for alignment in the at least two orthogonal planes of the set of operating components, the control system including a microcontroller coupled to the sensors, the microcontroller configured to determine the operating status of the power head as a function of the detected operating parameters of the proper configuration for alignment in at least two orthogonal planes of the set of operating components mounted on the chassis.

12. The method of assembling a power head according to claim 9, comprising:

removing the chassis from the interior volume encompassed by the housing, thereby concurrently removing the set of operating components of the power head;

mounting a replacement set of operating components on the chassis; and deploying the set of replacement operating components mounted on the chassis within the interior volume, wherein deploying the replacement set of operating components mounted on the chassis within the interior volume provides the proper configuration for alignment of the replacement set of operating components in the at least two orthogonal planes.

13. The method of assembling a power head according to claim 12, wherein mounting the set of replacement operating components on the chassis occurs outside of the housing and prior to deploying the set of replacement operating components mounted on the chassis within the interior volume.

14. The method of assembling a power head according to claim 9, wherein mounting the set of replacement operating components on the chassis includes:
the chassis formed from metal,
the housing formed from a polymer, and
the set of operating components includes at least one electrical component, and electrically grounding the at least one electrical component.

15. The method of assembling a power head according to claim 9, wherein mounting the set of replacement operating components on the chassis includes:
the power head having a housing formed of two halves that are attached to each other at least two boss locators on each housing half, the boss locators disposed to align the two housing halves to each other,
the chassis having at least two boss locator ports that are configured and disposed to align with the at least two boss locators on each housing half, and
joining the two housing halves together such that the at least two boss locator ports align with the at least two boss locators on each housing half.

16. The method of assembling a power head according to claim 15, wherein mounting the set of replacement operating components on the chassis includes:
the power head has a firing rod that causes ejection of surgical fasteners,
the chassis further includes a slot configured and disposed as a datum for alignment in the at least two orthogonal planes of the firing rod with respect to the power head;
positioning the slot as a datum; and
aligning the firing rod with respect to the power head.

* * * * *